US011981723B2

(12) United States Patent
Hermiston et al.

(10) Patent No.: US 11,981,723 B2
(45) Date of Patent: May 14, 2024

(54) METHOD OF TARGETING EXOSOMES

(71) Applicant: GLADIATOR BIOSCIENCES, INC., Mill Valley, CA (US)

(72) Inventors: Terry Hermiston, Mill Valley, CA (US); Maxine Bauzon, Hercules, CA (US); Christopher H. Contag, San Jose, CA (US); Jonathan Hardy, East Lansing, MI (US); Masamitsu Kanada, Okemos, MI (US)

(73) Assignee: GLADIATOR BIOSCIENCES, INC., Mill Valley, CA (US)

( * ) Notice: Subject to any disclaimer, the term of this patent is extended or adjusted under 35 U.S.C. 154(b) by 409 days.

(21) Appl. No.: 16/643,997

(22) PCT Filed: Sep. 5, 2018

(86) PCT No.: PCT/US2018/049619
§ 371 (c)(1),
(2) Date: Mar. 3, 2020

(87) PCT Pub. No.: WO2019/050998
PCT Pub. Date: Mar. 14, 2019

(65) Prior Publication Data
US 2021/0062143 A1 Mar. 4, 2021

Related U.S. Application Data

(60) Provisional application No. 62/593,014, filed on Nov. 30, 2017, provisional application No. 62/584,565, filed on Nov. 10, 2017, provisional application No. 62/569,403, filed on Oct. 6, 2017, provisional application No. 62/569,411, filed on Oct. 6, 2017, provisional application No. 62/554,530, filed on Sep. 5, 2017, provisional application No. 62/554,533, filed on Sep. 5, 2017.

(51) Int. Cl.
| *A61K 38/36* | (2006.01) |
| *A61K 38/18* | (2006.01) |
| *A61K 38/48* | (2006.01) |
| *A61K 45/06* | (2006.01) |
| *A61K 47/64* | (2017.01) |
| *A61K 49/00* | (2006.01) |
| *C07K 14/745* | (2006.01) |
| *C12N 5/073* | (2010.01) |
| *C12N 5/0789* | (2010.01) |
| *C12N 5/095* | (2010.01) |

(52) U.S. Cl.
CPC ........ *C07K 14/745* (2013.01); *A61K 38/1808* (2013.01); *A61K 38/36* (2013.01); *A61K 38/4833* (2013.01); *A61K 38/4846* (2013.01); *A61K 38/4866* (2013.01); *A61K 47/645* (2017.08); *A61K 49/0043* (2013.01); *C12N 5/0605* (2013.01); *C12N 5/0647* (2013.01); *C12N 5/0695* (2013.01); *A61K 45/06* (2013.01); *C07K 2319/035* (2013.01); *C07K 2319/60* (2013.01)

(58) Field of Classification Search
CPC ................ A61K 38/1808; A61K 38/36; A61K 38/4833; A61K 38/4846; A61K 38/4866; A61K 45/06; A61K 47/645; A61K 49/0043; A61K 38/18; A61K 38/48; C07K 14/745; C07K 2319/035; C07K 2319/60; C12N 2502/30; C12N 5/0605; C12N 5/0631; C12N 5/0693; C12N 5/0695; C12N 5/073
See application file for complete search history.

(56) References Cited

U.S. PATENT DOCUMENTS

| 5,440,013 | A | 8/1995 | Kahn |
| 5,446,128 | A | 8/1995 | Kahn |
| 5,475,085 | A | 12/1995 | Kahn |
| 5,597,457 | A | 1/1997 | Craig et al. |
| 5,618,914 | A | 4/1997 | Kahn |
| 5,656,484 | A | 8/1997 | Bouma et al. |
| 5,670,155 | A | 9/1997 | Kahn |
| 5,672,681 | A | 9/1997 | Kahn |
| 5,674,976 | A | 10/1997 | Kahn |
| 5,710,245 | A | 1/1998 | Kahn |
| 5,790,421 | A | 8/1998 | Osslund |
| 5,840,833 | A | 11/1998 | Kahn |
| 5,859,184 | A | 1/1999 | Kahn et al. |
| 5,889,155 | A | 3/1999 | Ashkenazi et al. |
| 5,929,237 | A | 7/1999 | Kahn |
| 6,093,573 | A | 7/2000 | Beamer et al. |
| 6,261,569 | B1 | 7/2001 | Comis et al. |

(Continued)

FOREIGN PATENT DOCUMENTS

| AU | 2013/200991 | 4/2014 |
| CN | 101426906 | 6/2013 |

(Continued)

OTHER PUBLICATIONS

Matsumoto et al., "Role of Phosphatidylserine-Derived Negative Surface Charges in the Recognition and Uptake of Intravenously Injected B16BL6-Derived Exosomes by Macrophages", J Pharm Sci, 106 (2017) 168-175 (Year: 2017).*

Cohen et al., "From the Gla domain to a novel small-molecule detector of apoptosis", Cell Research (2009) 19:625-637 (Year: 2009).*

Aaronson et al., "A Road Map for Those Who Don't Know JAK-STAT," Science, 296(5):1653-1655, 2002.

(Continued)

*Primary Examiner* — Julie Ha
(74) *Attorney, Agent, or Firm* — Parker Highlander PLLC

(57) ABSTRACT

A method of targeting extracellular vesicles employing a molecule comprising a GLA domain and extracellular vesicles obtained or obtainable from a method are described herein.

26 Claims, 23 Drawing Sheets

Specification includes a Sequence Listing.

(56) References Cited

U.S. PATENT DOCUMENTS

| | | | |
|---|---|---|---|
| 6,312,694 | B1 | 11/2001 | Thorpe et al. |
| 6,459,996 | B1 | 10/2002 | Somers et al. |
| 6,631,332 | B2 | 10/2003 | Skolnick et al. |
| 6,801,860 | B1 | 10/2004 | Dessen et al. |
| 7,511,016 | B2 | 3/2009 | Reutelingsperger |
| 8,283,167 | B2 | 10/2012 | Simon |
| 8,519,103 | B2 * | 8/2013 | Madison ............... C12N 9/6437 530/384 |
| 9,023,604 | B2 | 5/2015 | Schmidt et al. |
| 9,694,048 | B2 * | 7/2017 | Bauzon ................... A61P 13/12 |
| 10,894,075 | B2 * | 1/2021 | Bauzon ................... A61P 25/00 |
| 2003/0104578 | A1 | 6/2003 | Balance |
| 2003/0220490 | A1 | 11/2003 | Kuriyama et al. |
| 2004/0001827 | A1 | 1/2004 | Dennis |
| 2005/0015232 | A1 | 1/2005 | Reinherz et al. |
| 2009/0098103 | A1 | 4/2009 | Madison et al. |
| 2009/0130060 | A1 | 5/2009 | Weimer et al. |
| 2011/0159571 | A1 | 6/2011 | Barry et al. |
| 2016/0008482 | A1 | 1/2016 | Bauzon et al. |
| 2017/0224840 | A1 | 8/2017 | Yao et al. |

FOREIGN PATENT DOCUMENTS

| | | |
|---|---|---|
| CN | 105567642 | 5/2016 |
| CN | 106414503 | 2/2017 |
| EP | 2280024 | 2/2011 |
| JP | 2002-003407 | 1/2002 |
| JP | 2011-515075 | 5/2011 |
| RU | 2373282 | 11/2009 |
| WO | WO 2005/079766 | 9/2005 |
| WO | WO2006/031291 | 3/2006 |
| WO | WO 2006/079120 | 7/2006 |
| WO | WO 2010/006136 | 1/2010 |
| WO | WO 2010/037402 | 4/2010 |
| WO | WO 2010/151736 | 12/2010 |
| WO | WO 2011/094181 | 8/2011 |
| WO | WO 2012/087241 | 6/2012 |
| WO | WO 2012/120130 | 9/2012 |
| WO | WO2013/011011 | 1/2013 |
| WO | WO 2013/151665 | 11/2013 |
| WO | WO 2014/018535 | 1/2014 |
| WO | WO 2014/151535 | 3/2014 |
| WO | WO 2014/151683 | 9/2014 |
| WO | WO2015/138452 | 9/2015 |
| WO | WO 2017/118764 | 7/2017 |
| WO | WO 2019/050997 | 3/2019 |
| WO | WO 2019/050998 | 3/2019 |
| WO | WO 2019/051002 | 3/2019 |

OTHER PUBLICATIONS

Abe et al., "Structural Analysis of the DF3 Human Breast Carcinoma-associated Protein," Cancer Research, 49(11):2834-2839, 1989.

Agata et al., "MUC1 Oncoprotein Blocks Death Receptor-Mediated Apoptosis by Inhibiting Recruitment of Caspase-8," Cancer Research, 68(15):6136-6144, 2008.

Ahmad et al., "MUC1 oncoprotein activates the IκB kinase ß complex and constitutive NF-κB signalling," Nature Cell Biology, 9(12):1419-1427, 2007.

Ahmad et al., "Triterpenoid CDDO-Me Blocks the Nf-κb Pathway by Direct Inhibition of IKKß on Cys-179," The Journal of Biological Chemistry, 281(4):35764-35769, 2006.

Ahmad et al., "Triterpenoid CDDO-Methyl Ester Inhibits the Janus-Activated Kinase-1 (JAK1)-->Signal Transducer and Activator of Transcription-3 (STAT3) Pathway by Direct Inhibition of JAK1 and STAT3," Cancer Research, 68(8):2920-2926, 2008.

Alvarez et al., "Identification of a Genetic Signature of Activated Signal Transducer and Activator of Transcription 3 in Human Tumors," Cancer Research, 65(12):5054-5062, 2005.

Alvarez et al., "Signal Transducer and Activator of Transcription 3 Is Required for the Oncogenic Effects of Non—Small-Cell Lung Cancer—Associated Mutations of the Epidermal Growth Factor Receptor," Cancer Research, 66(6):3162-3168, 2006.

Anderson et al., "Perspective— FcRn transports albumin: relevance to immunology and medicine," Trends in Immunology, 27(7):343-348, 2006.

Ashkenazi et al., "Immunoadhesins as research tools and therapeutic agents," Current Opinion in Immunology, 9:195-200, 1997.

Atoda et al., "Coagulation Factor X-Binding Protein from Deinagkistrodon acutus Venom Is a Gia Domain-Binding Protein," Biochemistry, vol. 37 (50), pp. 17361-17370, Nov. 25, 1998.

Baldus et al., "MUC1 and Nuclear ß-Catenin Are Coexpressed at the Invasion Front of Colorectal Carcinomas and Are Both Correlated with Tumor Prognosis," Clinical Cancer Research, 10(8):2790-2796, 2004.

Blankenberg, "Imaging the molecular signatures of apoptosis and injury with radiolabeled annexin V," Proceedings of the American Thoracic Society, vol. 6 (5), pp. 469-476, Aug. 15, 2009.

Bodanszky et al., "High Resolution Mass Spectra of Malformin and Related Cyclic Peptides," The Journal of Antibiotics, 29(5):549-553, 1976.

Boersma et al., "Past, Present, and Future of Annexin A5: From Protein Discovery to Clinical Applications," The Journal of Nuclear Medicine, 46(12):2035-2050, 2005.

Bowman et al., "STATs in oncogenesis," Oncogene, 19(21):2474-2488, 2000.

Brachert et al., "Compartmentalization of TNF Receptor 1 Signaling: Internalized TNF Receptosomes as Death Signaling Vesicles," Immunity, 21(3), pp. 415-428, 2004.

Bromberg et al., "Stat3 as an Oncogene," Cell, 98(3):295-303, 1999.

Buerger et al., "Sequence-specific Peptide Aptamers, Interacting with the Intracellular Domain of the Epidermal Growth Factor Receptor, Interfere with Stat3 Activation and Inhibit the Growth of Tumor Cells," The Journal of Biological Chemistry, 278(39):37610-37621, 2003.

Carter, "Potent antibody therapeutics by design," Nature Reviews Immunology, 6:343-357, 2006.

Chapman, "PEGylated antibodies and antibody fragments for improved therapy: a review," Advanced Drug Delivery Reviews, 54:531-545, 2002.

Chase, "Medical Applications of Radioisotopes," Remington's Pharmaceutical Sciences, 15th Ed., Mack Publishing Company, Easton, PA, Chapter 33, pp. 624-652, 1990.

Chaudhury et al., "The Major Histocompatibility Complex—related Fc Receptor for IgG (FcRn) Binds Albumin and Prolongs Its Lifespan," The Journal of Experimental Medicine, 197(3):315-322, 2003.

Chen et al., "Shaping the Nuclear Action of NF-κB," Nature Reviews Molecular Cell Biology, 5:392-401, 2004.

Cohen et al., "From the Gla domain to a novel small-molecule detector of apoptosis," Cell Research, vol. 19(5), pp. 625-637, May 1, 2009.

Cohen et al., "Molecular Modeling Software and Methods for Medicinal Chemistry," Journal of Medicinal Chemistry, 33(3):883-894, 1990.

Dosio et al., "Immunotoxins and Anticancer Drug Conjugates Assemblies: The Role of the Linkage between Components," Toxins, 3:848-883, 2011.

Duraisamy et al., "Distinct evolution of the human carcinoma-associated transmembrane mucins, MUC1, MUC4 and MUC16," Gene, 373:28-34, 2006.

Duttaroy et al., "Development of a Long-Acting Insulin Using Albumin Fusion Technology," Diabetes, 54:251-258, 2005.

Elliott et al., "Clearance of apoptotic cells: implications in health and disease," The Journal of Cell Biology, 189(7):1059-1070, 2010.

Elliott et al., "Enhancement of therapeutic protein in vivo activities through glycoengineering," Nature Biotechnology, 21:414-421, 2003.

Elliott et al., "Nucleotides released by apoptotic cells act as a find-me signal to promote phagocytic clearance," Nature, 461:282-286, 2009.

Erwig et al., "Clearance of apoptotic cells by phagocytes," Cell Death and Differentiation, 15:243-250, 2008.

Extended European Search Report issued in European Patent Application No. 14770639.4, dated Jul. 28, 2016.

(56) References Cited

OTHER PUBLICATIONS

Extended European Search Report issued in European Patent Application No. 14769812.0, dated Aug. 1, 2016.
Fischer, "Cellular Uptake Mechanisms and Potential Therapeutic Utility of Peptidic Cell Delivery Vectors: Progress 2001-2006," Medicinal Research Reviews, 27(6):755-795, 2007.
Franklin, "Enzymes," Remington's Pharmaceutical Sciences, 18th Ed., Mack Publishing Company, Easton, PA, Chapter 52, pp. 1035-1038, 1990.
Gaemers et al., "A STAT-responsive Element in the Promoter of the Episialin/MUC1 Gene Is Involved in Its Overexpression in Carcinoma Cells," The Journal of Biological Chemistry, 276(9):6191-6199, 2001.
Gendler et al., "A Highly Immunogenic Region of a Human Polymorphic Epithelial Mucin Expressed by Carcinomas Is Made Up of Tandem Repeats," The Journal of Biological Chemistry, 263(26):12820-12823, 1988.
Germain et al., "Targeting the Cytoplasmic and Nuclear Functions of Signal Transducers and Activators of Transcription 3 for Cancer Therapy," Clinical Cancer Research, 13(19):5665-5669, 2007.
Gerondakis et al., "Unravelling the complexities of the NF-κB signalling pathway using mouse knockout and transgenic models," Oncogene, 25:6781-6799, 2006.
Ghetie et al., "Increasing the Serum Persistence of an IgG Fragment by Random Mutagenesis," Nature Biotechnology, 15:637-640, 1997.
Ghosh et al., "NF-Kappa B and Rel Proteins: Evolutionarily Conserved Mediators of Immune Responses," Annual Review of Immunology, 16:225-260, 1998.
Ghosh et al., "Rapid isolation of extracellular vesicles from cell culture and biological fluids using a synthetic peptide with specific affinity for heat shock proteins," PLoS ONE, 9(10):e110443, 2014.
Grillot et al., "Genomic Organizaiton, Promoter Region Analysis, and Chromosome Localization of the Mouse Bc1-X Gene," The Journal of Immunology, 158(10):4750-4757, 1997.
Gronenborn et al., "Protein Structure Determination in Solution by Two-Dimensional and Three-Dimensional Nuclear Magnetic Resonance Spectroscopy," Analytical Chemistry, 62(1):2-15, 1990.
Hansson and Stenflo, "Post-translational modifications in proteins involved in blood coagulation," J. Thrombosis Haemostasis, 3(12):2633-2648, 2005.
Hayden et al., "Shared Principles in NF-Kappab Signaling," Cell, 132(3):344-362, 2008.
Hinton et al., "An Engineered Human IgG1 Antibody with Longer Serum Half-Life," Immunology, 176(1):346-356, 2006.
Hodel et al., "The Three-Dimensional Structure of the Autoproteolytic, Nuclear Pore-Targeting Domain of the Human Nucleoporin Nup98," Molecular Cell, (2):347-358, 2002.
Hoffmann et al., "Transcriptional Regulation via the NF-KappaB Signaling Module," Oncogene, 25(51):6706-671, 2006.
Huang et al., "MUC1 Cytoplasmic Domain Coactivates Wnt Target Gene Transcription and Confers Transformation," Cancer Biology & Therapy, 2(6):702-706, 2003.
Huang et al., "MUC1 Oncoprotein Blocks Glycogen Synthase Kinase 3beta-Mediated Phosphorylation and Degradation of Beta-Catenin," Cancer Research, 65(22):10413-10422, 2005.
Huang et al., "Structural basis of membrane binding by Gla domains of vitamin K-dependent proteins," Nature Structural Biology, vol. 10 (9), pp. 751-756, 2003.
Huxford et al., "The Crystal Structure of the IkappaBalpha/NF-KappaB Complex Reveals Mechanisms of NFKappaB Inactivation," Cell, vol. 95 (6), pp. 759-770, Dec. 11, 1998.
Jackson, "Contributions of Protein Structure-Based Drug Design to Cancer Chemotherapy," Seminars in Oncology, vol. 24 (2), pp. 164-172, Apr. 1997.
Jacobs et al., "Membrane Binding Properties of the Factor IX γ-Carboxyglutamic Acid-rich Domain Prepared by Chemical Synthesis", The Journal of Biological Chemistry, vol. 269 (41), 25494-25501, Oct. 14, 1994.
Jacobs et al., "Structure of an IkappaBalpha/NF-KappaB Complex," Cell, vol. 95 (6), pp. 749-758, Dec. 11, 1998.

Jain et al., "Engineering Antibodies for Clinical Applications," Trends in Biotechnology, vol. 25 (7), pp. 307-316, Jul. 2007.
Johnson et al., "Peptide Turn Mimetics," In: Biotechnology and Pharmacy, Chapter 14, Pezzuto J.M., et al., (Eds..), Springer Science+Business Media Dordrecht, NY, pp. 366-378, 1993.
Jones et al., "Structure-Based Design of Lipophilic Quinazoline Inhibitors of Thymidylate Synthase," Medicinal Chemistry, vol. 39 (4), pp. 904-917, Feb. 16, 1996.
Karin et al., "NF-kappaB at the Crossroads of Life and Death," Nature Immunology, vol. 3 (3), pp. 221-227, Mar. 2002.
Kau et al., "Nuclear Transport and Cancer: From Mechanism to Intervention," Nature Reviews Cancer, vol. 4 (2), pp. 106-117, Feb. 2004.
Kawano et al., "MUC1 Oncoprotein Regulates Bcr-Abl Stability and Pathogenesis in Chronic Myelogenous Leukemia Cells," Cancer Research, vol. 67 (24), pp. 11576-11584, Dec. 15, 2007.
Kenis et al., "Cell surface-expressed phosphatidylserine and annexin A5 open a novel portal of cell entry," J. Biol. Chemistry, 279(50):52623-52629, 2004.
Keyt et al., "A Faster-Acting and More Potent Form of Tissue Plasminogen Activator," Proceedings of the National Academy of Sciences, vol. 91 (9), pp. 3670-3674, Apr. 1994.
Kietselaer et al., "Molecular Imaging of Cell Death in Intracardiac Tumours: A New Approach to Differential Diagnosis in Cardiac Tumours," Netherlands Heart, vol. 10 (7-8), pp. 313-317, Aug. 2002.
Kinlough et al., "MUC1 Membrane Trafficking is Modulated by Multiple Interactions," Biological Chemistry, vol. 279 (51), pp. 53071-53077, Dec. 17, 2004.
Kufe et al., "Differential Reactivity of a Novel Monoclonal Antibody (DF3) with Human Malignant Versus Benign Breast Tumors," Hybridoma, vol. 3 (3), pp. 223-232, 1984.
Kurihara et al., "Imaging and Dosimetry of 99mTc EC Annexin V: Preliminary Clinical Study Targeting Apoptosis in Breast Tumors," Applied Radiation and Isotopes, vol. 66 (9), pp. 1175-1182, 2008.
Lahorte et al., "Apoptosis-Detecting Radioligands: Current State of the Art and Future Perspectives," European Journal of Nuclear Medicine and Molecular Imaging, vol. 31 (6), pp. 887-919, Jun. 2004.
Lee et al., "Persistently Activated Stat3 Maintains Constitutive NF-kappab Activity in Tumors," Cancer Cell, vol. 15 (4), pp. 283-293, Apr. 7, 2009.
Lemke, "Phosphatidyleserine is the signal for TAM receptors and their ligands," Trends in Biochemical Sciences, 42(9):738-748, 2017.
Leng, et al., "Nuclear Import of the MUC1-C Oncoprotein is Mediated by Nucleoporin Nup62," Biological Chemistry, vol. 282 (27), pp. 19321-19330, Jul. 6, 2007.
Levitin et al., "MUC1 SES Module is a Self-Cleaving Domain," Biological Chemistry, vol. 380 (39), pp. 3337 4-33386, Sep. 30, 2005.
Levy et al., "Cellulose-Binding Domains: Biotechnological Applications," Biotechnology Advances, vol. 20 (3-4), pp. 191-213, Nov. 2002.
Li et al., "DF3/MUC1 Signaling in Multiple Myeloma Cells Is Regulated by Interleukin-7," Cancer Biology & Therapy, vol. 2 (2), pp. 187-193, Mar.-Apr. 2003.
Li et al., "Heregulin Targets Gamma-Catenin to the Nucleolus by a Mechanism Dependent on the DF3/MUC1 Oncoprotein," Molecular Cancer Research, vol. 1 (10), pp. 765-775, Aug. 2003.
Li et al., "Human DF3/MUC1 Carcinoma-Associated Protein Functions as an Oncogene," Sep. 4, 2003.
Li et al., "Interaction of Glycogen Synthase Kinase 3beta with the DF3/MUC1 Carcinoma-Associated Antigen and Bela-Catenin," Molecular and Cellular Biology, vol. 18, (12), pp. 7216-7224, Dec. 1998.
Li et al., "The c-Src Tyrosine Kinase Regulates Signaling of the Human DF3/MUC1 Carcinoma-Associated Antigen with GSK3 Bela and Bela-Catenin," Biological Chemistry, vol. 276 (9), pp. 6061-6064, Mar. 2001.
Li et al., "The Epidermal Growth Factor Receptor Regulates Interaction of the Human DF3/MUC1 Carcinoma Antigen with C-Src and Bela-Catenin," Biological Chemistry, vol. 276 (38), pp. 35239-35242, Sep. 21, 2001.

(56) References Cited

OTHER PUBLICATIONS

Ligtenberg et al., "Cell-Associated Episialin Is a Complex Containing Two Proteins Derived From a Common Precursor," Biological Chemistry, vol. 267 (9), pp. 6171-6177, Mar. 25, 1992.
Lin et al., "Protein-Based Tumor Molecular Imaging Probes," Amino Acids, vol. 41 (5), pp. 1013-1036, Nov. 2011.
Loose et al., "123I-Interleukin-2 Uptake in Squamous Cell Carcinoma of the Head and Neck Carcinoma," European Journal of Nuclear Medicine and Molecular Imaging, vol. 35 (2), pp. 281-286, Feb. 2008.
Loose et al., "Prognostic Value of 99mTc-Hynic Annexin-V Imaging in Squamous Cell Carcinoma of the Head and Neck," European Journal of Nuclear Medicine and Molecular Imaging, vol. 35 (1), pp. 47-52, Jan. 2008.
Macao et al., "Autoproteolysis Coupled to Protein Folding in the SEA Domain of the Membrane-Bound MUC1 Mucin," Nature Structural & Molecular Biology, vol. 13 (1), pp. 71-76, Jan. 2006.
McPherson, "Crystallization of Proteins From Polyethylene Glycol," Biological Chemistry, vol. 251 (20), pp. 6300-6303, Oct. 25, 1976.
Melder et al., "Pharmacokinetics and In Vitro and In Vivo Anti-Tumor Response of an Interleukin-2-Human Serum Albumin Fusion Protein in Mice," Cancer Immunology, Immunotherapy, vol. 54 (6), pp. 535-547, Jun. 2005.
Merlo et al., "Frequent Alteration of the DF3 Tumor-Associated Antigen Gene in Primary Human Breast Carcinoms," Cancer Research, vol. 49 (24 Pt 1), pp. 6966-6971, Dec. 15, 1989.
Merrifield et al., "Solid Phase Peptide Synthesis. I. The Synthesis of a Tetrapeptide," American Chemical Society, vol. 85 (14), pp. 2149-2154, 1963.
Micheau et al., "Induction of TNF Receptor I-Mediated Apoptosis via Two Sequential Signaling Complexes," Cell, vol. 114 (2), pp. 181-190, Jul. 25, 2003.
Mille-Baker et al., "Deletion or replacement of the second EGF-like domain of protein S results in loss of APC cofactor activity," Blood, 101:1416-1418, 2003.
Mimura et al., "The Influence of Glycosylation on the Thermal Stability and Effector Function Expression of Human IgG1-Fc: Properties of a Series of Truncated Glycoforms," Molecular Immunology, vol. 37, (12-13), pp. 697-706, Aug.-Sep. 2000.
Muthuswamy et al., "ErbB2, but not ErbB1, Reinitiates Proliferation and Induces Luminal Repopulation in Epithelial Acini," Nature Cell Biology, vol. 3 (9), pp. 785-792, Sep. 2001
Nakai et al., "A novel affinity-based method for the isolation of highly purified extracellular vesicles," Scientific Reports, 6(1):1-2, 2016.
Naresh et al., "Apoptosis Index Is a Predictor of Metastatic Phenotype in Patients with Early Stage Squamous Carcinoma of the Tongue: A Hypothesis to Support this Paradoxical Association," Cancer, vol. 91 (3), pp. 578-584, Feb. 1, 2001.
Natoli et al., "Interactions of NF-kappaB with Chromatin: The Art of Being at the Right Place at the Right Time," Nature Immunology, vol. 6 (5), pp. 439-445, May 2005.
Navia et al., "Use of Structural Information in Drug Design," Current Opinion in Structural Biology, vol. 2, pp. 202-210, 1992.
Nelsestuen, "Enhancement of Vitamin-K-Dependent Protein Funcation by Modification of the Gamma-Carboxyblutamin Acid Domain: Studies of Protein C and factor VII," Trends in Cardiovascular Medicine, vol. 9(6), pp. 162-167, Aug. 1999.
Office Communication issued in Australian Patent Application No. 2014233885, dated Aug. 10, 2017.
Office Communication issued in Japanese Patent Application No. 2016-502002, dated Dec. 26, 2017. (English translation of Japanese text).
Office Communication issued in Japanese Patent Application No. 2016-502083, dated Feb. 20, 2018.
Office Communication issued in Russian Patent Application No. 2015144097, dated Dec. 15, 2017. (English translation of Russian text).
Office Communication issued in Singapore Patent Application No. 11201506307X, dated Oct. 3, 2017.
Office Communication issued in Singapore Patent Application No. 11201506880W, dated Dec. 28, 2017.
Office Communication issued in U.S. Appl. No. 14/772,971, dated Feb. 24, 2020.
Office Communication issued in U.S. Appl. No. 14/772,971, dated Aug. 9, 2019.
Office Communication issued in U.S. Appl. No. 14/772,971, dated Jan. 11, 2019.
Office Communication issued in U.S. Appl. No. 14/772,971, dated Jun. 29, 2018.
Office Communication issued in U.S. Appl. No. 14/772,971, dated Mar. 15, 2018.
Office Communication issued in U.S. Appl. No. 16/170,131, dated Feb. 27, 2020.
Office Communication issued in U.S. Appl. No. 16/170,131, dated Oct. 17, 2019.
Office Communication issued in U.S. Appl. No. 14/773,068, dated Nov. 29, 2016.
Office Communication issued in U.S. Appl. No. 14/773,068, dated Aug. 2, 2016.
Office Communication issued in U.S. Appl. No. 15/631,937, dated Jul. 25, 2018.
Office Communication issued in U.S. Appl. No. 15/631,937, dated Jan. 10, 2018.
Okada et al., "A novel splice site mutation in intron C of PROS1 leads to markedly reduced mutant mRNA level, absence of thrombin-sensitive region, and impaired secretion and cofactor activity of mutant protein S," Thrombosis Research, 125:e246-250, 2010.
Osborn et al., "Albutropin: A Growth Hormone-Albumin Fusion with Improved Pharmacokinetics and Dharmacodynamics in Rats and Monkeys," European Journla of Pharmacology, vol. 456 (1-3, pp. 149-158, Dec. 5, 2002.
Osborn et al., "Pharmacokinetic and Pharmacodynamic Studies of a Human Serum Albumin-Interferon-Alpha Fusion Protein in Cynomolgus Monkeys," Pharmacology and Experimental Therapeutics, vol. 303 (2), pp. 540-548, Nov. 2002.
Pasparakis et al., "Dissection of the NF-kappaB Signalling Cascade in Transgenic and Knockout Mice," Cell Death & Differentiation, vol. 13 (5), pp. 861-872, May 2006.
PCT International Preliminary Report on Patentability issued in International Application No. PCT/US2018/049618, dated Sep. 30, 2019.
PCT International Preliminary Report on Patentability issued in International Application No. PCT/US2018/049624, dated Jan. 10, 2010.
PCT International Search Report & Written Opinion issued in International Application No. PCT/US2014/026237, dated Aug. 29, 2014.
PCT International Search Report and Written Opinion issued in International Patent Application No. PCT/US2014/025940, dated Jun. 27, 2014.
PCT International Search Report and Written Opinion issued in International Application No. PCT/US2018/049618, dated Dec. 6, 2018.
PCT International Search Report and Written Opinion issued in International Application No. PCT/US2018/049624, dated Dec. 5, 2018.
PCT International Search Report and Written Opinion issued in International Application No. PCT/US2018/049619, dated Dec. 6, 2018.
Percipalle et al., "Molecular Interactions between the Importin Alpha/Beta Heterodimer and Proteins Involved in Vertebrate Nuclear Protein Import," Molecular Biology, vol. 266 (4), pp. 722-732, Mar. 7, 1997.
Perey et al., "Effects of Differentiating Agents on Cell Surface Expression of the Breast Carcinoma-Associated DF3-P Epitope," Cancer Research, vol. 52 (22), pp. 6365-6370, Nov. 15, 1992.
Petkova et al., "Enhanced Half-Life of Genetically Engineered Human lgG1 Antibodies in a Humanized FcRn Mouse Model:

(56) References Cited

OTHER PUBLICATIONS

Potential Application in Humorally Mediated Autoimmune Disease," International Immunology, vol. 18 (12), pp. 1759-1769, Dec. 2006.
Raina et al., "Direct Targeting of the Mucin 1 Oncoprotein Blocks Survival and Tumorigenicity of Human Breast Carcinoma Cells," Cancer Research, vol. 69 (12), pp. 5133-5141, Jun. 15, 2009.
Raina et al., "MUC1 Oncoprotein Blocks Nuclear Targeting of c-Abl in the apoptotic response to DNA damage," EMBO, 25:3774-3783, 2006.
Raina et al., "The MUC1 Oncoprotein Activates the Anti-Apoptotic Phosphoinositide 3-kinase/Akt and Bcl-XL Pathways in Rat 3y1 Fibroblasts," Biological Chemistry, vol. 279 (20), pp. 20607-20612, May 14, 2004.
Raju et al., "Fc Glycans Terminated with N-Acetylglucosamine Residues Increase Antibody Resistance to Dapain," Biotechnology Progress, vol. 23, pp. 964-971, 2007.
Raju et al., "Glycosylation in the Fe Domain of IgC Increases Resistance to Proteolytic Clevage by Papain," Biochemical and Biophysical Research Communications, vol. 341 (3), pp. 797-803, Mar. 17, 2006.
Ramasamy et al., "The MUC1 and Galectin-3 Oncoproteins Function in a MicroRNA-Dependent Regulatory Loop," Molecular Cell, vol. 27 (6), pp. 992-1004, Sep. 21, 2007.
Regan et al., "The Interaction between the Endothelial Cell Protein C Receptor and Protein C Is Dictated by the g-Carboxyglutamic Acid Domain of Protein C," The Journal of Biological Chemistry, vol. 272 (42), pp. 26279-26284, Oct. 17, 1976.
Ren et al., "Human MUC1 Carcinoma-Associated Protein Confers Resistance to Genotoxic Anticancer agents," Cancer Cell, vol. 5 (2), pp. 163-175, Feb. 2004.
Ren et al., "Protein kinase C Delta Regulates Function of the DF3/MUC1 Carcinoma Antigen in Beta-Catenin Signaling," Biological Chemistry, vol. 277 (20), pp. 17616-17622, May 17, 2002.
Reutelingsperger et al., "Visualization of Cell Death in Vivo with the Annexin A5 imaging protocol," Immunological Methods, vol. 265 (1-2), pp. 123-132, Jul. 1, 2002.
Ryan et al., "The Nuclear Pore Complex: A Protein Machine Bridging the Nucleus and Cytoplasm," Current Opinion in Cell Biology, vol. 12 (3), pp. 361-371, Jun. 2000.
Schroeder et al., "MUC1 Overexpression Results in Mammary Gland Tumorigenesis and Prolonged Alveolar Differentiation," Oncogene, vol. 23 (34), pp. 5739-5747, Jul. 29, 2004.
Schroeder et al., "Transgenic MUC1 Interacts with Epidermal Growth Factor Receptor and Correlates with Mitogen-activated Protein Kinase Activation in the Mouse Mammary Gland," Biological Chemistry, vol. 276 (16), pp. 13057-13064, Apr. 20, 2001.
Schutters et al., "Phosphatidylserine targeting for diagnosis and treatment of human diseases," Apoptosis, vol. 15 (9), pp. 1072-1082, May 4, 2010.
Shah et al., "Manipulation of the Membrane Binding Site of Vitamin K-Dependent Proteins: Enhanced Biological Function Human Factor VII," Proceedings of the National Academy of Sciences, vol. 95 (8), pp. 4229-4234, Apr. 14, 1998.
Shuai et al., "Modulation of STAT Signaling by STAT-Interacting Proteins," Oncogene, vol. 19 (21), pp. 2638-2644, May 15, 2000.
Siddiquee et al., "Isolation and Sequencing of a CDNA Coding for the Human DF3 Breast Carcinoma-Associate Antigen," Proceedings of the National Academy of Sciences, vol. 85(7), pp. 2320-2323, Apr. 1988.
Siddiquee et al., "Selective Chemical Probe Inhibitor of Stat3, Identified Through Structure-Based Virtual Screening, Induces Antitumor Activity," Proceedings of the National Academy of Sciences, vol. 104 (18) pp. 7391-7396, May 1, 2007.
Sinclair et al., "Glycoengineering: The Effect of Glycosylation on the Properties of Therapeutic Proteins," Pharmaceutical Sciences, vol. 94 (8), pp. 1626-1635, Aug. 2005.
Soares et al., "Targeting Inside-Out Phosphatidylserine as a Therapeutic Strategy for Viral Diseases," Nat. Med., 14(12):1357-1362, 2008.

Song et al., "A Low-Molecular-Weight Compound Discovered Through Virtual Database Screening Inhibits stat3 Function in Breast Cancer Cells," Proceedings of the National Academy of Sciences, vol. 102 (13), pp. 4700-4705, Mar. 29, 2005.
Soule et al., "Isolation and Characterization of a Spontaneously Immortalized Human Breast Epithelial Cell Line, MCF-10," Cancer Research, vol. 50 (18), pp. 6075-6086, Sep. 15, 1990.
Srivastava et al., "Localization of phosphatidylserine binding sites to structural domains of factor Xa," The Journal of Biological Chemistry, 277(3):1855-1863, 2002.
Stenflo, "Contributions of Gla and EGF-like domains to the function of vitamin K-dependent coagulation factors," Critical Reviews in Eukaryotic Gene Expression, 9(1):59-88, 1999.
Suh et al., "Translocation of B Catenin into the Nucleus Independent of Interactions with FG-Rich Nucleoporins," Experimental Cell Research, vol. 290, pp. 447-456, 2003.
Sung et al., "An IFN-Beta-Albumin Fusion Protein That Displays Improved Pharmacokinetic and Dharmacodynamic Properties in Nonhuman Primates," Interferon and Cytokine Research, vol. 23 (1), pp. 25-36, Jan. 2003.
Tait et al., "Phospholipid Binding of Annexin V: Effects of Calcium and Membrane Phosphatidylserine Content," Archives of Biochemistry and Biophysics, vol. 298 (1), pp. 187-191, Oct. 1992.
Tietjen et al., "Molecular mechanism for differential recognition of membane phosphtidylserine by the immune regulatory receptor Tim4," PNAS, 111(15):E1463-E1472, 2014.
Truscott et al., "A J-Protein Is an Essential Subunit of the Presequence Translocase-Associated Protein Import Motor of Mitochondria," The Journal of Cell Biology, vol. 163 (4), pp. 707-713, Nov. 24, 2003.
Turco, "Intravenous Admixtures", Mack Publishing Company, Easton, PA, Chapter 85, 1570-1580, 1990.
Umana et al., "Engineered Glycoforms of an Ant Neuroblastoma IgG1 with Optimized Antibody-Dependent Cellular Cytotoxic Activity," Nature Biotechnology, vol. 17 (2), pp. 176-180, Feb. 1999.
Vaccaro et al., "Engineering the Fc Region of Immunoglobulin G to Modulate in Vivo Antibody Levels," Nature Biotechnology, vol. 23 (10), pp. 1283-1288, Oct. 2005.
Van Den Eijnde et al., "Transient Expression of Phosphatidylserine at Cell-Cell Contact Areas is required for Myotube Formation," Journal of Cell Science, vol. 114 (P1 20), pp. 3631-3642, Oct. 2001.
Van Wijnen et al., "Characterization of mini-protein S, a recomvinant variant of protein S that lacks the sex hormone binding globulin-like domain," Biochem. J., 330:389-396, 1998.
Vermeer et al., "Segregation of Receptor and Ligand Regulates Activation of Epithelial Growth Factor Receptor," Nature, vol. 422 (6929), pp. 322-326, Mar. 20, 2003.
Veronese et al., "PEGylalion, Successful Approach to Drug Delivery," Drug Discovery Today, vol. 10 (21), pp. 1451-1458, Nov. 1, 2005.
Webb et al., "Vitamin K-Dependent Protein S Localizing complement Regulatro C4b-Binding Protein to the Surface of Apoptotic Cells," The Journal of Immunology, vol. 169 (5), pp. 2580-2586, Sep. 1, 2002.
Weber, "Physical Principles of Protein Crystallization," Advances in Protein Chemistry, vol. 41, pp. 1-36, 1991.
Wegenka et al., "The lnlerleukin-6-Activated Acute-Phase Response Factor is Antigenically and Functionally Related to Members of the Signal Transducer and Activator of Transcription (STAT) family," Molecular and Cellular Biology, vol. 14 (5), pp. 3186-3196, May 1994.
Wei et al., Human MUC1 Oncoprotein regulates p53-Responsive Gene Transcription in the Cell, vol. 7 (2), pp. 167-178, Feb. 2005.
Wei et al., "Human Mucin 1 Oncoprotein Represses Transcription of the p53 Tumor Suppressor Gene," Cancer Research, vol. 67 (4), pp. 1853-1858, Feb. 15, 2007.
Wei et al., "MUC1 Oncoprotein Stabilizes and Activates Estrogen Receptor Alpha," Molecular Cell, vol. 21 (2), pp. 295-305, Jan. 20, 2006.
Weis, "Regulating Access to the Genome: Nucleocytoplasmic Transport throughout the Cell Cycle," Cell, vol. 112 (4), pp. 441-451, Feb. 21, 2003.

(56) References Cited

OTHER PUBLICATIONS

Wen et al., "Nuclear Association of the Cytoplasmic Tail of MUC1 and Beta-Catenin," The Journal of Biological Chemistry, vol. 278 (39), pp. 38029-38039, Sep. 26, 2003.

Wider, "Structure Determination of Biological Macromolecules in Solution Using Nuclear Magnetic Resonance Spectroscopy," Biotechniques, vol. 29 (6), pp. 1278-1294, Dec. 2000.

Yamamoto et al., "Interaction of the DF3/MUC1 Breast Carcinoma-Associated Antigen and Beta-Catenin in Cell Adhesion," The Journal of Biological Chemistry, vol. 272 (19), pp. 12492-12494, May 9, 1997.

Yeh et al., "Design of Yeast-Secreted Albumin Derivatives for Human Therapy: Biological and Antiviral Properties of a Serum Albumin-CD4 Genetic Conjugate," Proceedings of the National Academy of Sciences, USA, vol. 89 (5), pp. 1904-1908, Mar. 1, 1992.

Yin et al., "Human MUC1 Carcinoma Antigen Regulates Intracellular Oxidant Levels and the Apototic Response of Oxidative Stress," The Journal of Biological Chemistry, vol. 278 (37), pp. 35458-35464, Sep. 12, 2003.

Yin et al., "MUC1 Oncoprotein Activates the FOX03a Transcription Factor in a Survival Response to Oxidative Stress," The Journal of Biological Chemistry, vol. 279 (44), pp. 45721-45727, Oct. 29, 2004.

Yin et al., "Mucin 1 Oncoprotein Blocks Hypoxia-Inducible Factor 1alpha Activation in a Survival Response to Hypoxia," The Journal of Biological Chemistry, vol. 282 (1), pp. 257-266, Jan. 5, 2007.

Young et al., "Molecular Chaperones Hsp90 and Hsp70 Deliver Preproteins to the Mitochondrial Import Receptor Tom70," Cell, vol. 112 (1), pp. 41-50, Jan. 10, 2003.

Yu et al., "Oncogenes as Regulators of tissue Factor Expression in Cancer: Implications for Tumor Angiogenesis and Anti-Cancer," Seminars in Thrombosis and Hemostasis, vol. 30 (1), pp. 21-30, Feb. 2004.

Yu et al., "The STATs of Cancer—New Molecular Targets Come of Age," Nature Reviews Cancer, vol. 4 (2), pp. 97-105, Feb. 2004.

Zhang et al., "Interacting Regions in Stat3 and c-Jun that Participate in Cooperative Transcriptional Activation," Molecular and Cellular Biology, vol. 19 (10), pp. 7138-7146, Oct. 1999.

Yokoyama et al., "Immunohistochemical Detection of Phosphatidylserine and Thrombospondin on Denucleating Erythroblasts in Rat Bone Marrow", *J. Vet. Med. Sci.*, 43:949-952, 2011.

English translation of Office Communication issued in Japanese Patent Application No. 2019-176325, dated Aug. 28, 2020.

GenBank Accession No. AAH15801, "PROS1 protein [Homo sapiens]," Aug. 11, 2006.

McDonald et al., "Ionic properties of membrane association by vitamin K-dependent proteins: The case for univalency," *Biochemistry*, 36:15589-15598, 1997.

Office Communication issued in New Zealand Patent Application No. 712058, dated Sep. 9, 2020.

Office Communication issued in New Zealand Patent Application No. 751491, dated Sep. 8, 2020.

Amara and Mercer, "Viral apoptotic mimicry," Nature Reviews Microbiology, 13(8)461-9, 2015.

Andaloussi et al., "Extracellular vesicles: Biology and emerging therapeutic opportunities," Nature Reviews Drug Discovery, 12(5):347-357, 2013.

Beck et al., "Strategies and challenges for the next generation of antibody-drug conjugates," Nature Reviews Drug Discovery, 16(5):315-337, 2017.

Belhocine et al., "99mTc-Annexin A5 quantification of apoptotic tumor response: a systematic review and meta-analysis of clinical imaging trials," European Journal of Nuclear Medicine and Molecular Imaging, 42(13):2083-2097, 2015.

Belzile et al., "Antibody targeting of phosphatidylserine for the detection and immunotherapy of cancer,"ImmunoTargets and Therapy, 7:1014, 2018.

Benabdellah et al, "Genome-edited adult stem cells: Next-generation advanced therapy medicinal products," Stem Cells Translational Medicine, 9(6):674-685, 2020.

Birge et al., "Phosphatidylserine is a global immunosuppressive signal in efferocytosis, infectious disease, and cancer," Cell Death and Differentiation, 23(6):962-978, 2016.

Burstyn-Cohen and Maimon, "TAM receptors, phosphatidylserine, inflammation and cancer," Cell Communication and Signaling, 17(1):156, 2019.

Calianese and Birge, "Biology of phosphatidylserine (PS): basic physiology and implications in immunology, infectious disease and cancer," Communication and Signaling, 18(1):41, 2020.

Colombo et al., "Biogenesis, Secretion, and Intercellular Interactions of Exosomes and Other Extracellular Vesicles," Annual Review of Cell and Developmental Biology, 30(1):255-289, 2014.

Conlan, "Early pathogenesis of Listeria monocytogenes infection in the mouse spleen," Journal of Medical Microbiology, 44(4):295-302, 1996.

Crescitelli et al., "Distinct RNA profiles in subpopulations of extracellular vesicles: Apoptotic bodies, microvesicles and exosomes," Journal of Extracellular Vesicles, 2(1):2013.

Dahlbäck., "The tale of protein S and C4b-binding protein, a story of affection," Thrombosis and Haemostasis, 98(1):756-764, 2007.

Dayoub and Brekken, "TIMS, TAMS, and PS-antibody targeting: implications for cancer immunotherapy," Cell Communication and Signaling, 18(1):29, 2020.

Derose et al., "Development of bavituximab, a vascular targeting agent with immune-modulating properties, for lung cancer treatment," Immunotherapy, 3(8):933-944, 2011.

Elmore et al., "Apoptosis: A Review of Programmed Cell Death," Toxicol. Pathol., 29(6):997-1003, 2007.

Gerber et al., "Randomized phase III study of docetaxel plus bavituximab in previously treated advanced non-squamous non-small-cell lung cancer," Annals of Oncology, 29(7):1548-1553, 2018.

Graca and Willem, "Extracellular vesicles: exosomes, microvesicles, and friends," Journal of Cell Biology, 200(4):373-383, 2013.

Graner et al. "Tumor-derived exosomes, microRNAs, and cancer immune suppression," Seminars in Immunopathology, 40(5):505-515, 2018.

Hemberger et al., "Trophoblast stem cells differentiate in vitro into invasive trophoblast giant cells," Developmental Biology, 271:362-371, 2004.

Hoen et al., "Extracellular vesicles and viruses: Are they close relatives?" Proceedings of the National Academy of Sciences of the United States of America, 113(33):9155-9161, 2016.

Huang and Lai, "The potential roles of stem cell-derived extracellular vesicles as a therapeutic tool," Annals of Translational Medicine, 7(22):693, 2019.

Kanada et al., "Signaling by Extracellular Vesicles Advances Cancer Hallmarks," Trends in Cancer, 2(2):84-94, 2018.

Li et al., "Targeting phosphatidylserine with calcium-dependent protein-drug conjugates for the treatment of cancer," Molecular Cancer Therapeutics, 17(2):169-182, 2018.

Mann et al., "Surface-dependent reactions of the vitamin K-dependent enzyme complexes," Journal of American Society of Hematology, 76:1-16, 1990.

Murphy et al., "Extracellular vesicle-based therapeutics: natural versus engineered targeting and trafficking," Experimental and Molecular Medicine, 51(3):1-12, 2019.

N'Guessan et al., "SapC-Dops—a phosphatidylserine-targeted nanovesicle for selective cancer therapy," Cell Communication and Signaling, 18(6):2020.

Oguro et al., "SLAM family markers resolve functionally distinct subpopulations of hematopoietic stem cells and multipotent progenitors,"Cell Stem Cell, 13:102-116, 2013.

Oling et al., "Trimers, dimers of trimers, and trimers of trimers are common building blocks of annexin A5 two-dimensional crystals," Journal of Structural Biology, 133(1):55-63, 2001.

Rezende et al., Coagulation, inflammation, and apoptosis: Different roles for protein S and the protein S-C4b binding protein comples, Blood, 103(4):1192-1201, 2004.

(56) References Cited

OTHER PUBLICATIONS

Schorey et al., "Exosomes and other extracellular vesicles in host—pathogen interactions," EMBO Reports, 16(1):24-43, 2015.
Shelke et al., "Importance of exosome depletion protocols to eliminate functional and RNA-containing extracellular vesicles from fetal bovine serum," Journal of Extracellular Vesicles, 3(1):2014.
Shlomovitz et al., "Flipping the dogma—phosphatidylserine in non-apoptotic cell death," Cell Communication and Signaling, 17(1):139, 2019.
Suzuki et al., "Xk-related protein 8 and Ced-8 promote phosphtidylserine exposure in apoptotic cells," Science, 341(6144):403-406, 2013.
Valadi et al., "Exosome-mediated transfer of mRNAs and microRNAs is a novel mechanism of genetic exchange between cells," Nature Cell Biology, 9(6):654-659, 2007.
Vaupel and Multhoff, "Accomplices of hypoxic tumor microenvironment compromising antitumor immunity: adenosine, lactate, acidosis, vascular endothelial growth factor, potassium ions and phosphatidylserine," Frontiers in Immunology, 8:1887, 2017.
Vermeer, "γ-Carboxyglutamate-containing proteins and the vitamin K-dependent carboxylase," Biochemical Journal, 266:625-636, 1990.
Wanderley et al., "Apoptotic mimicry as a strategy for the establishment of parasitic infections: parasite- and host-derived phosphtidylersine as key molecule," Cell Communication and Signaling, 18:10(1), 2020.
Wang et al. "SPECT and PET radiopharmaceuticals for molecular imaging of apoptosis: From bench to clinic," Oncotarget, 8(12):20479-20495, 2017.
Yáñez-Móet al. "Biological properties of extracellular vesicles and their physiological functions," Journal of Extracellular Vesicles, 14(4):2015.
Bhandari et al., "REX-1 expression and p38 MAPK activation status can determine proliferation/differentiation fates in human mesenchymal stem cells", PLoS One, 2010, vol. 5(5):e10493, 2010.
Guan et al., "Multiparameter characterization confirms apoptosis as the primary cause of reduced self-renewal capacity in cultured human fetal neural stem cells", *Cellular Physiology and Biochemistry*, 38(6):2123-2138, 2016.
Sebastian et al., Centrifugal countercurrent chromatography to elucidate surface differences of adipose tissue-derived stem cells, *Journal of Separation Science*, 35(10-11)1388-1398, 2012.
Office Communication issued in Korean Patent Application No. 10-2020-7005896, dated Oct. 19, 2023. English Translation.
Office Communication issued in Korean Patent Application No. 10-2020-700278, dated Oct. 19, 2023. English Translation.
Skotland et al., "Lipids in exosomes: Current Knowledge and the way forward", *Progress in Lipid Research*, 66:30-41, 2017.
Wang et al., "Structural Transitions of the RING1B C-Terminal Region upon Binding the Polycomb cbox Domain", *Biochemistry*, 47(31):8007-8015, 2008.
Xu et al., "Phosphatidylserine enhances osteogenic differentiation in human mesenchymal stem cells via ERK signal pathways", *Materials Science and Engineering*, 33:1783-1788, 2013.
Hardy et al., "Gla-domain mediated targeting of externalized phosphatidylserine for intracellular delivery," FASEB J., 37(8), 2023.
Lai et al., "*MSC secretes at least 3 EV types each with a unique permutation of membrane lipid, protein and RNA,* " Journal of extracellular vesicles, 5:29828, 2016.
Liang et al., "*Development of a magnetic bead-based method for the collection of circulating extracellular vesicles,*" New Biotechnology, vol. 33, Issue No. 1: 116-122, 2016.
Zhu et al., "*Hypoxia and serum deprivation-induced apoptosis in mesenchymal stem cells,* " Stem cells 24: 416-425, 2006.

\* cited by examiner

Figure 1E  An embodiment of a GLA-component

METHOD OF TARGETING EXOSOMES

CROSS-REFERENCE TO RELATED APPLICATIONS

This application is a national phase application under 35 U.S.C. § 371 of International Application No. PCT/US2018/049619, filed Sep. 5, 2018, which claims the benefit of U.S. Provisional Application No. 62/554,530 filed Sep. 5, 2017, U.S. Provisional Application No. 62/554,533 filed Sep. 5, 2017, U.S. Provisional Application No. 62/569,403 filed Oct. 6, 2017, U.S. Provisional Application No. 62/569,411 filed Oct. 6, 2017, U.S. Provisional Application No. 62/584,565 filed Nov. 10, 2017, and U.S. Provisional Application No. 62/593,014 filed Nov. 30, 2017, each of which applications is herein incorporated by reference in its entirety.

INCORPORATION OF SEQUENCE LISTING

Pursuant to 37 C.F.R. 1.821(c), a sequence listing is submitted herewith as an ASCII compliant text file named "STIP0006US_ST25.txt", created on Mar. 2, 2020 and having a size of ~10 kilobytes. The content of the aforementioned file is hereby incorporated by reference in its entirety.

The present disclosure relates to a method of targeting extracellular vesicles employing a molecule comprising a GLA domain and extracellular vesicles obtained or obtainable from a method disclosed herein.

TECHNICAL BACKGROUND

Extracellular vesicles (also known as microvesicles or microparticles) were historically thought to be vehicles for cells to eject waste material. However, in recent times it has been established that in fact extracellular vesicles are involved in vitally important cell to cell communication.

It has been demonstrated that extracellular vesicles can be derived from almost all mammalian cells, including healthy cells, stem cells, and diseased cells, such as cancer cells. The extracellular vesicles are extremely stable and can exist in almost all body fluids including: blood plasma, *salvia*, urine, bile, synovial fluid, semen and breast milk.

Diseased cells such as cancer cells, are thought to employ extracellular vesicles, such as exosomes, to prepare and seed sites for metastasis. Pathogen infected cells may employ extracellular vesicles to spread infection. In addition, bacterial cells are known to release extracellular vesicles.

There is great interest in studying, understanding and harnessing these extracellular vesicles, especially those involved in pathogenic processes. It has been suggested that these vesicles can be employed in therapy as an alternative to stem cells.

However, there are certain practical difficulties because the vesicles are minute and are present at low concentrations in vivo. In addition, there are few markers to distinguish disease-cell-derived extracellular vesicles from normal-cell-derived extracellular vesicles. A further complication is that in vivo these tiny entities are in a complex environment comprising a melange of biological molecules, factors, ions, minerals, etc, etc. Therefore, even isolating and/or monitoring these extracellular vesicle is a challenge.

Seven or more steps may be required to isolate the vesicles and the main parameter employed is usually size. Since the diameter of extracellular vesicles may be below 300 nm and because they have a low refractive index, extracellular vesicles are below the detection range of many currently used techniques. A number of miniaturized systems, exploiting nanotechnology and microfluidics, have been developed to expedite extracellular vesicle analysis. These new systems include a microNMR device, a nanoplasmonic chip, and an magneto-electrochemical sensor for protein profiling; and an integrated fluidic cartridge for RNA detection. Flow cytometry is an optical method to detect extracellular vesicles in suspension. Nevertheless, the applicability of flow cytometry to detect single extracellular vesicles is still inadequate due to limited sensitivity and potential measurement artifacts such as swarm detection. Other methods to detect single extracellular vesicles are atomic force microscopy, nanoparticle tracking analysis, Raman microspectroscopy, tunable resistive pulse sensing, and transmission electron microscopy.

Beyond the opportunity to isolate the extracellular vesicle for study and/or diagnostic purposes, it is also considered that these extracellular vesicles may be suitable for use as natural vehicles to load with payloads, target and/or treat an array of maladies. However, significant challenges currently exist to realizing the potential to load cargos and targeting moieties:

into these extracellular vesicles—
    such as proteins, nucleic acids—both natural and non-natural oligonucleotides—small molecules, enzymes, probes to define the content within the extracellular vesicles for treatment, diagnostic/prognostic purposes etc;
  and onto these extracellular vesicles—
    to develop, alter or enhance targeting, to display therapeutic proteins, to label and for example collect extracellular vesicles for analysis or manipulation,
  some microRNAs have been shown to enter vesicles but to date no robust mechanism exists for getting material inside the vesicle,
    e.g. damaged via electroporation, integration of transfection reagents may compromise the commercial utility of the extracellular vesicle,
    inefficient transduction by viral vectors, loading or isolating via means that alter the extracellular vesicles may also compromise the diagnostic or therapeutic potential, etc. (rev. in Vader et al., Adv Drug Delivery Rev 106: 148-156, 2016, Sutaria et al., Pharm Res 34: 1053-1066, 2017, Lu et al., Eur J Pharm and Biopharm 119: 381-395, 2017),
    saponins have also been suggested as reagents for increasing the permeability of the extracellular vesicles. However, saponins have complicated biological activity including being hemolytic. Fractions of saponins Quil A and QS-21 are used as vaccine adjuvants to increase immune responses to antigen. Therefore the use of saponins is not straightforward.

Thirdly, it may be useful to target pathogenic material and signals in the extracellular vesicles to reduce the spread of pathogenesis.

The disclosure herein addresses the above issues.

Surprisingly, those extracellular vesicles released from pathogenic cells, for example cancerous cells, bacterial cells etc have surface exposed phosphatidylserine. The exposed phosphatidylserine may, for example, act to downregulate immune responses to the "pathogenic" vesicles. Whilst not wishing to be bound by theory it may be that the "pathogenic extracellular vesicles" are characterized by the presence of exposed phosphatidyl serine as opposed to normal-healthy extracellular vesicles, which do not have surface exposed phosphatidylserine.

Phosphatidylserine can be targeted by GLA-components comprising a GLA-domain without the presence of a catalytic domain. These molecules can be employed to target vesicles derived from apoptotic cells, for example abnormal, diseased/infected cells.

Even more surprisingly the present inventors have also shown that the GLA-components also bind stems cells (for example healthy stem cells). Whilst not wishing to be bound by theory these cells may present phosphatidylserine on their surface, which may contribute to the immune suppressive effects an inflammatory effects of stem cells.

Extracellular vesicles derived from cells with surface exposed phosphatidyl serine also have surface exposed phosphatidyl serine on their outer surface. Thus, the GLA-components can also used to target extracellular vesicles from stem cells.

The GLA-domain can be linked or fused to a payload, for example a label, bead, a diagnostic molecule, a targeting motif and/or therapeutic. This allows, isolation, identification, tracking, and/or therapeutic intervention of or via these extracellular vesicles.

Alternatively, or additionally the payload can be a therapeutic, for example a drug, a biological therapeutic, a polymer or a toxin, such as a therapeutic virus, an oncolytic virus, a viral vector, an anti-viral drug, anti-bacterial drug, anti-parasitic agent, anti-cancer drug, an anti-cancer therapy or a chemotherapeutic agent, a virus or viral vector (such as an oncolytic virus).

Thus, the GLA-components can be employed to anchor payloads to the surface of the extracellular vesicles via the GLA-domain binding surface exposed phosphatidyl serine.

In addition, in the present inventors have data to suggest that the GLA-component employed in the present disclosure may be able to transport payloads attached thereto inside the extracellular vesicle. Thus, the GLA-component may be employed to deliver payloads to the interior of the extracellular vesicle.

This has important implications for therapeutic and/or diagnostic uses because known and existing techniques and effector/reporter molecules can be refocused and employed to monitor, isolate and therapeutically intervene with the vesicles.

Once labelled, the vesicles can be monitored, for example in vivo, or isolated using known techniques, such as flow cytometry, magnetic sorting and the like.

Furthermore, it is starting to emerge that the presence of the particular types of vesicles may be used as a non-invasive diagnostic for certain pathologies.

In addition, given the hypothesis that cancers use the vesicles to seed and promote metastasis, then destroying, removing or targeting these vesicles with therapy may be a method to prevent or reduce metastasis, for example nucleotides, such as RNAi can be transported into the extracellular vesicle to knock out active microRNAs carried in the vesicle.

The vesicles shed from infected cells, such as virally infected cells, contain cellular material, for example RNA, protein, lipids and carbohydrates, from the infected cell and also nucleic acids of viral origin. These vesicles may have a part to play in the infection of healthy cells. Altan-Bonnet N. 2016. Extracellular vesicles are the Trojan horses of viral infection. Curr Opin Microbiol 32:77-81; Schorey J S, Cheng Y, Singh P P, Smith V L. 2015, Exosomes and other extracellular vesicles in host-pathogen interactions; EMBO Rep 16:24-43, Schorey J S, Harding C V. 2016; and Extracellular vesicles and infectious diseases: new complexity to an old story. J Clin Invest 126:1181-9.

Vesicles, such as exosomes have several properties which make them ideal for delivering material into cells, which includes their small size (e.g. able to cross the blood brain barrier), natural ability to fuse with the plasma membrane of cells to deliver their contents, stable internal environment and their ability to deliver functional molecules to the recipient cell which include: nucleic acids (DNA, mRNA and miRNA), lipids and proteins.

Recent approaches have been aimed at engineering extracellular vesicles for therapeutic applications. These approaches include altering the vesicles content or manipulating their migratory pathways. In particular, it has been demonstrated that extracellular vesicles may serve a role as therapeutic vesicles for the treatment of cancer by decreasing tumour cell invasion, migration and proliferation, increase sensitivity to chemotherapy and may trigger enhanced immune responses and cell death.

It is also emerging that the vesicles may be suitable for use as a vaccine. Vesicles released from virally infected cells represent a unique source of correctly folded and processed viral material, which are ideal for use as antigen in a vaccination. However, vaccines usually require the presence of adjuvant to boost the immune response to the antigen component.

Previous attempts to manipulate extracellular vesicle content using the classical approaches of incubation, electroporation and transfection have suffered limitations due to poor efficiency of transfer, limited size of payload, the presence of residual excipient in the membrane and restrictions on what type of payload can be used. Thus, there are still some challenges to realizing the potential of these vesicles. Therefore, there is a need for novel methods which can effectively deliver content onto and into extracellular vesicles.

The present disclosure facilitates harnessing the potential of extracellular vesicles by enabling them to be: isolated, used for diagnostic purposes, targets for therapeutic intervention and to be employed to deliver therapeutics, for example through attachment or genetic fusion including molecules such as nucleotides, including RNA and DNA to cells.

What is more the expression of phosphatidyl serine on the surface of the vesicle downregulates immune responses to the vesicle. A GLA-component (without a payload attached) binding phospatidylserine on the surface of extracellular vesicle decloaks the vesicle to the immune system. Thus, the GLA-component of the present disclosure may be employed to increase the visibility of the extracellular vesicles to the immune system.

SUMMARY OF THE DISCLOSURE

The present disclosure will now be summarised in the paragraphs below:

1a. A method for targeting extracellular vesicles with surface exposed phosphatidylserine said method comprising the step of introducing a molecule comprising:
   a gamma-carboxyglutamic acid component (GLA-component) said GLA-component comprises a GLA domain or an active fragment thereof, and which does not comprise an active catalytic domain from a GLA protein,
   into a fluid which may comprise the extracellular vesicle, for example microvesicles, apoptotic bodies and exosomes.

1b. A molecule comprising a payload linked to a gamma-carboxyglutamic acid component (GLA-component), wherein said GLA-component comprises a GLA domain or an active fragment thereof, and does not comprise an active catalytic domain from a GLA protein for use in treatment or diagnosis of an extracellular vesicle.

1c. A molecule comprising a payload linked to a gamma-carboxyglutamic acid component (GLA-component), wherein said GLA-component comprises a GLA domain or an active fragment thereof, and does not comprise an active catalytic domain from a GLA protein for use in the manufacture of a medicament for treatment or diagnosis of an extracellular vesicle 2. A method or molecule for use according to paragraph 1a, 1b or 1c, wherein the extracellular vesicle has a diameter in the range 10 nm to 1000 nm.

3. A method or a molecule for use according to paragraph 1a, 1b, 1c or 2, wherein the extracellular vesicle is an exosome.

4. A method or a molecule for use according to any one of paragraphs 1 to 3, wherein the extracellular vesicle (such as an exosome) has a diameter of 1000 nm or less, for example 1 nm to 10 μm, such as 10 nm to 5 μm, in particular 10 nm to 1 μm, more specifically 20 nm to 100 nm, more particularly 30, 40, 50, 60, 70, 80, 90 or 100 nm 5. A method or a molecule for use according to any one of paragraphs 1a, 1b or 1c to 4, wherein the vesicle has a density in the range 1 to 1.5 g/ml, such as 1 to 1.2 g/ml, in particular 1.13 to 1.19 g/ml.

6. A method or a molecule for use according to any one of paragraphs 1a, 1b, 1c to 5, wherein the vesicle comprises one or more transmembrane proteins independently selected from Lamp-1, Lamp-2, CD 13, CD86, Flotillin, Syntaxin-3, CD2, CD36, CD40, CD40L, CD41a, CD44, CD45, ICAM-1, Integrin alpha4, LiCAM, LFA-1, Mac-1 alpha and beta, Vti-IA and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta, tetraspanins and combinations of two or more of the same.

7. A method or a molecule for use according to any one of paragraphs 1a, 1b, 1c to 6, wherein the vesicle was released from an unhealthy cell, for example an apoptotic cell, a necrotic cell, a cancer cell, a pathogen infected cell (such as a virus infected cell, a bacteria infected cell or a parasite infected cells).

8. A method or a molecule for use according to paragraph 7, wherein the cell is a cancer cell.

9. A method or a molecule for use according to paragraph 8, wherein the cell is a cancer stem cell.

10. A method or a molecule for use according to any one of paragraphs 1 to 6, wherein the extracellular vesicle is from a healthy stem cell.

11. A method or a molecule for use according to any one of paragraphs 1a, 1b, 1c to 10 wherein the fluid comprises an ex vivo patient sample, for example a blood sample, fluid drawn from a cyst or tumor, homogenised biopsy or similar.

12. A method or a molecule for use according to any one of claims 1 to 10, wherein the GLA-component is administered in vivo.

13. A method or a molecule for use according to any one of paragraphs 1a, 1b or 1c to 12, wherein GLA domain or active fragment thereof is independently selected from thrombin, factor VII, factor IX, factor X, protein C, protein S, protein Z, Osteocalcin, Matrix GLA protein, GAS6, Transthretin, Periostin, Proline rich GLA 1, Proline rich GLA 2, Proline rich GLA 3 and Proline rich GLA 4.

14. A method or a molecule for use according to any one of paragraphs 1a, 1b or 1c to 13, wherein GLA domain or active fragment thereof is independently selected from thrombin, factor VII, factor IX, factor X, protein C, protein S, protein Z and GAS6, for example protein S, in particular comprising a sequence shown in SEQ ID NO: 1

15. A method or a molecule for use according to any one of paragraphs 1 to 11, wherein the GLA-domain-component further comprises an EGF domain, for example a calcium binding EGF domain.

16. A method or a molecule for use according to paragraph 15, wherein the construct comprises an EGF domain selected from thrombin, factor VII, factor IX, factor X, protein C, protein S, protein Z, Osteocalcin, Matrix GLA protein, GAS6, Transthretin, Periostin, Proline rich GLA 1, Proline rich GLA 2, Proline rich GLA 3 and Proline rich GLA 4.

17. A method or a molecule for use according to paragraph 16, wherein the construct comprises an EGF domain selected from independently selected from thrombin, factor VII, factor IX, factor X, protein C, protein S, protein Z and GAS6, for example the EGF domain from protein S.

18. A method or a molecule for use according to an one of paragraphs 1a, 1b or 1c to 17, wherein the GLA-component comprises a sequence shown in SEQ ID NO: 6 or a derivative thereof wherein the His-tag is absent, in particular a sequence shown in SEQ ID NO: 6.

19. A method or a molecule for use according to any of paragraphs 1a, 1b or 1c to 14, wherein the GLA-domain component further comprises a Kringle domain.

20. A method or a molecule for use according to paragraph 19, wherein the Kringle domain is from a protein selected from the group comprising Activating transcription factor 2 (ATF); Factor XII (F12); thrombin (F2); Hyaluronan-binding protein 2 (HABP2); Hepatocyte growth factor (HGF); Hepatocyte growth factor activator (HGFAC); Kremen protein 1 (KREMEN1); KREMEN2; Lipoprotein (a) (LPA); LPAL2; Macrophage-stimulating protein (MSP or MST1); Phosphoinositide-3-kinase-interacting protein 1 (PIK3IP1); Tissue plasminogen activator (PLAT); Urokinase (PLAU); Plasmin (PLG); PRSS12; Tyrosine-protein kinase transmembrane receptor ROR1 (ROR1); and Tyrosine-protein kinase transmembrane receptor ROR2 (ROR2).

21. A method or a molecule for use according to any one of paragraphs 1a, 1b or 1c to 20, wherein the GLA-component is linked to a payload.

22. A method or a molecule for use according to paragraph 21, wherein the GLA-component is conjugated to the payload.

23. A method or a molecule for use according to any one of paragraphs 1a, 1b or 1c to 22, wherein the GLA-component is part of a fusion protein.

24. A method or a molecule for use according to paragraph 23, wherein payload comprises a detectable label.

25. A method or a molecule for use according to paragraph 24, wherein the label is selected from a fluorescent molecule (including a fluorescent probe (such as rhodamine dye, FITC, FAM, CY5), biotin, an enzyme, a tag (for example a HIS-tag, FLAG-tag, myc-tag), a radionuclides (particularly radioiodide, radioisotopes, such as $^{99m}$Tc), luminescent labels or compounds which may be detected by NMR or ESR spectroscopy including wherein the detectable label is in a Molecular Beacon.

26. A method or a molecule for use according to any one of paragraphs 1a, 1b or 1c to 25, wherein the payload is a bead, plate or a tag, for example an isolatable bead, such as a magnetic bead.
27. A method or a molecule for use according to paragraph 21 to 26, wherein the payload is linked to the GLA-component via a linker.
28. A method or a molecule for use according to paragraph 27, wherein the linker is cleavable.
29. A method or a molecule for use according to any one of paragraphs 21 to 28, wherein the GLA-component and payload are a diagnostic.
30. A method or a molecule for use according to any one of paragraphs 1a, 1b or 1c to 29, wherein the method comprises a further step of providing an enriched population of the extracellular vesicles.
31. A method or a molecule for use according to any one of paragraphs 1a, 1b or 1c to 30, wherein the method comprises the step of isolating the extracellular vesicles.
32. A method or a molecule for use according to any one of paragraphs 1a, 1b or 1c to 31, wherein the method is performed in vitro.
33. A method or a molecule for use according to any one of paragraph 1a, 1b or 1c to 32, wherein the molecule comprising the GLA-component is a therapeutic.
34. A method or a molecule for use according to any one of paragraphs 21 to 25 and 33, wherein the payload comprises a drug, a chemotherapeutic agent, a peptide (including stapled peptides) or biological therapeutic, for example: an anti-viral drug, anti-bacterial drug, anti-parasitic agent, anti-cancer drug, an anti-cancer therapy.
35. A method or a molecule for use according to any one of paragraphs 21 to 25, 33 and 34, wherein the payload comprises a toxin, a polymer (for example synthetic or naturally occurring polymers), biologically active proteins (for example enzymes, other antibody or antibody fragments e.g. intrabodies), a drug (small molecule (chemical entity), c, nucleic acids and fragments thereof (for example DNA, RNA and fragments thereof) a metal chelating agent, nanoparticles or a combination of two or more of the same.
36. A method or a molecule for use according to paragraph 35, wherein the toxin is selected from an auristatin (for example MMAE (monomethyl auristatin E), MMAF (monomethyl auristatin F)), pyrrolobenzodiazepine (PBD), doxorubicin, duocarmycin, a maytansinoid (for example N 2'-deacetyl-N 2'-(3-mercapto-1-oxopropyl)-maytansine (DM1), N 2'-deacetyl-N2'-(4-mercapto-1-oxopentyl)-maytansine (DM3) and N 2'-deacetyl-N 2'(4-methyl-4-mercapto-1-oxopentyl)-maytansine (DM4)), calocheamicin, dolastatin, maytansine, α-amanitin, Pseudomonas exotoxin (PE38), ricin A chain, diphtheria toxin, Pokeweed antiviral protein (PAP), saporin, gelonin and a tubulysin.
37. A method or a molecule for use according to any one of paragraphs 34 to 36, wherein the chemotherapeutic is selected from temozolomide, epothilones, melphalan, carmustine, busulfan, lomustine, cyclophosphamide, dacarbazine, polifeprosan, ifosfamide, chlorambucil, mechlorethamine, busulfan, cyclophosphamide, carboplatin, cisplatin, thiotepa, capecitabine, streptozocin, bicalutamide, flutamide, nilutamide, leuprolide acetate, doxorubicin hydrochloride, bleomycin sulfate, daunorubicin hydrochloride, dactinomycin, liposomal daunorubicin citrate, liposomal doxorubicin hydrochloride, epirubicin hydrochloride, idarubicin hydrochloride, mitomycin, doxorubicin, valrubicin, anastrozole, toremifene citrate, cytarabine, fluorouracil, fludarabine, floxuridine, interferon α-2b, plicamycin, mercaptopurine, methotrexate, interferon α-2a, medroxyprogersterone acetate, estramustine phosphate sodium, estradiol, leuprolide acetate, megestrol acetate, octreotide acetate, deithylstilbestrol diphosphate, testolactone, goserelin acetate, etoposide phosphate, vincristine sulfate, etoposide, vinblastine, etoposide, vincristine sulfate, teniposide, trastuzumab, gemtuzumab ozogamicin, rituximab, exemestane, irinotecan hydrocholride, asparaginase, gemcitabine hydrochloride, altretamine, topotecan hydrochloride, hydroxyurea, cladribine, mitotane, procarbazine hydrochloride, vinorelbine tartrate, pentrostatin sodium, mitoxantrone, pegaspargase, denileukin diftitix, altretinoin, porfimer, bexarotene, paclitaxel, docetaxel, arsenic trioxide, tretinoin and combinations of two or more of the same.
38. A method or a molecule for use according to any one of paragraphs 34 to 37, wherein the chemotherapeutic is selected from an alkylating agent, an antimetabolite including thymidylate synthase inhibitors, a taxane, an anthracycline, an anti-microtubule agent including plant alkaloids, and combinations of two or more of the same.
39. A method or a molecule for use according to paragraph 38, wherein the chemotherapeutic is selected from paclitaxel, docetaxel, abraxane, carbazitaxel, derivatives of any one of the same, and combinations of two or more of any of the aforementioned.
40. A method or a molecule for use according to claim 38 or 39, wherein the alkylating agent is selected from a nitrogen mustard, a nitrosourea, a tetrazine, a aziridine, a platin and derivatives thereof, a non-classical alkylating agent and a combination of two or more of the same.
41. A method or a molecule for use according to paragraph 40, where the platin is selected from cisplatin, carboplatin, oxaliplatin, satraplatin, picoplatin, nedaplatin, triplatin, lipoplatin and a combination of two or more of the same.
42. A method or a molecule for use according to any one of paragraphs 38 to 41, wherein the alkylating is an antimetabolite selected from anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed (tomudex) hydrochloride, cladribine and 6-azauracil and combination of two or more thereof.
43. A method or a molecule for use according to any one of paragraphs 40 to 42, wherein the anthracycline is selected from daunorubicin (Daunomycin), daunorubicin (liposomal), doxorubicin (Adriamycin), doxorubicin (liposomal), epirubicin, idarubicin, mitoxantrone and a combination of two or more thereof, in particular doxorubicin.
44. A method or a molecule for use according to any one of paragraphs 34 to 43, wherein the drug is an anti-cancer drug, for example selected from a topoisomerase inhibitor, a PARP inhibitor and a combination of or more of the same.
45. A method or a molecule for use according to any one of paragraphs 34 to 44, wherein the anticancer therapy is a radionuclide, for example selected from Y-90, P-32, I-131, In-111, Sr-89, Re-186, Sm-153, Sn-117m and a combination of two or more of the same.

46. A method or a molecule for use according to any one of claims 1a, 1b or 1c to 25 and 27 to 45, which comprises administering the molecule comprising the GLA component and payload to a cancer patient.

47. A method or a molecule for use according to paragraph 46, wherein the cancer is an epithelial cancer, for example colorectal cancer, testicular cancer, liver cancer, biliary tract cancer, prostate cancer, pancreatic cancer, breast cancer, ovarian cancer, cervical cancer, uterine cancer, gastric cancer, oesophageal cancer, thyroid cancer, renal cancer, bladder cancer, brain cancer, head and neck cancer or lung cancer or alternatively the cancer may be a haematological cancer, for example leukaemia, lymphoma, myeloma and chronic myeloproliferative diseases, such as AML.

In one embodiment the method of the present disclosure does not target an apoptotic body.

Thus, in one embodiment the molecules according to the present disclosure are employed in the treatment of a pathogen, for example viral, bacterial, protozoan, parasitic infections, including intracellular forms thereof.

The present disclosure also extends to the use of a GLA-component comprises a GLA domain or an active fragment thereof, wherein said GLA-component does not comprise an active catalytic domain from a GLA protein, for intravesicle targeting and delivery (including intravesicle delivery of the payload).

The present disclosure also extends to the use of a GLA-component comprises a GLA domain or an active fragment thereof, wherein said GLA-component does not comprise an active catalytic domain from a GLA protein, for the manufacture of a medicament for intracellular targeting and delivery (including intravesicle delivery of the payload, in particular where the payload comprises a therapeutic entity/molecule).

Thus, in one aspect there is provided an in vitro method of generating/isolating vesicles from pathogen infected human cell-lines employing method disclosed herein, for example HEp-2 cells, A549 cells, Calu-3 cells, HEK and Madin Darby Kidney Cells (MDCK), for example for use in a vaccine.

In one embodiment the in vitro generated/isolated vesicle is loaded with a payload, for example an oligonucleotide or polynucleotide, such as an RNA or DNA, such CPG, employing a a gamma-carboxyglutamic acid component (GLA-component) comprising a GLA domain or an active fragment thereof, and which does not comprise an active catalytic domain from a GLA protein.

In one embodiment the in vitro generated/isolated vesicle is loaded an immunostimulator molecule, employing a gamma-carboxyglutamic acid component (GLA-component) comprising a GLA domain or an active fragment thereof, and which does not comprise an active catalytic domain from a GLA protein.

Extracellular vesicles mimetic can be generated in vitro by breaking down cells through serial extrusion, see for example Jang et al Nano 2013, 7, 7698. These mimetic will have phosphatidylserine on their surface if they are generated from apoptotic cells or stem cells.

In one embodiment the oligonucleotide or polynucleotide is conjugated to the GLA component.

The present disclosure also extends to a vaccine composition comprising extracellular vesicles from a pathogen infected cell and loaded with: an exogenous immunostimulatory molecule, for example selected from an adjuvant, for example TLR9 agonist, such as a CPG, C3b, ICAM-1; and a GLA component according to the present disclosure.

The vesicles in the vaccine may be have been generated in vivo or in vitro. Vesicles may be generated in vitro in a pathogen infected human cell line, for example selected from HEp-2 cells, A549 cells, Calu-3 cells, HEK and Madin Darby Kidney Cells (MDCK).

The exogenous immunostimulatory molecule may be loaded: on the exterior, in the interior of the "pathogen-derived" vesicle or may be located in both locations.

The GLA component may be loaded: on the exterior, in the interior of the "pathogen-derived" vesicle or may be located in both locations.

In one embodiment the immunostimulatory molecule is not linked to the GLA component i.e. they are loaded separately, for example the immunostimulatory molecule may be provided as a plasmid, which may be transfected into the vesicle and the GLA component is provide as a protein.

Loading the vesicle with both a GLA component and the immunostimulatory molecules provides two separate mechanisms of action, in that the GLA component binds the phosphatidylserine on the surface of the vesicle thereby revealing the presence of the vesicle to the immune system. The immunostimulatory molecule then boosts the immune systems response to the pathogenic material in the vesicle.

The exogenous immunostimulatory molecule may be linked to the GLA domain, for example conjugated to the GLA component or may be a fusion (expression construct) with the GLA component.

It is advantageous to provided immunostimulatory molecule linked to the GLA-component because the GLA-component can bind phosphatidylserine on the surface of the vesicle thereby loading itself and also the immunostimulatory molecule on the vesicle. In addition, in some instances the GLA-component may internalised on the vesicle and pull with it the immunostimulatory molecule.

In one embodiment the pathogen is bacterial or viral, for example as listed herein, in particular influenza virus, for example influenza A, B, C or D. Influenza A has hemagglutinin subtypes H1, H2, H3, H4, H5, H6, H7, H8, H9, H10, H11, H12, H13, H14, H15, H16, H17, H18 and neuraminidase subtypes N1, N2, N3, N4, N5, N6, N7, N8, N9, N10, N11, such as a strain selected from influenza A: (H1N1) H1N2, H2N1, H911, H3N1, H3N2, and H2N3.a new influenza A H1N1 virus (CDC 2009 H1N1 Flu website).

The technology of the present disclosure may be suitable for preparing a universal flu vaccine.

However, even when used to the prepare a seasonal flu vaccine the present technology is likely to be more efficient and convenient that growing the currently available vaccines on eggs.

The present disclosure also provides a "pathogen-derived" vesicle according to the present disclosure, for treatment, in particular for use as a vaccine.

Also provided is use of a "pathogen-derived" vesicle according to the present disclosure for the manufacture of a medicament, in particular for the manufacture of a vaccine.

As discussed above the GLA-component can be employed to carry a payload, such as a therapeutic payload into the interior of the extracellular vesicle. The therapeutic payload may act on the vesicle itself or may be delivered to a cell by the vesicle and act on the cell, or a combination of these two scenarios.

DETAILED DISCLOSURE

In one embodiment 1, 2, 3, 4 or 5 payloads are linked per GLA-component.

GLA-component (also referred to herein as a gamma-carboxyglutamic acid component) refers to a polypeptide comprising a GLA-domain in the absence of catalytic domain from a GLA protein, such as protein S. The polypeptide may further comprise an EGF domain and/kringle domain, for example from protein S. In one embodiment the GLA-component comprises 30 to 300 amino acid residues, for example 50, 60, 70, 80, 90, 100, 110, 120, 130, 140, 150, 160, 170, 180, 190, 200, 210, 220, 230, 240, 250, 260, 270, 280, 290 or 300 residues. In one embodiment the GLA component is in the range of 4.5 to 30 kDa. In one embodiment the GLA-component comprises the sequence shown in SEQ ID NO: 1. In one embodiment the GLA-component comprises a sequence shown in SEQ ID NO: 6 or a derivative thereof excluding the His-tag.

GLA domains (Vitamin K-dependent carboxylation/ gamma-carboxyglutamic) as employed herein are protein domains which have been modified by vitamin K dependent post-translational carboxylation of glutamate residues in the amino sequence to provide gamma-carboxyglutamate (Gla). In one embodiment the GLA domain employed in the molecules of the present disclosure comprises 30 to 45 consecutive residues from a native (wild-type) GLA domain. In one embodiment the GLA domain comprises 3, 4, 5, 6, 7, 8, 9, 10, 11, 12, 13, 14 or 15 GLA residues.

In one embodiment 30% or less of the GLA-component is GLA residues.

In one embodiment the GLA-component comprises 1 to 5 disulfide bonds, for example 1, 2, 3, 4 or 5 disulfide bonds.

The GLA domain binds calcium ions by chelating them between two carboxylic acid residues. These residues are part of a region that starts at the N-terminal extremity of the mature form of Gla proteins, and that ends with a conserved aromatic residue. This results in a conserved Gla-x(3)-Gla-x-Cys motif that is found in the middle of the domain, and which seems to be important for substrate recognition by the carboxylase.

GLA domains are contained in a number of proteins, such as Thrombin, Factor VII, Factor IX, Factor X, Protein C, Protein S (PrS), Protein Z, Osteocalcin, Matrix GLA protein, GAS6, Transthretin, Periostin, Proline rich GLA 1, Proline rich GLA 2, Proline rich GLA 3, and Proline rich GLA 4.

GLA domain as employed herein also extends to proteins where 1 to 10 percent (such as 1, 2, 3, 4, 5, 6, 7, 8, 9 or 10%) of the amino acids in the native GLA domain may be replaced and/or deleted, provided that modified domain retains at least 70% (such as 75, 80, 85, 90, 91, 92, 93, 94, 95, 96, 97, 98, 99 or 100%) of the native activity of the native (unmodified GLA domain) in a suitable in vitro assay. In one embodiment the domain is the full-length native domain.

EGF domain as employed herein refers is a conserved protein domain. It comprises about 30 to 40 amino-acid residues and has been found in a large number of mostly animal proteins. Most occurrences of the EGF-like domain are found in the extracellular domain of membrane-bound proteins or in proteins known to be secreted. The EGF-like domain includes 6 cysteine residues. The main structure of EGF-like domains is a two-stranded β-sheet followed by a loop to a short C-terminal, two-stranded β-sheet. These two β-sheets are usually denoted as the major (N-terminal) and minor (C-terminal) sheets. EGF-like domains frequently occur in numerous tandem copies in proteins: these repeats typically fold together to form a single, linear solenoid domain block as a functional unit. In one embodiment the domain employed is the full-length native domain.

EGF domain as employed herein also extends to proteins where 1 to 10 percent (such as 1, 2, 3, 4, 5, 6, 7, 8, 9 or 10%) of the amino acids in the native EGF domain may be replaced and/or deleted, provided that modified domain retains at least 70% (such as 75, 80, 85, 90, 91, 92, 93, 94, 95, 96, 97, 98, 99 or 100%) of the native activity of the native (unmodified EGF domain) in a suitable in vitro assay. In one embodiment the domain is the full-length native domain.

Kringle domain as employed herein refers to autonomous protein domains that fold into large loops stabilized by 3 disulfide bonds. They are characterized by a triple loop, 3-disulfide bridge structure, whose conformation is defined by a number of hydrogen bonds and small pieces of anti-parallel beta-sheet. They are found throughout the blood clotting and fibrinolytic proteins, in a varying number of copies, in some plasma proteins including prothrombin and urokinase-type plasminogen activator, which are serine proteases belonging to MEROPS peptidase family S1A.

Kringle domain as employed herein also extends to proteins where 1 to 10 percent (such as 1, 2, 3, 4, 5, 6, 7, 8, 9 or 10%) of the amino acids in the native kringle domain may be replaced and/or deleted, provided that modified domain retains at least 70% (such as 75, 80, 85, 90, 91, 92, 93, 94, 95, 96, 97, 98, 99 or 100%) of the native activity of the native (unmodified Kringle domain) in a suitable in vitro assay. In one embodiment the domain employed is the full-length native domain.

An active fragment of a protein as employed herein is a less than the whole native protein (or relevant domain), which retains at least 50% (such as 60, 70, 80, 85, 90, 91, 92, 93, 94, 95, 96, 97, 98, 99 or 100%) of the activity of the native full-length domain or protein in a relevant in vitro assay.

Catalytic domain as employed herein is a domain (or fragment) downstream of the EGF domain in the C-terminal direction, for example as illustrated in FIG. 1A.

In vitro as employed herein refers to laboratory work not performed in a human or animal body.

In vivo as employed herein refer to work/testing/treatment in a living organism, in particular a human or animal, in particular human.

Extracellular vesicles (EVs) are important mediators of long distance intercellular communication and are involved in a diverse range of biological processes across both prokaryotic and eukaryotic organisms (rev. in Arenaccio and Federico, Adv Exp Med Biol 998: 3-19, 2017, Lu et al., Eur J Pharm Biopharm 119: 381-195, 2017, Vader et al., Adv Drug Delivery Rev 106:148-156, 2016, Lefebvre and Lecuyer, Front Microbiol 8: 377, 2017).

Extracellular vesicles are shed from infected cells (viral, bacterial or parasitic) and contain material from these infectious agents (rev. in Schorey et al., EMBO Rep. 16: 24-43, 2015, Schorey and Harding, J. Clin Invest. 126: 1181-1189, 2016). This material can vary from toxins to virulence factors to infectious virus (both enveloped and non-enveloped; rev. in Altan-Bonnet, N, Curr Opin Microbiol 32: 77-81, 2016) and may be a novel means to more effectively deliver viral populations rather than single viral particles (Chen Y H et al., Cell 160: 619-630, 2015). Consequently, their isolation could provide rapid diagnostic insight into disease.

Extracellular vesicles is a broad term to describe all secreted membrane vesicles. As employed herein the term includes exosomes, microvesicles (also referred to microparticles), ectosomes, matrix vesicles, calcifying vesicles, prostasomes, oncosomes, retrovirus-like particles, bacterial extracellular vesicles, intraluminal vesicles and apoptotic bodies.

In addition, the extracellular vesicles, which contain proteins, RNA, andcarbohydrates specific to the infectious agent and cell may also potentially be systems for in situ vaccination. In this setting, it is envisioned that the engagement and neutralization of the immune dampening phosphatidylserine molecules due to the GLA domain enables immune detection and clearance and serve as a novel and more effective method of specific vaccination for the infectious disease.

Extracellular vesicles as employed herein includes microvesicles, apoptotic bodies, and exosomes. Extracellular vesicles generally have a diameter in the range 10 nm to 5000 nm.

Microvesicles as employed herein refers to vesicles released after formation by budding form the cytomembrane, and for example generally have a diameter in the range 100 nm to 1000 nm.

Exosomes are produced inside multivesicular bodies and are released after fusion of the multivesicular body with the cytomembrane. Generally, exosomes have a diameter in the range 30 to 100 nm.

Apoptotic bodies as employed herein refer to vesicles shed into the extracellular environment by apoptotic cells. Apoptotic bodies may not be involved in intracellular communication. Generally, the diameter of apoptotic bodies is in the range 800 nm to 5000 nm.

See for example Modularized Extracellular Vesicles: The Dawn of Prospective Personalized and Precision Medicine, Tao et al Adv. Sci. 2018, 5, 1700449; Mesenchymal Stem Cell-derived Extracellular Vesicles: Towards Cell-free Therapeutic Applications Rani et al, www.moleculartherapy.org vol. 23 no. 5, 812-823 May 2015; and Achieving the Promise of Therapeutic Extracelluar Vesicles: The Devil is in the Detail of Therapeutic Loading Sutaria et al, Pharma Res. 2017 May; 34(5) 1053-1066, incorporated herein by reference.

Thus, the present disclosure provides use of extracellular vesicles for the diagnosis, for example of infection with a pathogen, for example a viral infection, bacterial infection and/or parasitic infection.

Thus, the present disclosure provides use of extracellular vesicles for the treatment, for example of infection with a pathogen, for example a viral infection, bacterial infection and/or parasitic infection, in particular where the extracellular vesicle is treated to neutralize or eliminate pathogenic material and/or the extracellular vesicle is loaded with therapeutic material for delivery to a target cell.

Thus, the present disclosure provides use of extracellular vesicles for the diagnosis of infection with a pathogen, for example a viral infection, bacterial infection and/or parasitic infection.

Thus, the present disclosure provides use of extracellular vesicles for the treatment, for example of infection with a pathogen, for example a viral infection, bacterial infection and/or parasitic infection, in particular where the extracellular vesicle is treated to neutralize or eliminate pathogenic material and/or the extracellular vesicle is loaded with therapeutic material for delivery to a cell.

Thus, the present disclosure provides use of extracellular vesicles for the diagnosis of cancer.

Thus, the present disclosure provides use of extracellular vesicles for the treatment of a cancer, for example where the extracellular vesicle is treated to neutralize or eliminate pathogenic material and/or the extracellular vesicle is loaded with therapeutic material for delivery to a cell.

Extracellular vesicles and methods according to the present disclosure may also be useful in the diagnosis and/or treatment of autoimmune disease, especially extracellular vesicles from stem cells.

In one embodiment the extracellular vesicles of the disclosure are from a human cell.

In one embodiment the extracellular vesicles are from stem cells (in particular healthy stem cells). These vesicles can be used in a similar way to stem cell therapy.

In one embodiment the extracellular vesicles of the disclosure are from a pathogenic cell, such as a bacterial cell.

Cells can secrete different types of EVs and these have been classified according to their sub-cellular origin (Colombo et al., Annu Rev Cell Dev Biol 30: 255-289, 2014). Despite differences in origin and size, no uniform EV nomenclature exists due to the overlap in vesicle sizes and in the absence of subtype-specific markers. As a result, it remains difficult to purify and thereby distinguish between vesicle types. For example, the most popular exosome purification protocols used historically in the literature (differential ultracentrifugation, 220 nm filtration (Thery et al., Curr Protoc Cell Bioil Chapter 3, Unit 3.22, 2006)—and recently released in commercial kits—co-isolates different types of EVs (rev. Tkach and Thiery, Cell 164: 1226-1232, 2016). Thus, terms like "exosome" are generally referred to as a mixed population of small EVs and hence, for this invention, we have chosen to use the generic term EVs so as to refer to all vesicle subtypes.

Generally, extracellular vesicles comprise a lipid bilayer comprising ceramides, cholesterols, phosphoglycerides and sphingolipids (Subra et al 2010, Trajkovic et al 2008, Vlassov et al 2012)

All extracellular vesicles bear surface molecules that allow them to be targeted to recipient cells where they signal and/or deliver their content into its cytosol through an array of means (e.g. endocytosis and/or phagocytosis, fusion etc.), thereby modifying the physiological state of the recipient cell. Since they are natural delivery vehicles for protein, lipids and genetic material, they represent a unique biovector that is actively being explored across an array of disease indications for imaging, diagnostics, and/or for use as therapeutic carriers (rev. in Rufino-Ramos et al., J. Control Release 262: 247-258, 2017, Vader et al., Adv Drug Deliv. Rev 106: 148-156, 2016, Sutaria et al., Pharm Res. 34: 1053-1066, 2017, Ingato et al., J. Control Release 241: 174-185, 2016).

In one embodiment the extracellular vesicle is an exosome. Exosomes are generally in the range 30 to 150 nm, such as 30 to 100 nm in diameter, and for example may bear one or more surface markers selected from transferrin, CD9, CD63, CD61, CD81, TSG101, LAMPS and Alix.

In one the extracellular vesicle is a microvesicle (also referred to a microparticle) and include endothelial microparticles. Generally, microvesicles have a diameter in the range 50 to 2000 nm and, for example may bear one or more surface markers, selected from VCAMP3 and ARF6. Although, circulating endothelial microparticles can be found in the blood of normal individuals, increased numbers of circulating endothelial microparticles have been identified in individuals with certain diseases, including hypertension and cardiovascular disorders, and pre-eclampsia and various forms of vasculitis. The endothelial microparticles in some of these disease states have been shown to have arrays of cell surface molecules reflecting a state of endothelial dysfunction. Therefore, endothelial microparticles may be useful as an indicator or index of the functional state of the endothelium in disease, and may potentially play key roles in the pathogenesis of certain diseases, including rheumatoid arthritis.

In one embodiment the extracellular vesicle is an ectosome. Generally, ectosomes have a diameter in the range 100 to 1000 nm, such as 350 to 400 nm and may, for example bear one or more surface markers selected from TyA nd C1a.

In one embodiment the vesicle is a calcifying extracellular vesicle. These vesicles are released from cells within atherosclerotic plaques. Recently, calcifying EVs derived from macrophages and smooth muscle cells (SMCs) have received increased attention for their role in vascular calcification. These vesicles are thought to have a role in mediating vascular calcification, a major predictor of cardiovascular morbidity and mortality.

In one embodiment the extracellular vesicle is a matrix vesicle. Matrix vesicles as referred to herein are involved in bone development, wherein osteoblast-derived vesicles nucleate hydroxyapatite crystals along collagen fibres in the developing bone. They also serve as nucleating foci for the formation of microcalcifications within atherosclerotic plaque fibrous caps, which leads to plaque instability, rupture and subsequent myocardial infarction and stroke.

In one embodiment the extracellular vesicle is a prostasome. Prostasome as employed herein refers to vesicles secreted by the prostate gland epithelial cells into seminal fluid. They generally have a diameter in the range 40 to 500 nm. They possess an unusual lipid composition and a tight and highly ordered structure of their lipoprotein membranes resembling lipid raft. The physiological role of prostasomes implicates improvement of sperm motility and protection against attacks from the female immune defence during the passage to the egg. Investigations have shown that cancerous prostate cells and prostate cells with low differentiation continue to produce and secrete prostasomes. The high incidence of prostate cancer in elderly men could take advantage of the immune protective activities supported by the prostasomes. Immune regulating proteins found in prostasomes include: amino-peptidase N (CD13); dipeptidyl-peptidase IV (CD26); enkephalinase (neutral endopeptidase, CD10); angiotensin converting enzyme (ACE, CD143); tissue factor TF (CD142, thromboplastin); decay accelerating factor (CD55); protectin (CD59, inhibitor of MAC) and complement regulatory membrane cofactor protein (CD46). Prostasomes also contain high levels of the divalent cations: $Zn^{2+}$, $Ca^{2+}$ and $Mg^{2+}$.

In one embodiment the extracellular vesicle is an oncosome. Oncosome as employed herein refers to large extracellular vesicles in the range 1 μm to 10 μm in diameter. In the context of brain tumors, the existence of EVs released from glioma cells and expressing EGFRvIII, a mutated form of the receptor. These vesicles were shown to be capable of transferring the oncoprotein EGFRvIII to the membrane of tumor cells lacking this receptor, thus propagating tumor-promoting material and inducing transformation. Large oncosomes positive for Cav-1 have been shown to discriminate patients with locally confined prostate cancer from patients with castration resistant and metastatic disease.

In one embodiment the extracellular particles are retrovirus-like particles. These generally have a diameter in the range 75 to 100 nm and may bear a surface marker Gag.

In one embodiment the extracellular vesicle is a bacterial extracellular vesicle. These vesicles generally have a diameter in the range 10 to 300 nm and may have PAMPs on their surface.

In one embodiment the extracellular vesicle is a intraluminal vesicle. As employed herein this refers to a vesicle within a cell.

Back-fusion is the fusion of internal (intraluminal) vesicles within multivesicular bodies or late endosomes with the endosome's limiting membrane. The process is believed to be mediated by lysobiphosphatidic acid (LBPA), phosphatidylinositol-3-phosphate, Alix, and an apparent dependence on an acidic pH. MHC class 2 and other proteins (CD63 and MPR) utilize such a process to effectively transport to locations in the cytosol and back to the plasma membrane. However, pathogens also exploit this mechanism to efficiently enter the cytosol of the cell (e.g. VSV, anthrax). Unlike regular fusion in the cell between endosomes and organelles, back-fusion requires the exoplasmic leaflets of the internal vesicles and outer membrane to fuse—similar to sperm-egg fusion.

In one embodiment the extracellular vesicle is an apoptotic body. Apoptotic bodies as employed herein generally have a diameter in the range 500 to 5,000 nm, such as 500 to 4000 nm, and are released by cells undergoing programmed cell death.

Stem Cells and Markers

In one embodiment the extracellular vesicle according to the present disclosure is from a stem cell.

In one embodiment the stem cells are embryonic stem cells. In one embodiment the cell are not embryonic stem cells.

In one the stem cell is an adult stems cell, for example including progenitor cells, and haemotopoietic stem cells, myogenic stem cells, osteoprogenitor stem cells, neural stem cells, mesenchymal stem cell, such as satellite cells, radial glial cells, bone marrow stromal cells, periosteum, pancreatic progenitor cells, endothelial progenitor cells, blast cells and trophoblast stem cells.

In one embodiment the stem cell is a cancer stem cell.

In one embodiment the method relates to mammalian stem cells, for example human stem cells. The stem cell discussed herein are primarily human stem cells. However, the skilled person is able to identify the relevant or corresponding stem cell population for other mammals, as required. For example SSEA-1 is a marker for murine embryonic stem cells, human germline cells and embryonal carcinoma cells; SSEA-3 is a marker for primate embryonic stem cells, human embryonic germline cells, human embryonic stem cells and embryonal carcinoma cells; SSEA-4 is a marker for primate embryonic stem cells, human embryonic germ cells, human stem cells, embryonal carcinoma cells; CD324 is a marker for human & murine embryonic stem cells, embryonal cancer cells; CD90 is a marker for human & murine embryonic stems cells, hematopoietic stem cells, embryonal carcinoma cells; CD117 is a marker for human & murine embryonic stem cells, hematopoietic stem progenitor cells, neural crest-derived melanocytes, primordial germ cells, embryonal carcinoma cells; CD326 is a marker for human & murine embryonic stem cells, embryonal carcinoma cells; CD9 is a marker for human & murine embryonic stems; CD24 is a marker for human & murine embryonic stems; CD29 is a marker for human & murine embryonic stems; CD59 is a marker for human & murine embryonic stems; CD133 is a marker for human & murine embryonic stems, embryonal carcinoma cells, hematopoietic stem cells; CD31 is a marker for human & murine embryonic stems; TRA-1-60 is a marker for human embryonic stem cells, teracarcinoma, embryonic germ cells, embryonal carcinoma cells; TRA-1-81 is a marker for human embryonic stem cells, teracarcinoma, embryonic germ cells, embryonal carcinoma cells; Frizzled5 is a marker for human & murine embryonic stem cells; Stem cell factor (SCF) is a marker for human & embryonic stem cells, hematopoietic stem cells, mesenchymal stem cells, embryonal carcinoma cells; and Cripto is a marker for human & murine embryonic stem cells, cardiomyocytes and embryonal carcinoma cells.

Hematopoietic stem cells (HSCs) or hemocytoblasts are the stem cells that give rise to all the other blood cells through the process of haematopoiesis. They are derived from mesoderm and located in the red bone marrow, which is contained in the core of most bones.

Cancer stem cell as employed herein refers to tumorigenic cells (i.e. cancer cells found within tumors or hematological cancers) that possess characteristics associated with normal stem cells, specifically the ability to give rise to all cell types found in a particular cancer sample. See, for example Identification and Targeting of Cancer Stem Cells, BioessayS 2009 October; 31 (10) 1038-1049, incorporated herein by reference. Cancer stem cells are defined by three distinct properties: i) a selective capacity to initiate tumour and drive neoplastic proliferation: ii) an ability to create endless copies of themselves through self-renewal, and iii) the potential to give rise to more mature non-stem cell cancer progeny though differentiation. Cancer stem cells are not necessarily derived from a healthy stem cell but may originate from a differentiated cell.

CD34 is also known as hematopoietic progenitor cells antigen CD34, has a function as cell-cell adhesion factor. It can be employed as a marker to enrich stem populations.

Stem cells are generally negative for lineage positive surface markers (i.e. is Lin −ve), for example the stem cell is Lin −ve, CD34+ve, CD38 −ve, CD45RA −ve, CD90 positive and CD49f_+ve.

Haemotopoietic stem cells may express a surface marker from CD48, CD150, CD244, CD34, CD38, SCA-1, Thy1.1, C-kit, lin, CD135, slam1/CD150, Mac-1 (CD11b), CD4, stem cell factor (SCF) and combinations of two or more of the same.

Osteoprogenitor cells may express a surface marker selected from Gremlin-1, TGF-beta, bFGF, BMP-2, ALPP, MCAM, Collagen I, Collagen 1 alpha 1, Collagen II, RUNX2, Decorin, and combinations of two or more of the same (such as all said markers).

Osteoblasts or a progenitor thereof may express a surface marker selected from Runx2, alkaline phosphatase/ALPP/ALPI, osteocalcin, BAP1, OPN, BAP31, Collagen I, SCUBE3, Fibronectin, SPARC, IGFBP-3, and combinations of two or more of the same.

Osteocyte or progenitor thereof may express a surface marker selected from:
i) TGF beta, RANKL, MCSF, Sclerostin, DKK, and combinations of two or more of the same (such as all said markers) and/or
ii) Osterix+ve, CD90+ve, osteocalcin+ve, collagen I+ve, bone sialoprotein+ve and combinations of two or more of the same (such as all said markers), and/or
iii) alkaline phosphatase/ALPP(alkaline phosphatase placental)/ALPI+ve, collagen I +ve, collagen II+ve, decorin+ve, MCAM/CD146+ve, MEPE/OF45+ve, osterix+ve, CD90+ve, osterix/Sp7+ve, RUNX2/CBFA1+ve, thrombopoietin/Tpo+ve, and combinations of two or more of the same (such as all said markers)

Myogenic stem cells may express a marker selected from CD56, CD146, VE-cadherin, alpha-smooth muscle actin, FABP3, integrin alpha 7, desmin, myosin heavy chain, UEA-1 receptor, and combinations of two or more of the same (such as all said markers).

Neural stem cells may express a marker selected from:
i) CD133, CD15, CD24 low or −ve, GCTM-2, CD45, CD34, Nestin, Sox-2, ABCG2, FGF R4, Frizzled-9, and combinations of two or more of the same (such as all said markers), and/or
ii) CD24 marker is low or −ve, and/or
iii) a marker combination of CD133+ve, 5E12+ve, CD34 −ve, CD45 −ve, and CD24 low or −ve Mesenchymal stem cells may express a surface marker, selected from CD10, CD13, CD73, CD105, CD271, CD140b, CD240, frizzled-9, CD29, CD90, CD146, oct4, SSEA4, STRO-1, stem cell factor (SCF) and combinations of two or more of the same.

A stem cell that is adipose-derived may express a surface marker selected from:
i) K15, CD34, Nestlin, follistatin, p63, integrin alpha 6, teacin C, EGFR, IGFR, frizzled factors, and combinations of two or more of the same, and/or
i) iCD44, ICAM/CD54, CD34, integrin family members and combinations of two or more of the same.

A stem cell from an ovary and tubal epithelial stem cell may express a surface marker selected from Gremlin 1, Lrig1, Lgr5, Bmi1, Tert, HopX and combinations of two or more of the same.

Embryonic stem cells may one or more a surface marker selected from CD24, CD29, CD31, CD59, CD90, CD117, CD133, CD324, CD326, SSEA-3, SSEA-4, TRA-1-60, TRA-1-81, frizzled5, stem cell factor, crypto (TDGF-1).

Extracellular vesicles from stems cells may be identified on the basis of the markers from the cell from which they were derived.

Other Definitions

Payload as employed herein refers to a molecule which is linked to the GLA domain, in particular for delivery to the vesicle. Payloads may comprise a drug, a toxin, a chemotherapeutic, a polymer, a biologically active protein, a peptide (such as stable peptide), a polynucleotide (such as DNA and RNA including microRNA, shRNA, RNAi and the like, including molecular beacons) radionuclides, a metal chelating agent, oncolytic viruses, viral vectors, labels and/or a reporter group. Linked as employed herein refers to any means of the associating the payload to the GLA-domain, including fusion protein (for example employing an amide bond) or a chemical conjugation (for example maleimide chemistry, click chemistry or the like). Payloads may also be used to refer to material delivered to the interior of the extracellular vesicle, wherein the material is not linked to the GLA-component.

The GLA domain is a unique detection and delivery platform that takes advantage of the exposure of phosphatidylserine (PS), to target and access selected cells. Phosphatidylserine is a principal signal for recognition and engulfment of apoptotic cells. Apoptosis is an evolutionarily conserved and tightly regulated cell death modality (Poon I K et al., Nat Rev Immunol 14: 166-180, 2014). The engulfment and ingestion of apoptotic cells is known as efferocytosis, which serves the immediate and effective removal of apoptotic cells before loss of membrane integrity and release of inflammatory contents and thus counterbalances the harmful inflammatory effects of apoptosis. PS expression acts to inhibit TLR-induced and cytokine-induced signaling cascades and immunogenic DC maturation (Poon I K et al, Nat Rev Immunol 14: 166-180, 2014, Birge R B CellI Death Differ 23: 962-978, 2016). Consequently, under physiological conditions, externalized phosphatidylserine functions as a dominant and evolutionarily conserved immunosuppressive signal that promotes tolerance and prevents local and systemic immune activation. Pathologically, the innate immunosuppressive effect of phosphatidylserine has been hijacked by numerous viruses, other microorganisms, and parasites to facilitate infection and in many cases, establish latency (Birge R B et al., Cell Death Differ 23: 962-978, 2016, Amara A and Mercer J, Nat Rev Microbiol 13: 461-469, 2015, Moller-Tank, S and Maury W Virology 468-470: 565-580, 2014). Phosphatidylserine is dysregulated in the tumor microenvironment and antagonizes the development of tumor immunity and phosphatidylserine expressing exosomes are now being explored as early diagnostics in the battle with cancer (Birge R B et al., Cell Death Diff. 23:962-978, 2016, Lea et al., Oncotarget 8: 14395-14407, 2017, Li X and Wang X, Mol Cancer 16: 92, 2017). Whilst not wishing to be bound by theory the present inventors believe that not all phosphatidylserine is equivalent from a biological perspective. The inventors believe that the phosphatidylserine exposes by the enzyme TMEM16F is involved in immune suppression and is the one "seen" by the molecules of the present disclosure.

Oncolytic virus as employed herein refer to a virus that:
preferentially infects and kills cancer cells, or
selectively replicates in the cancer cells (for example because their replication is dependent on a gene that is upregulated in the cancer cells, such as p53.

Viral vector as employed herein refers to a replication deficient virus, generally encoding a transgene.

In vitro as employed herein refers to laboratory work not performed in a human or animal body.

In vivo as employed herein refer to work/testing/treatment in a living organism, in particular a human or animal.

Molecule as employed herein is used in the broadest sense and includes a synthetic chemical molecule but also macromolecules such as proteins, polymers (natural or otherwise), ribonucleic acid molecules, labels etc.

A molecular beacon is an oligonucleotide hybridization probes that can report the presence of specific nucleic acids in homogenous solutions. They are hairpin shaped molecules with an internally quenched fluorophore whose fluorescence is restored when they bind to a target nucleic acid sequence.

Stapled peptide as employed herein refers to multiple tandem peptides, held by a synthetic brace, which is intended to enhance the pharmacological performance of the peptides.

A drug as employed herein, unless the context indicates otherwise, is intended to refer to a small chemical entity, for example which has been synthesised by organic chemistry methods, in particular a molecule approved or licensed or in the process of being licensed for therapeutic use, especially in humans. Drug as employed herein includes an anti-viral compound, an antibiotic, and an anti-cancer therapy.

An antiviral compound (antiviral agent) as employed herein refers to the class of medicaments used specifically for treating viral infections, including broad spectrum antiviral agents and also "narrow" spectrum specific to a particular virus or particular family of viruses.

Antibiotic as employed herein refers to medicine or agent that inhibits the growth of bacteria or destroys bacteria. Anti-bacterial and antibiotic are used interchangeable here unless the context indicates otherwise.

Anti-parasitic as employed herein in refers to a medicine or agent that inhibits the growth of parasite, destroys parasite or removes parasites from the host.

Anti-cancer therapy is a broad term which includes anti-cancer drugs, chemotherapy, radiotherapy, immune-oncology therapies, etc.

Anti-cancer drug as employed herein generally refers to a small molecule cancer therapy.

Chemotherapy as employed herein generally refers to a cytotoxic agent and includes antineoplastics.

A biological therapeutic (also referred to as a biopharmaceutical, biological or biologic) is a therapeutic product "derived" from a biological source, for example a recombinant proteins and fragments, including antibodies molecules, including antibodies, antibody binding fragments and multispecific antibody molecules, polynucleotides, therapeutic viruses, oncolytic viruses, viral vectors and complex combinations of such materials. A biologically active protein is a subgroup of a biological therapeutic and includes recombinant proteins and active fragments thereof (including antibody molecules).

Antibody molecules as employed herein include a complete antibody having full length heavy and light chains or a fragment thereof and a molecule comprising any one of the same for example a Fab, modified Fab, Fab', modified Fab', F(ab')2, Fv, Fab-Fv, Fab-dsFv, single domain antibodies (e.g. VH or VL or VHH), scFv, intrabodies, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in WO2005/003169, WO2005/003170 and WO2005/003171. Multi-valent antibodies may comprise multiple specificities e.g bispecific or may be monospecific (see for example WO 92/22853 and WO05/113605). Bispecific and multispecific antibody variants are especially considered in this example since the aim is to neutralise two independent target proteins. Variable regions from antibodies disclosed herein may be configured in such a way as to produce a single antibody variant which is capable of binding to and neutralising two target antigens.

Antibody and binding fragments thereof, in particular small antibody fragments such as domain antibodies, VHHs, single chain Fvs (scFvs), ds-scFvs, dsFv, and intrabodies may be delivered intracellularly using the present technology.

In one embodiment the antibody molecule is human or humanised.

A toxin is a poisonous substance, especially derived from a natural source, in particular a protein. Many toxins, such as calicheamicin are used in cancer therapy. In addition, chemotherapeutic agents can be considered toxic (or toxins). Thus the definition of toxin overlaps with other definitions herein. However, neurotoxins like snake venom are toxin but not a chemotherapeutic. However, those skilled in the art are familiar with these technical definitions and are capable of understanding the meaning the context of the present disclosure.

Diagnostic as employed herein is agent used in analysis or imaging to diagnose, or monitor or understand a disease status. A diagnostic will generally comprise a reporter molecule, such as a label or similar that can visualized, measured or monitored in some way.

Radionuclides suitable for use the present disclosure include thallium-201, technetium-99m, Iodine-123, Iodine 131, Iodine-125, Fluorine-18 and Oxygen-15.

Abnormal cell or pathogenic cell as employed herein relates to a cell that has differences to a normal healthy cell, in particular mutations or upregulation of a marker or markers, for example an abnormality linked to a predisposition to or development of a condition or diseases; linked with a condition or disease, such as pre-cancerous cell, cancer, a pathogen infected cell, sickle-cell anemia or similar.

Apoptosis as employed herein is cell death pathway which occurs as normal and controlled part an organism growth. Cell death by apoptosis is less damaging to surrounding tissue than cell death mechanisms, such as necrosis.

Necrosis as employed herein is cell death from disease or injury. It releases cytokines and factors into the surrounding tissue that may damage surrounding cells. Gangrene is an example of necrotic cell death.

Chemotherapeutic Agents

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, parp inhibitors and other antitumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent nitrogen mustards, nitrosoureas, tetrazines, aziridines, platins and derivatives, and non-classical alkylating agents.

Example a platinum containing chemotherapeutic agent (also referred to as platins), such as cisplatin, carboplatin, oxaliplatin, satraplatin, picoplatin, nedaplatin, triplatin and lipoplatin (a liposomal version of cisplatin), in particular cisplatin, carboplatin and oxaliplatin.

The dose for cisplatin ranges from about 20 to about 270 mg/m$^2$ depending on the exact cancer. Often the dose is in the range about 70 to about 100 mg/m$^2$.

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed (tomudex) hydrochloride, cladribine and 6-azauracil. Examples of anthracyclines, which may be employed in the method of the present disclosure, include daunorubicin (Daunomycin), daunorubicin (liposomal), doxorubicin (Adriamycin), doxorubicin (liposomal), epirubicin, idarubicin, valrubicin currenity used only to treat bladder cancer and mitoxantrone an anthracycline analog, in particular doxorubicin.

Examples of anti-microtubule agents, which may be employed in the method of the present disclosure, include include vinca alkaloids and taxanes.

Vinca alkaloids include completely natural chemicals for example vincristine and vinblastine and also semi-synthetic vinca alkaloids, for example vinorelbine, vindesine, and vinflunine Taxanes include paclitaxel, docetaxel, abraxane, carbazitaxel and derivatives of thereof. Derivatives of taxanes as employed herein includes reformulations of taxanes like taxol, for example in a micelluar formulaitons, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

Type II poisons include amsacrine, etoposide, etoposide phosphate, teniposide and doxorubicin and fluoroquinolones.

In one embodiment the chemotherapeutic is a PARP inhibitor.

Viruses Suitable for Use as Payloads in the Present Disclosure

In one embodiment the virus employed in the present disclosure is an envelope virus, for example selected from a herpesvirus (such as Herpes simplex 1), a poxvirus (such as vaccina virus), a hepadnavirus, a flavivirus, a togavirus, a coronavirus, hepatitis D, orthomyxovirus, paramyxovirus (such as measles or Newcastle disease virus), rhabdovirus, bunyavirus, filovirus, and Rhabdoviridae (such as vesicular stomatitis Indiana virus (VSV).

In one embodiment the virus employed in the present disclosure is a non-envelope virus, for example selected from adenoviridae (such as an adenovirus), papilomaviridae, picornaviridae (such as coxsackie virus or Seneca Valley virus (eg Senecavirus)), reovirus.

In one embodiment the virus is an adenovirus, for example a human adenovirus, such as selected from a group B virus (in particular Ad3, Ad7, Ad11, Ad14, Ad16, Ad21, Ad34, Ad35, Ad51 or a chimeria thereof, such as Enadenotucirev), a group C virus (in particular Ad1, 2, 5, 6 or a chimeria thereof), a group D virus (in particular Ad8, Ad10, Ad13, Ad15, Ad17, Ad19, Ad20, Ad22, Ad30, Ad32, Ad33, Ad36, Ad37, Ad38, Ad39, Ad42, Ad43, Ad44, Ad45, A46, Ad47, Ad48, Ad49, Ad50 or a chimeria thereof), a group E virus (in particular Ad4), a group F virus (in particular Ad40, Ad41 or a chimeria thereof) and a chimeria of two or more of group B, C, D, E or F viruses.

The vast majority of viruses have well described proteins associated with target cell recognition and uptake. Modification of their tropism to re-direct or enable more selective tumor targeting into oncolytic viruses may be introduced using methods described in rev. in Verheije and Rottier, Adv. Virology 2012: 798526, 2012.

Additional viral cell surface proteins not involved in native viral targeting can have targeting motifs engineered onto them (e.g. Ad virion minor coat protein IX Salisch et al., PLoS One 12: e0174728, 2017).

Envelope viruses have an outer membrane (envelope) covering the virus capsid. The envelope is typically derived from the portions of the host cell membranes (phospholipids and proteins) but also include some viral proteins. Glycoproteins on the surface of the envelope serve to identify and bind to receptor sites on the host's membrane. The viral envelope then fuses with the host's membrane, allowing the capsid and viral genome to enter and infect the host.

Various oncolytic viruses are disclosed in WO2014/13834, incorporated herein by reference.

Herpes simplex virus (HSV) enters cells by means of four essential glycoproteins—gD, gH/gL, gB, activated in a cascade fashion by gD binding to one of its receptors, nectin1 and HVEM. Retargeting of HSV has been achieved by the insertion of ligands and scFvs into the gC and/or gD protein or gH (Campadelli-Fiume, G et al., Rev in Med Virol 21: 213-226, 2011, Gatta, V PLoS Pathog 11: e1004907, 2015). Oncolytic herpes simplex virus type 1 vectors have been developed for clinical use. These viruses are replication competent and have mutations in the genes that affect viral replication, neuropathogenicity, and immune evasiveness, and for example include first generation viruses such as NV1020 (R7020), dlsptk, d18.36tk, hrR3, R3616, 1716, second generation viruses such as G207 (MGH-1), 3616UB, SUP, NV1023, third generation viruses such as G47Δ, transcriptional expressing vectors such as G92A, d12.CALP, Myb34.5, transgene expressing vectors such as rRP450, and other viruses such as Talimogene laherparepvec (T-Vec). The HSV-1 vectors are the thought to be useful in the treatment of a wide of solid tumors, for example including glioma, melanoma, breast, prostate, colon, ovarian, and pancreatic cancers. The HSV-1 virus infects a broad range of cells types and species, it is cytolytic by nature, the replicative life cycle of the virus results in host cell destruction, it has a well characterised and large genome (152K) but contains many non-essential genes providing up to 30K of space for the insertion of therapeutic genes. Generally, HSV viruses are not mutated in the thymidine kinase gene for safety reasons. Talimogene laherparepvec is an oncolytic herpes virus, which is approved for use in the treatment of melanoma. Other herpes bases viruses include G207, SEP-REHVIR (HSV-1716), by Virttu Biologics, HSV-1 R3616 mutant, HSV-1 1716 mutant, NV1020 (R7020), R3616 mutant (deleted RL1), KM100 mutant has insertions in UL48 (encodes the transactivator tegument protein pUL48 [VP16]) and RL2 genes, G92A, mutants, Myb34.5 and rQNestin34.5.

Poxvirus—Vaccina virus, such as Modified Vaccinia Ankara (MVA) may be employed (Galmiche M C et al., J Gen Virol 78: 3019-3027, 1997), MVA may be replaced with a p14 fusion molecule carrying an inserted scFv directed against the tumor associate antigen MUC-1 (Paul, S et al., Viral Immunol 20: 664-671, 2007) See also rev. in Liang L et al., Viruses 6: 3787-3808, 2014, Hsiao J C et al., J Virol 73: 8750-8761, 1999, rev. in Chen T L and Roffler S, Med Res. Rev. 28: 885-928, 2008 and Kinoshita T et al., J Biochem 144: 287-294, 2008. JX-594, by Jennerex, is a thymidine kinase-deleted Vaccinia virus plus GM-CSF. GL-ONC1 is an attenuated vaccinia virus (Lister strain) that causes regression and elimination of a wide range of solid tumors in preclincal mouse models.

Paramyxovirus (such as measles or Newcastle disease virus),

Measles virus (MeV) is a single-stranded, negative-sense, enveloped (non-segmented) RNA virus of the genus Morbillivirus within the family Paramyxoviridae. Measles virus has two envelope glycoproteins: the hemagglutinin (H) attachment protein and the fusion (F) protein. Attachment, entry and subsequent cell-cell fusion is mediated via 2 measles receptors, CD46 and the signaling lymphocyte activation molecule (SLAM). See for example rev. in Msaouel P et al., Methods Mol Biol 797: 141-162, 2012, Robinson S. and Galanis, E. Expert Opin Biol Ther. 17: 353-363, 2017, Aref S et al., Viruses 8. Pii:E294, 2016); (rev. in Chen T L and Roffler S, Med Res. Rev. 28: 885-928, 2008 and Kinoshita T et al., J Biochem 144: 287-294, 2008), and (Russell S J and Peng K W, Curr Topic Microbiol. Immunol 330: 213-241, 2009, Robinson S and Galanis, E Expert Opin Biol. Ther 17: 353-363, 2017, Aref S et al., Viruses 8. Pii: E294, 2016). Measles virus encoding the human thyroidal sodium iodide symporter or MV-NIS is an attenuated oncolytic Edmonston (Ed) strain of measles virus. Radioactive Iodine imaging provides a novel technique for NIS gene expression monitoring.

Newcastle disease virus may also be employed.

Adenoviridae Adenoviruses are among the most extensively studied viruses being used as oncolytic agents. An array of peptides and proteins have been engineered into virion associated viral proteins to alter the native tropism of the virus (rev. in Verheije M H and Rottier P J M Adv Virol 2012: 798526, 2012). However, all of these are dependent upon viral assembly in the nucleus which presents significant challenges.

Other non-enveloped viruses include Coxsackievirus, Poliovirus and Reovirus. See for example rev. in Altan-Bonnet, N, Curr Opin Microbiol 32: 77-81, 2016 and Chen Y H et al., Cell 160: 619-630, 2015, rev. in Chen T L and Roffler S, Med Res. Rev. 28: 885-928, 2008 and Kinoshita T et al., J Biochem 144: 287-294, 2008 and rev. in Verheije M H and Rottier P J M Adv Virol 2012: 798526, 2012).

There are a numerous adenoviruses for example Ad5-yCD/mutTKSR39rep-hIL12, such as for the treatment of prostate cancer was initiated, CGTG-102 (Ad5/3-D24-GMCSF), by Oncos Therapeutics, for example for the treatment soft tissue sarcomas, Oncorine (H101), CG0070, Enadenotucirev (EnAd) WO2005/118825, OvAd1 and OvAd2 disclosed in WO2008/080003, ONCOS-102, for example for Unresectable Malignant Pleural Mesothelioma, and DNX-2401 for example for glioma.

Cavatak is the trade name for a preparation of wild-type Coxsackievirus A21, useful in the treatment of malignant melanoma. Seneca Valley virus (NTX-010) and (SVV-001), for example for small cell lung cancer and neuroblastoma Reovirus-Reolysin® (pelareorep; Wild-Type Reovirus; Serotype 3 Dearing; Oncolytics Biotech), for example for the treatment of various cancers and cell proliferative disorders.

Vesicular Stomatitis Virus (VSV) VSV is another enveloped virus being explored as on oncolytic agent. See for example Betancourt D et al., J Virol 89: 11786-11800, 2015) and rev. in Hastie E and Grdzelishvili V Z J Gen Virol 93: 2529-2545, 2012).

Proteins Encoded By A Virus

In one embodiment a virus or vector employed in the method of the present disclosure comprises a transgene, for example where the transgene is to replace defective genetic material in the cell, to provide a new or augmented function in the cell, to sensitize the cell to treatment, to block a function in the cell, or to express a therapeutic protein or peptide. In one embodiment the virus employed as the payload according to the present disclosures, comprises a transgene or transgenes, for example encoding an agent independently selected from an RNAi sequence, a protein, polypeptide or peptide (for example an antibody molecule or binding fragment thereof, a chemokine, a cytokine, an immunomodulator, a fluorescent tag or an enzyme).

This includes but is not limited to unique formats that have shown preclinical promise but have lacked an effective and economical means for delivery e.g. peptides, intrabodies and alternative scaffolds (rev. in Boldicke T, Protein Sci 26: 925-945, 2017, Marschall and Dubel, Comput Struct Biotechnol J 14: 304-308, 2016, Miersch and Sidhu F1000Res 5.pii.F1000 Faculty Rev. 1947, 2016, Peptides, Tsomaia Eur J Med Chem 94:459-470, 2015, Marschall ALJ et al, Mabs 7: 1010-1035, 2015, AlDeghaither D et al., J Clin Pharmacol. 55: S4-S20, 2015))) and includes agents with therapeutic effects on the tumor cells tumor stem cells, tumor associated endothelium and tumor associated stroma. Of special interest are molecules that could serve multiple functions, for example as therapeutics, biomarkers and/or diagnostics. The herpes simplex virus thymidine kinase (HSV-TK) gene is a well-established pro-drug converting enzyme with a clinically approved pro-drug (ganciclovir-GCV) see for example Holder et al., Cancer Res. 53: 3475-3485, 1993, Touraine R L et al., Gene Therapy 5: 1705-1711, 1998), In addition, the thymidine kinase protein expression can also be exploited to image and track the activity of the virotherapy during the course of treatment. Positron emission tomography and single photon emission computed tomography are both methods that are routinely used for the detection and monitoring of cancer and cancer therapies and are both viable means to detect the expression of the thymidine kinase protein when an appropriate thymidine kinase substrate is administered (Wang J Q et al., Bioorg Med Chem 13: 549-556, 2005, Tjuvajev J G et al, J Nucl Med 43: 1072-1083, 2002). Alternatively, the NIS gene may be used and has been explored as an agent for diagnostic and therapeutic purposes in oncolytic viruses, much like T K (Miller A and Russell S Expert Opin Biol Ther 16: 15-32, 2016, Ravera S et al., Annu Rev Physiol 79: 261-289, 2017, Portulano et al., Endocr Rev. 35: 106-149, 2014).

In one embodiment antibodies that interact and inhibit RAS or proteins in the RAS signaling pathway are encoded in the virus of the present disclosure, for example as as fusion protein with the GLA-component. RAS genes constitute a multigene family that includes HRAS, NRAS, and KRAS. See for example Bos J L, Cancer Res. 49: 4682-4689, 1989; and Cetin M et al., J Mol Biol. 429:562-573, 2017.

Labels

In one embodiment the payload comprises a fluorescent label, a chemi-lluminescent label, a radio label, an enzyme, a dye or a ligand.

A label in accordance with the present disclosure is defined as any moiety which may be detected using an assay. Non-limiting examples of reporter molecules include enzymes, radiolabels, haptens, fluorescent labels, phosphorescent molecules, chemiluminescent molecules, chromophores, photoaffinity molecules, colored particles or ligands, such as biotin. Label as employed herein also includes tags, for example His-tags, Flag-tags and the like. Labels include biotin, which is the substrate for avidin.

Labels can be linked to the GLA-components by conjugation or fusion. The label be the only payload or in addition to another entity, such as a therapeutic payload.

Label conjugates are suitable for use as diagnostic agents. Diagnostic agents generally fall within two classes, those for use in in vitro diagnostics, and those for use in vivo diagnostic protocols, generally known as "directed imaging." Many appropriate imaging agents are known in the art, as are methods for their attachment to peptides and polypeptides (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is suitable for use in certain embodiments, and technicium$^{99m}$ and/or indium$^{111}$ are particularly suitable due to their low energy and suitability for long range detection. Radioactively labeled peptides and polypeptides may be produced according to well-known methods in the art. For instance, peptides and polypeptides can be iodinated by contact with sodium and/or potassium iodide and a chemical oxidizing agent such as sodium hypochlorite, or an enzymatic oxidizing agent, such as lactoperoxidase. Petides may be labeled with technetium$^{99}$m by ligand exchange process, for example, by reducing pertechnate with stannous solution, chelating the reduced technetium onto a Sephadex column and applying the peptide to this column. Alternatively, direct labeling techniques may be used, e.g., by incubating pertechnate, a reducing agent such as $SNCl_2$, a buffer solution such as sodium-potassium phthalate solution, and the peptide. Intermediary functional groups which are often used to bind radioisotopes which exist as metallic ions to peptide are diethylenetriaminepentaacetic acid (DTPA) or ethylene diaminetetracetic acid (EDTA).

Fluorescent labels suitable for use as payloads include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of payload is that suitable for use in vitro, is where a peptide is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Suitable secondary binding ligands are biotin and avidin and streptavidin compounds. The use of such labels is well known to those of skill in the art and is described, for example, in U.S. Pat. Nos. 3,817,837, 3,850,752, 3,939,350, 3,996,345, 4,277,437, 4,275,149 and 4,366,241.

Other methods are known in the art for the attachment for linking a peptide to its "conjugate partner" Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Peptides or polypeptides may also be reacted with an enzyme in the presence of a coupling agent such as glutaraldehyde or periodate. Conjugates with fluorescein markers are prepared in the presence of these coupling agents or by reaction with an isothiocyanate.

In one embodiment the label is able to stain or label the nucleus of a stem cell.

Combination Therapy

In one embodiment a combination of chemotherapeutic agents employed is, for example a platin and 5-FU or a prodrug thereof, for example cisplatin or oxaplatin and capecitabine or gemcitabine, such as FOLFOX.

In one embodiment the chemotherapy comprises a combination of chemotherapy agents, in particular cytotoxic chemotherapeutic agents.

In one embodiment the chemotherapy combination comprises a platin, such as cisplatin and fluorouracil or capecitabine.

In one embodiment the chemotherapy combination in capecitabine and oxaliplatin (Xelox).

In one embodiment the chemotherapy is a combination of folinic acid and 5-FU, optionally in combination with oxaliplatin.

In one embodiment the chemotherapy is a combination of folinic acid, 5-FU and irinotecan (FOLFIRI), optionally in combination with oxaliplatin (FOLFIRINOX). The regimen consists of: irinotecan (180 mg/m$^2$ IV over 90 minutes) concurrently with folinic acid (400 mg/m$^2$ [or 2×250 mg/m$^2$] IV over 120 minutes); followed by fluorouracil (400-500 mg/m$^2$ IV bolus) then fluorouracil (2400-3000 mg/m$^2$ intravenous infusion over 46 hours). This cycle is typically repeated every two weeks. The dosages shown above may vary from cycle to cycle.

In one embodiment the chemotherapy combination employs a microtubule inhibitor, for example vincristine sulphate, epothilone A, N-[2-[(4-Hydroxyphenyl)amino]-3-pyridinyl]-4-methoxybenzenesulfonamide (ABT-751), a taxol derived chemotherapeutic agent, for example paclitaxel, abraxane, or docetaxel or a combination thereof.

In one embodiment the chemotherapy combination employs an mTor inhibitor. Examples of mTor inhibitors include: everolimus (RAD001), WYE-354, KU-0063794, papamycin (Sirolimus), Temsirolimus, Deforolimus (MK-8669), AZD8055 and BEZ235(NVP-BEZ235).

In one embodiment the combination therapy employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one embodiment the chemotherapy combination employs an AKT inhibitor. Examples of AKT inhibitors include: MK-2206 and AT7867.

In one embodiment the combination employs an aurora kinase inhibitor. Examples of aurora kinase inhibitors include: Aurora A Inhibitor I, VX-680, AZD1152-HQPA (Barasertib), SNS-314 Mesylate, PHA-680632, ZM-447439, CCT129202 and Hesperadin.

In one embodiment the combination therapy employs a p38 inhibitor, for example as disclosed in WO2010/038086, such as N-[4-({4-[3-(3-tert-Butyl-1-p-tolyl-1H-pyrazol-5-yl) ureido]naphthalen-1-yloxy}methyl) pyridin-2-yl]-2-methoxyacetamide.

In one embodiment the combination employs a Bcl-2 inhibitor. Examples of Bcl-2 inhibitors include: obatoclax mesylate, ABT-737, ABT-263(navitoclax) and TW-37.

In one embodiment the chemotherapy combination comprises an antimetabolite such as capecitabine (xeloda), fludarabine phosphate, fludarabine (fludara), decitabine, raltitrexed (tomudex), gemcitabine hydrochloride and cladribine.

In one embodiment the combination therapy comprises ganciclovir, which may assist in controlling immune responses and/or tumour vasculation.

In one embodiment the chemotherapy includes a PARP inhibitor.

In one embodiment the combination therapy includes an inhibitor of cancer metabolism with specific inhibition of the activity of the DHODH enzyme.

In one embodiment one or more therapies employed in the method herein are metronomic, that is a continuous or frequent treatment with low doses of anticancer drugs, often given concomitant with other methods of therapy.

In one embodiment, there is provided the use of multiple cycles of treatment (such as chemotherapy) for example 2, 3, 4, 5, 6, 7, 8.

In one embodiment the chemotherapy is employed in a 28 day cycle.

The GLA-components of the present disclosure can be adapted to treated one or more of the following infections by targeting extracellular vesicles derived from infected cells: *Acinetobacter* infections (*Acinetobacter baumanni*), Actinomycosis (*Actinomyces israelii, Actinomyces gerencseriae* and *Propionibacterium propionicus*), African sleeping sickness also known as African trypanosomiasis (*Trypanosoma brucei*) AIDS-Acquired immunodeficiency syndrome (HIV (Human immunodeficiency virus)), Amebiasis (*Entamoeba histolytica*), Anaplasmosis (*Anaplasma* species), Angiostrongyliasis (*Angiostrongylus*), Anisakiasis (*Anisakis*), Anthrax (*Bacillus anthracis*), Arcanobacterium haemolyticum infection (*Arcanobacterium haemolyticum*), Argentine hemorrhagic fever (Junin virus), Ascariasis (*Ascaris lumbricoides*), Aspergillosis (*Aspergillus* species), Astrovirus infection (Astroviridae family), Babesiosis (*Babesia* species), *Bacillus cereus* infection (*Bacillus cereus*), Bacterial pneumonia (multiple bacteria), Bacterial vaginosis (bacterial vaginosis microbiota), *Bacteroides* infection (*Bacteroides*), Balantidiasis (*Balantidium coli*), Bartonellosis (*Bartonella*), Baylisascaris infection (*Baylisascaris*), BK virus infection (BK virus), Black piedra (Piedraia hortae), Blastocystosis (*Blastocystis*), Blastomycosis (*Blastomyces dermatitidis*), Bolivian hemorrhagic fever (Machupo virus), Botulism and Infant botulism (*Clostridium botulinum*; Note: Botulism is not an infection by *Clostridium botulinum* but caused by the intake of botulinum toxin), Brazilian hemorrhagic fever (Sabiá virus), Brucellosis (*Brucella*), Bubonic plague (Enterobacteriaceae), Burkholderia infection (*Burkholderia*), Buruli ulcer (*Mycobacterium ulcerans*), Calicivirus infection (Caliciviridae (Norovirus and Sapovirus)), Campylobacteriosis (*Campylobacter*), Candidiasis also known as Thrush (*Candida*), Capillariasis (Intestinal disease by Capillaria *philippinensis*, hepatic disease by Capillaria *hepatica* and pulmonary disease by Capillaria aerophila), Carrion's disease (*Bartonella bacilliformis*), Cat-scratch disease (*Bartonella henselae*), Cellulitis (usually Group A *Streptococcus* and *Staphylococcus*), Chagas Disease also known as American trypanosomiasis (*Trypanosoma cruzi*), Chancroid (*Haemophilus ducreyi*), Chickenpox (Varicella zoster virus), Chikungunya (Alphavirus), Chlamydia (*Chlamydia trachomatis*), Chlamydophila pneumoniae infection also known as TWAR (*Chlamydophila pneumoniae*), Cholera (*Vibrio cholerae*), Chromoblastomycosis (*Fonsecaea pedrosoi*), Chytridiomycosis (*Batrachochytrium dendrabatidis*), Clonorchiasis (*Clonorchis sinensis*), Clostridium difficile colitis (*Clostridium difficile*), Coccidioidomycosis (*Coccidioides immitis* and *Coccidioides posadasii*), Colorado tick fever (Colorado tick fever virus), Common cold/Acute viral rhinopharyngitis/Acute coryza (usually rhinoviruses and coronaviruses), Crimean-Congo hemorrhagic fever (Crimean-Congo hemorrhagic fever virus), Cryptococcosis (*Cryptococcus neoformans*), Cryptosporidiosis (*Cryptosporidium*), Cutaneous larva migrans (usually *Ancylostoma braziliense* and multiple other parasites), Cyclosporiasis (*Cyclospora cayetanensis*), Cysticercosis (*Taenia solium*), Cytomegalovirus infection (Cytomegalovirus), Dengue fever (Dengue viruses such as DEN-1, DEN-2, DEN-3 and DEN-4), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus), Echinococcosis (*Echinococcus*), Ehrlichiosis (*Ehrlichia*), Enterobacteriaceae (Carbapenem-resistant Enterobacteriaceae), Enterobiasis (*Enterobius vermicularis*), Enterococcus infection (*Enterococcus*), Enterovirus (Enterovirus), Epidemic typhus (*Rickettsia prowazekii*), Erythema infectiosum (Parvovirus B19), Exanthem subitum (Human herpesvirus 6 (HHV-6) and Human herpesvirus 7 (HHV-7)), Fasciolasis (*Fasciola hepatica* and *Fasciola gigantica*), Fasciolopsiasis (*Fasciolopsis buski*), Filariasis (Filarioidea), Food poisoning by *Clostridium perfringens* (*Clostridium perfringens*), Free-living amebic infection (various pathogens), *Fusobacterium* infection (*Fusobacterium*), Gas gangrene (usually *Clostridium* such as *perfringens*), Geotrichosis (*Geotrichum candidum*), Giardiasis (*Giardia lamblia*), Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*), Hand, foot and mouth disease (Enteroviruses, mainly Coxsackie A virus and Enterovirus 71 (EV71)), Hantavirus Pulmonary Syndrome (Sin Nombre virus), Heartland virus disease (Heartland virus), *Helicobacter pylori* infection (*Helicobacter pylori*), Hemolytic-uremic syndrome (*Escherichia coli* such as 0157:H7, 0111 and 0104:H4), Hemorrhagic fever with renal syndrome (Bunyaviridae family), Hepatitis A (Hepatitis A virus), Hepatitis B (Hepatitis B virus), Hepatitis C (Hepatitis C virus), Hepatitis D (Hepatitis D Virus), Hepatitis E (Hepatitis E virus), Herpes simplex (Herpes simplex virus 1 and 2 (HSV-1 and HSV-2), Histoplasmosis (*Histoplasma capsulatum*), Hookworm infection (*Ancylostoma duodenale* and *Necator americanus*), Human bocavirus infection (Human bocavirus), Human *ewingii* ehrlichiosis (*Ehrlichia ewingii*), Human granulocytic anaplasmosis (*Anaplasma phagocytophilum*), Human metapneumovirus infection (Human metapneumovirus), Human monocytic ehrlichiosis (*Ehrlichia chaffeensis*), Human papillomavirus infection (Human papillomavirus), Human parainfluenza virus infection (Human parainfluenza viruses), Hymenolepiasis (*Hymenolepis nana* and *Hymenolepis diminuta*), Epstein-Barr virus infectious mononucleosis (Epstein-Barr virus), Influenza (Orthomyxoviridae), Isosporiasis (*Isospora belli*), Kawasaki disease, Keratitis (various pathogens), *Kingella kingae* infection (*Kingella kingae*), Lassa fever (Lassa virus), Legionellosis also known as Legionnaires' disease (*Legionella pneumophila*), Legionellosis also known asPontiac fever (*Legionella pneumophila*), Leishmaniasis (*Leishmania*), Leprosy (*Mycobacterium leprae* and *Mycobacterium lepromatosis*), Leptospirosis (*Leptospira*), Listeriosis (*Listeria monocytogenes*), Lyme disease (*Borrelia burgdorferi*, *Borrelia garinii*, and *Borrelia afzelii*), Lymphatic filariasis (*Wuchereria bancrofti* and *Brugia malayi*), Lymphocytic choriomeningitis (Lymphocytic choriomeningitis virus), Malaria (*Plasmodium*), Marburg hemorrhagic fever (Marburg virus), Measles (Measles virus), Middle East respiratory syndrome (Middle East respiratory syndrome coronavirus), Melioidosis (*Burkholderia pseudomallei*), Meningitis (various), Meningococcal disease (*Neisseria meningitidis*), Metagonimiasis (usually *Metagonimus yokagawai*), Microsporidiosis (Microsporidia phylum), Molluscum contagiosum (Molluscum contagiosum virus), Monkeypox (Monkeypox virus), Mumps (Mumps virus), Murine typhus (*Rickettsia typhi*), *Mycoplasma* pneumonia (*Mycoplasma pneumoniae*), Mycetoma (Actinomycetoma) and fungi Eumycetoma), Myiasis (parasitic dipterous fly larvae), Neonatal conjunctivitis (most commonly *Chlamydia trachomatis* and *Neisseria gonorrhoeae*), Norovirus infection (Norovirus), Nocardiosis (*Nocardia* such as *N. asteroides*), Onchocerciasis (*Onchocerca volvulus*), Opisthorchiasis (*Opisthorchis viverrini* and *Opisthorchis felineus*), Paracoccidioidomycosis (*Paracoccidioides brasiliensis*), Paragonimiasis (*Paragonimus* such as *westermani*), Pasteurellosis (*Pasteurella*), Pelvic inflammatory disease (various pathogens), Pertussis (*Bordetella pertussis*), Plague (*Yersinia pestis*), Pneumococcal infection (*Streptococcus pneumoniae*), *Pneumocystis* pneumonia (*Pneumocystis jirovecii*), Pneumonia (various pathogens), Poliomyelitis (Poliovirus), *Prevotella* infection (*Prevotella*), Primary amoebic meningoencephalitis (usually *Naegleria fowleri*), Progressive multifocal leukoencephalopathy (JC virus), Psittacosis (*Chlamydophila psittaci*), Q fever (*Coxiella burnetii*), Rabies (Rabies virus), Relapsing fever (*Borrelia* such as *B. hermsii* and *B. recurrentis*), Respiratory syncytial virus infection (Respiratory syncytial virus), Rhinosporidiosis (*Rhinosporidium seeberi*), Rhinovirus infection (Rhinovirus), Rickettsial infection (*Rickettsia* species), Rickettsialpox (*Rickettsia akari*), Rift Valley fever (Rift Valley fever virus), Rocky Mountain spotted fever (*Rickettsia rickettsii*), Rotavirus infection (Rotavirus), Rubella (Rubella virus), Salmonellosis (*Salmonella*), Severe Acute Respiratory Syndrome (SARS coronavirus), Schistosomiasis (*Schistosoma*), Sepsis (various pathogens), Shigellosis (*Shigella*), Shingles (Varicella zoster virus), Smallpox (Variola major or Variola minor), Sporotrichosis (*Sporothrix schenckii*), Staphylococcal food poisoning (*Staphylococcus*), Staphylococcal infection (*Staphylococcus*), Strongyloidiasis (*Strongyloides stercoralis*), Subacute sclerosing panencephalitis (Measles virus), Syphilis (*Treponema pallidum*), Taeniasis (*Taenia*), Tetanus (*Clostridium tetani*), Tinea barbae (usually *Trichophyton*), Tinea capitis (*Trichophyton tonsurans*), Tinea corporis (usually *Trichophyton*), Tinea cruris (usually *Epidermophyton floccosum*, *Trichophyton rubrum*, and *Trichophyton mentagrophytes*), Tinea manum (*Trichophyton rubrum*), Tinea nigra (usually *Hortaea werneckii*), Tinea pedis (usually *Trichophyton*), Tinea unguium (usually *Trichophyton*), Tinea *versicolor* (*Malassezia*), Toxocariasis (*Toxocara canis* or *Toxocara cati*), Trachoma (*Chlamydia trachomatis*), Toxoplasmosis (*Toxoplasma gondii*), Trichinosis (*Trichinella spiralis*), Trichomoniasis (*Trichomonas vaginalis*), Trichuriasis (*Trichuris trichiura*), Tuberculosis (usually *Mycobacterium tuberculosis*), Tularemia (*Francisella tularensis*), Typhoid fever (*Salmonella enterica* subsp. *enterica*, serovar *typhi*), Typhus fever (*Rickettsia*), Ureaplasma urealyticum infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), *Vibrio vulnificus* infection (*Vibrio vulnificus*), *Vibrio parahaemolyticus* enteritis (*Vibrio parahaemolyticus*), Viral pneumonia (various viruses), West Nile Fever (West Nile virus), White *piedra* (*Trichosporon beigelii*), *Yersinia pseudotuberculosis* infection (*Yersinia pseudotuberculosis*), Yersiniosis (*Yersinia enterocolitica*), Yellow fever (Yellow fever virus) and Zygomycosis (Zygomycetes).

Intracellular Pathogens

Intracellular cellular pathogens, can be some of the most difficult to treat because once the pathogen is inside the cell some level of protection may be provided to the pathogen by the cellular environment.

Pathogens, may be viral, bacterial, fungal, protozoan etc. The molecules are the present disclosure are particularly useful for treatment of intracellular pathogens, in particular those disclosed herein.

Notable intracellular bacteria include *Bartonella henselae, Francisella tularensis, Listeria monocytogenes, Salmonell typhi, Brucella, Legionella, Mycobacterium* (such as *Mycobacterium tuberculosis*), *Nocardia, Rhodococcus equi, Yersinia, Neisseria* meninggitidis.

One or more antibiotics selected from erythromycin, doxycycline, azithromycin, rifampin, streptomycin, gentamicin, doxycycline, ciprofloxacin, ampicillin, trimethoprim-sulfamethoxazole, chloramphenicol, TMP-SMZ (trimethoprim-sulfamethoxazole), levofloxacin, moxifloxacin, clarithromycin, tetracyclines, glycylcyclines, ethambutol, rifabutin, imipenem, cefotaxime, amikacin, vancomycin, minocycline, penicillin G, ampicillin, fluoroquinolone, aztreonam and combinations of two or more of the same.

*Mycobacterium tuberculosis* is notoriously difficult to treat. In one independent aspect the present disclosure provides a molecule for the treatment of latent and/or active TB where one or more TB drugs are conjugated as a payload to the GLA-component described herein.

The molecules of the present disclosure may be able to greatly increased the efficacy of current medicines by delivering them to inside the cell where the *mycobacterium* is located.

The treatment for TB depends on a number of factors, including whether the TB is latent or active, if the patient is an adult, is a child, is pregnant, is HIV positive or a combination of the above. The details below relate to all aspects of the invention, for example what molecules to prepare and how to use them to treat patients.

Treatment of Latent TB in HIV patients and children in the age range 2 to 11 is isoniazid daily for 6 to 9 months. Pregnant patients may be treated twice weekly as opposed to daily.

Thus, in one embodiment in the molecule of the present disclosure the GLA-component is linked to a payload comprising isoniazid or a an equivalent thereof. Treatment of Latent TB in patients 12 years or older without complicating factors may be given isoniazid and rifapentine one a week for 3 months. Alternatively, rifampin may be given daily for 4 months.

This in one embodiment the payload further comprises rifapentine.

Alternatively, a molecule may be provided where the GLA domain, as described herein, is linked to payload comprising rifapentine. A combination of molecules according to the present disclosure may be provided for use in treatment.

First line treatment for active TB is often selected from isoniazid, rifampin, ethambutol, pyrazinamide and combinations of two or more of the same.

Thus, in there is provide a molecule according to the present disclosure comprising a GLA-component, as described herein, linked to a payload comprising rifampin.

Also provided a molecule according to the present disclosure comprising a GLA-component, as described herein, linked to a payload comprising ethambutol.

In a further embodiment there is provided a molecule according to the present disclosure comprising a GLA-component, as described herein, linked to a payload comprising pyrazinamide.

As explicitly envisaged that the payloads used in the treatment of TB employing extracellular vesicles as disclosed herein may comprise two or more, such as three drugs or four drugs, such as: isoniazid and rifamycin, isoniazid and pyraxinamide, isoniazid and ethambutol, rifamycin and pyraxinamide, rifamycin and ethambutol, pyraxinamide and ethambutol, isoniazid and rifamycin and pyraxinamide, isoniazid and rifamycin and ethambutol, and isoniazid and rifamycin and pyraxinamide and ethambutol.

Viral pathogens include influenza, human immunodeficiency virus, dengue virus, West Nile virus, smallpox virus, respiratory syncytial virus, Korean hemorrhagic fever virus, chickenpox, varicella zoster virus, herpes simplex virus 1 or 2, Epstein-Barr virus, Marburg virus, hantavirus, yellow fever virus, hepatitis A, B, C or E, Ebola virus, human papilloma virus, rhinovirus, Coxsackie virus, polio virus, measles virus, rubella virus, rabies virus, Newcastle disease virus, rotavirus, HIV (such HTLV-1 and -2).

Antiviral drugs may be linked to the GLA-component may be independently be selected from one or more of the following: Abacavir, Aciclovir, Acyclovir, Adefovir, Amantadine, Amprenavir, Ampligen, Arbidol, Atazanavir, Atripla, Boceprevirertet, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Synergistic enhancer (antiretroviral), Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir and Zidovudine.

It is well known in the technical field that antiviral drugs may be used in combinations, for example to increase effectiveness.

Thus, in one embodiment the molecule of the present invention is provided with a payload to treat a protozoan disease, for example malaria, African sleeping sickness and the like.

Notable protozoan parasite include plasmodium type parasites, such as malaria. Drug used treat malaria, such as quinine and related agents, choloroquine, amodiaquine, pyrimethamine, proguanil, sulphonamides, mefloquine, atovaquone, primaquine, aremisinin and derivates thereof, halofantrine, doxycycline, clindamycin, sulfadiazine and combination of two or more of the same.

In one embodiment the molecules of the present disclosure are provided in a pharmaceutical composition comprising a excipient, diluent and/or carrier. In one embodiment the composition is as a parenteral formulation.

Parenteral formulation means a formulation designed not to be delivered through the GI tract. Typical parenteral delivery routes include injection, implantation or infusion.

In one embodiment the parenteral formulation is in the form of an injection. Injection includes intravenous, subcutaneous, intra-cranial, intrathecal, intra-tumoural or intra-muscular injection. Injection as employed herein means the insertion of liquid into the body via a syringe.

In one embodiment the parenteral formulation is in the form of an infusion.

Infusion as employed herein means the administration of fluids at a slower rate by drip, infusion pump, syringe driver or equivalent device. In one embodiment, the infusion is administered over a period in the range of 1.5 minutes to 120 minutes, such as about 3, 4, 5, 6, 7, 8, 9, 10, 11, 12, 13, 14 15, 16, 17, 18, 19 20, 25, 30, 35, 40, 45, 50, 55, 60, 65, 70, 65, 80, 85, 90, 95, 100, 105, 110 or 115 minutes.

In one embodiment, the formulation is for intravenous (i.v.) administration. This route is particularly effective because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

As discussed above the formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

Thus, in embodiment there is provided a molecule according to the present disclosure where the GLA-component, described herein, is linked to a payload comprising one or more anti-malaria drugs.

"Comprising" in the context of the present specification is intended to mean "including".

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

The technical backgrounds is part of the technical disclosure of the present specification and may be used as basis for amendments because the discussion therein is not limited to discussing the prior art as it also includes a discussion of the technical problems encountered in the field and the application of the present invention. a.

Any embodiments specifically and explicitly recited herein may form the basis of a disclaimer either alone or in combination with one or more further embodiments.

The present application claims priority from US serial numbers: 62/554530, 62/569,403, 62/554533, 62/569,411, 62/584,565 and 62/593,014. Each of these applications are incorporated by reference. These applications may be employed as the basis for a correction to the present specification.

The invention will now be described with reference to the following examples, which are merely illustrative and should not in any way be construed as limiting the scope of the present invention.

EXAMPLES

FIG. 1A-D Shows various representations of GLA protein structures.

FIG. 1E Shows an embodiment of a GLA-component according to the present disclosure.

FIG. 2 Shows Protein S (PrS) and annexin staining of breast cancer cell lines treated with peroxide to induce apoptosis. A, human MDA-231 cells treated with peroxide and stained with FITC-PrS. B, untreated MDA-231 cells stained as in A. C, treated MDA-231 cells stained with annexin. D, human MCF-7 cells treated with peroxide and stained with PrS. E, murine MET-1 cells, as in D. F, murine 4T1 cells, as in D.

FIG. 3 Shows overlapping, yet distinct, cellular localization of PrS and annexin. A, murine 4T1 cells treated with peroxide and stained with Cy5 PrS ("RED") and FITC annexin ("GREEN"). Light arrow, co-localized signals; red arrows, cells staining with PrS and not annexin; green arrow, cell staining relatively brighter with annexin but less bright with PrS, indicating distinct binding patterns (insets show PrS and annexin staining separately). B, treated 4T1 cells stained with FITC PrS and Cy5 annexin. Green arrows, cells staining with PrS and not annexin. C, Cy5 annexin staining of treated 4T1 cells pre-incubated with 1,000-fold excess of cold annexin.

FIG. 4 Shows staining of apoptotic COS-1 cells with PrS and annexin. Cells were treated with t-BHP as described and stained with FITC annexin (left) and Cy5 PrS (right). Arrows indicate sub cellular structures presumed to be apoptotic bodies.

FIG. 5 Shows differential staining of extracellular vesicles with PrS and annexin. Extracellular vesicles were prepared from 4T1 cells and stained with FITC PrS ("GREEN") and Cy5 annexin ("RED"). Arrows indicate vesicles staining with annexin only ("RED" arrow), PrS only ("GREEN" arrow) and both proteins (light arrow).

FIG. 6 Shows subcellular localization of PrS and annexin. A, B, apoptotic 4T1 cells were stained with FITC PrS ("GREEN" arrows) and Cy5 annexin ("RED" arrows); light arrows, co-localization. C, Possible apoptotic bodies.

FIG. 7 Shows internalization of PrS within 5 minutes. Apoptotic 4T1 cells were stained with FITC PrS ("green") and Cy5 annexin ("red") and imaged within 10 min of the addition of the proteins. A, Merged image. B, Hoescht nuclear stain alone.

FIG. 8 Shows BLI images of 4T1 tumors in mice.

FIG. 9 SPECT imaging of effect of doxorubicin on 4T1 tumors, using radiolabeled PrS and annexin. Mice with 4T1 breast cancer tumors were imaged with 99mTc PrS (A and B), or annexin (C and D), before (A and C) and 24 h after doxorubicin (B and D).

FIG. 10 Shows SPECT imaging of cyclohexamide-treated mice. Five mice per panel are shown before (A and C) and 24 h after (B and D) treatment. The mice were imaged with either $^{99m}$Tc PrS (A and B), or annexin (C and D), Arrows indicate increased liver signal.

FIG. 11 Shows localization of Cy5 PrS to infected spleen. CD1 mice were infected with bioluminescent Listeria and imaged on day 2 post infection. The mice were injected with Cy5 PrS 30 min before sacrifice, and the spleens removed and frozen. Modestly infected (A) and control uninfected (C) mice are shown. Sections of the infected (B) and uninfected (D) spleens of each mouse in the Cy5 channel are shown, merged with phase contrast images.

FIG. 12 Shows localization of Cy5 PrS to tumors treated with doxorubicin. Mice implanted with 4T1 breast cancer tumors were treated with doxorubicin (right panels) or left untreated (left panels). 24 hours later the mice were injected intravenously with Cy5 PrS and sacrificed 30 min later. The tumors were removed, frozen, and sectioned for fluorescence microscopy. Merged Cy5/phase contrast images from four different mice are shown.

FIG. 13 Shows differentiation of TSCs. TSCs were cultured in the presence (left) or absence (right) of growth factors. Arrows in the right panel indicate giant cells characteristic of differentiation.

FIG. 14 Shows PrS staining of trophoblast stem cells and differentiated trophoblasts. Trophoblast stem cells (left) were differentiated into trophoblast giant cells (right) by withdrawal of growth factors. The cells were stained with Cy5 PrS and imaged.

FIG. 15 Shows MSC differentiation. MSC were treated as described in the text, for differentiation into adipocytes (upper panels) or osteoblasts (lower panels). Differentiated cells exhibited the expected morphology in each case.

Figure 17:
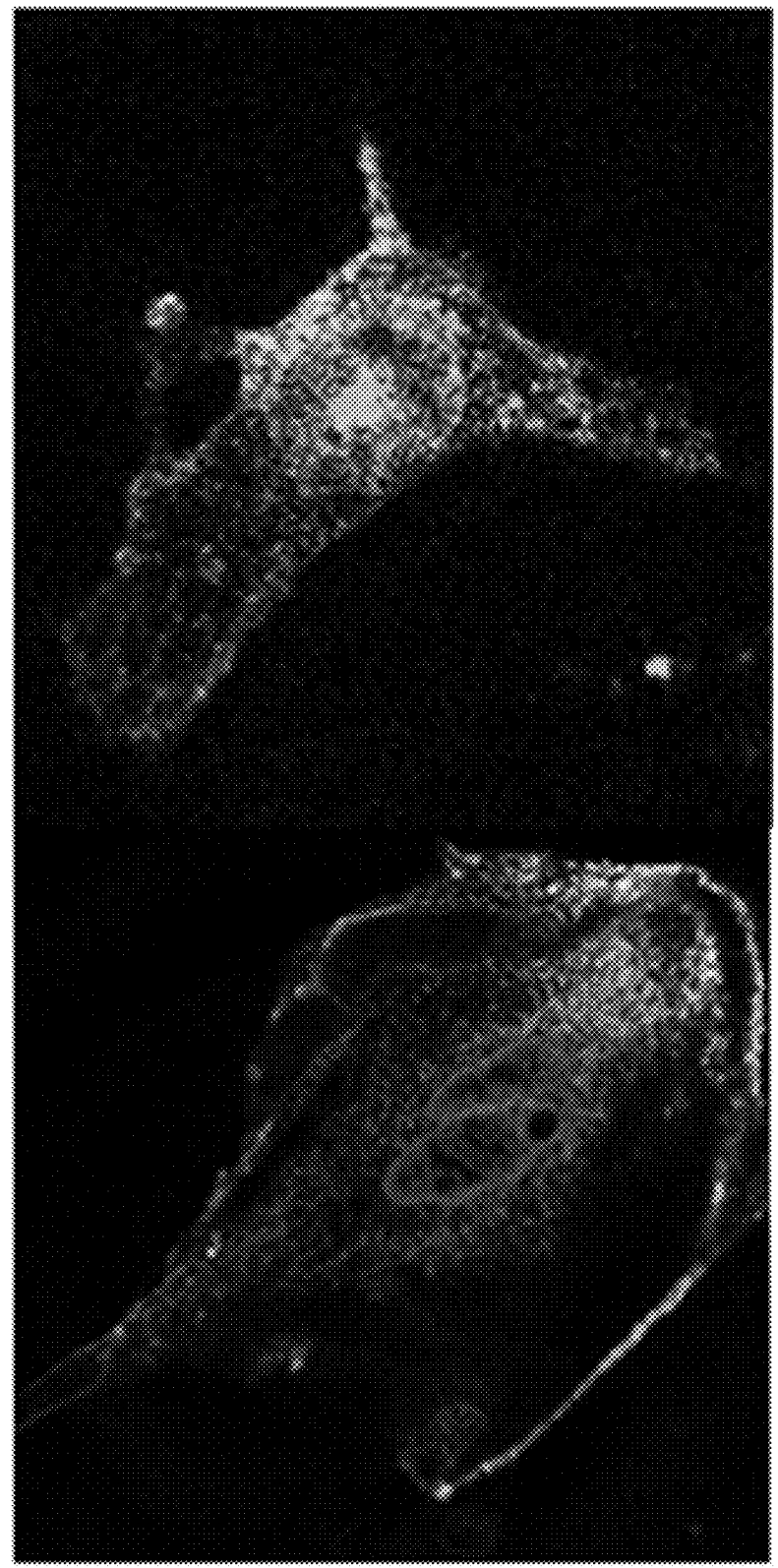
FIG. 17 Shows TSCs stained with PrS (green, lightest area), annexin (red, light around the cell membrane), and Hoechst (blue). Cells were imaged within 5 min of addition of the stain mixture.
Figure 18:
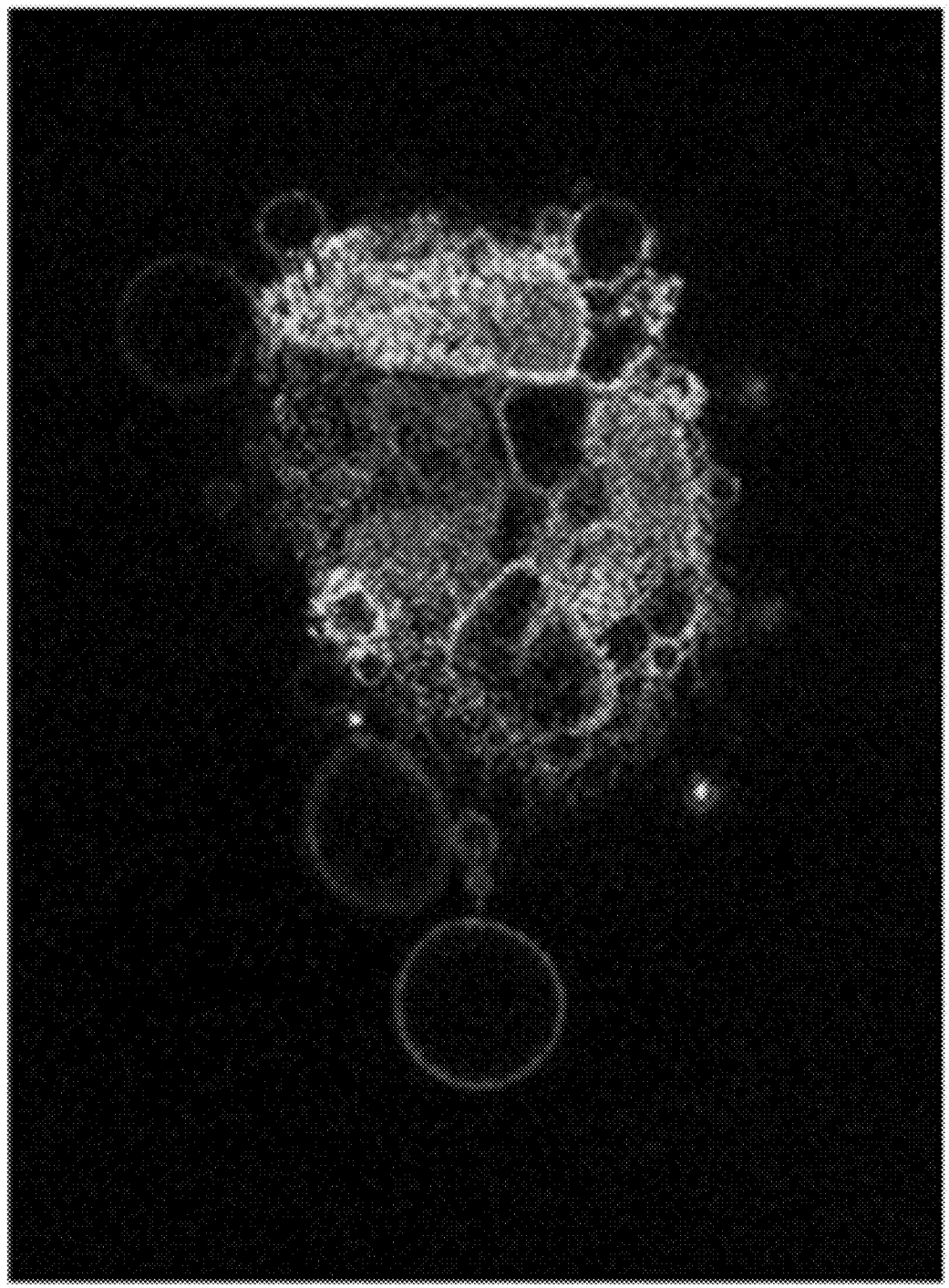

FIG. 18 Shows differential staining of TSC vesicles. TSCs were stained as in FIG. 17. The group of cells are secreting large vesicles that stain with annexin (red) and not PrS (green).

Figure 19:
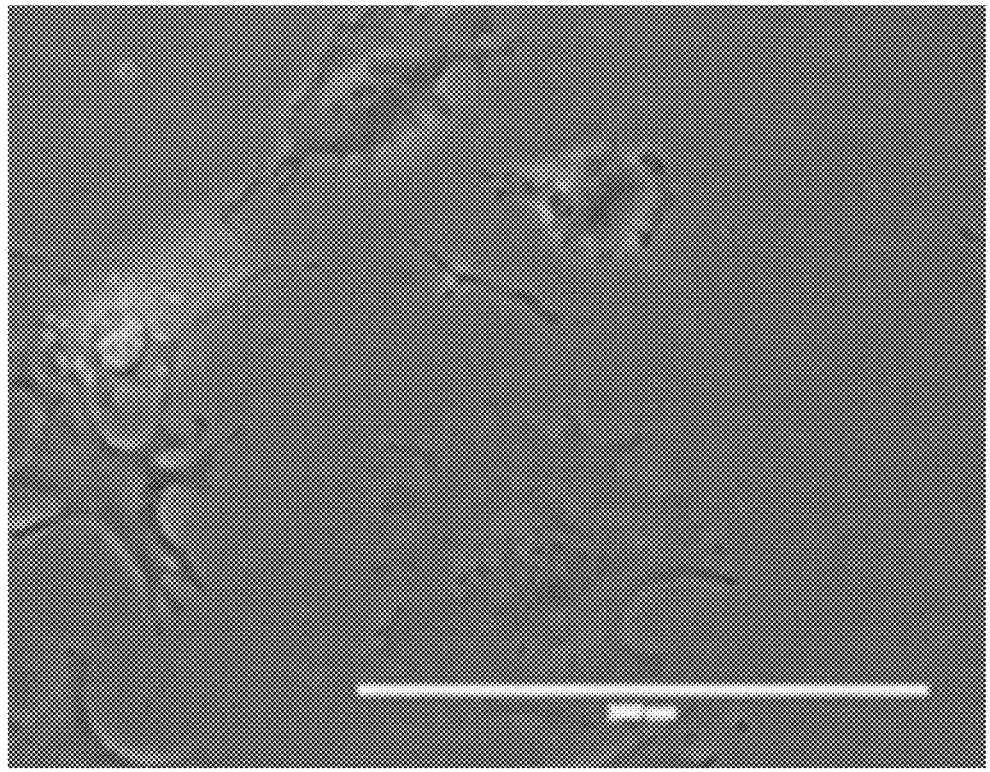

FIG. 19 Shows PrS staining of C17.2 neural progenitor cells. The cells were stained with PrS-FITC and imaged with standard (non-confocal) microscopy.

Figure 20:

FIG. 20 Shows internalization of PrS into TSC at 4C. FITC PrS (green) and Cy5 annexin (red) were added to TSC at 4C and imaged with confocal microscopy.

Figure 21:
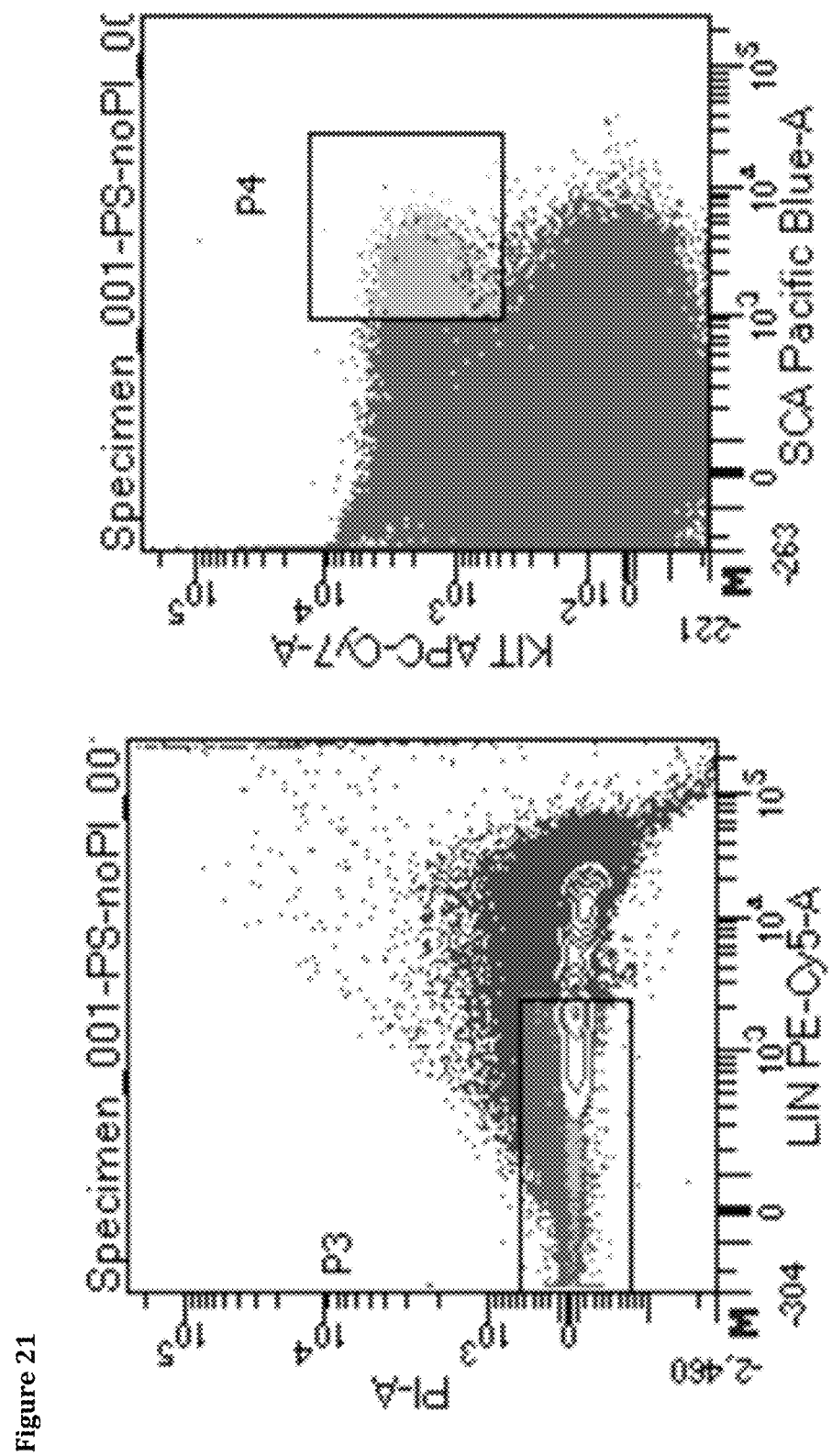

FIG. 21 Shows lineage-negative, SCA-1/c-kit staining cells from mouse bone marrow. The cells were not stained with either PI (propidium iodide; to detect dead cells) or PrS at this point in the analysis. Absence of staining for hematopoietic lineages (left panel) and staining of c-kit and SCA1 (right panel) defines the population of HSC, shown in green (lightest areas).

Figure 22:
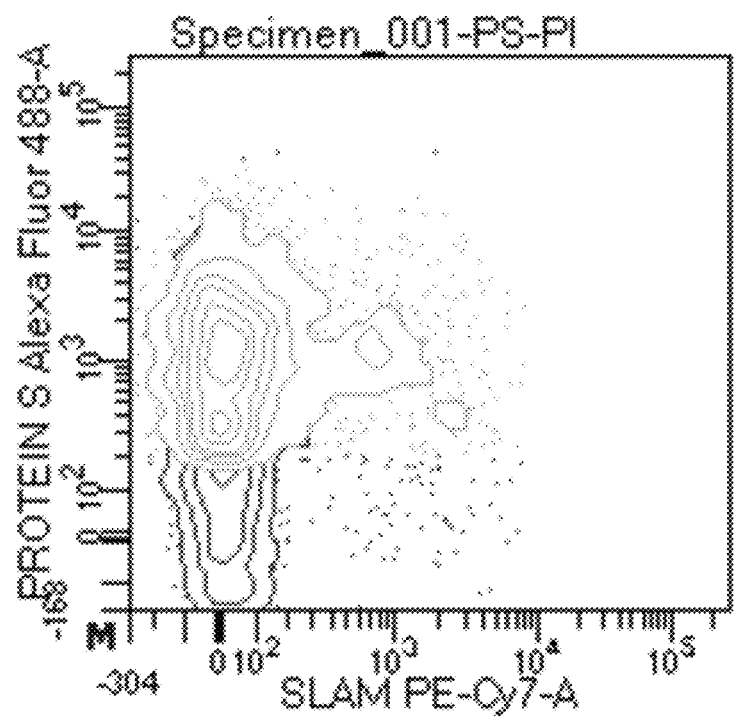

FIG. 22 PrS staining of long-term HSC. HSC were isolated as in FIG. 1, and stained with FITC PrS. SLAM pattern was determined with Cy7 (x-axis).

Figure 23:
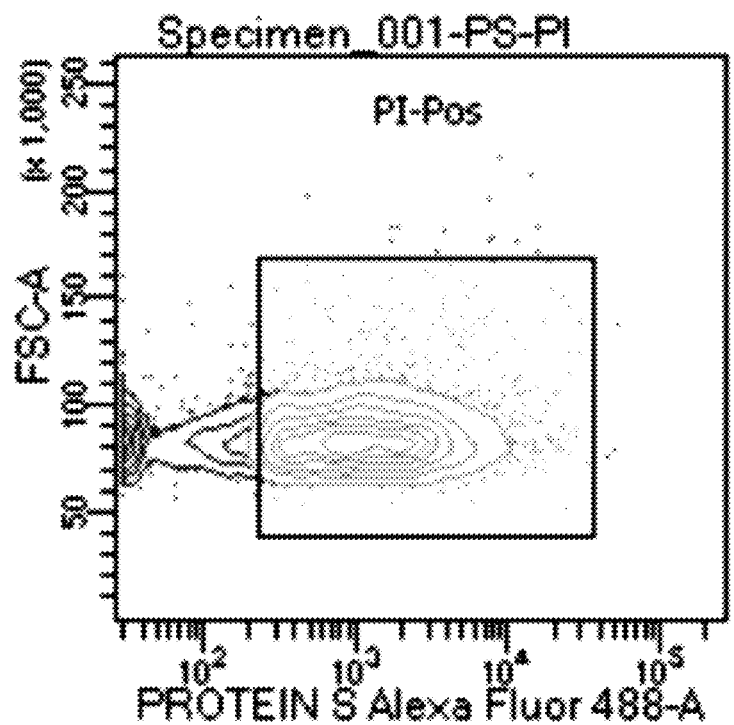

FIG. 23 PrS staining of short-term HSC. HSC were isolated as in FIG. 1, and stained with FITC PrS. SLAM pattern was determined with Cy7 (x-axis).

Figure 24:
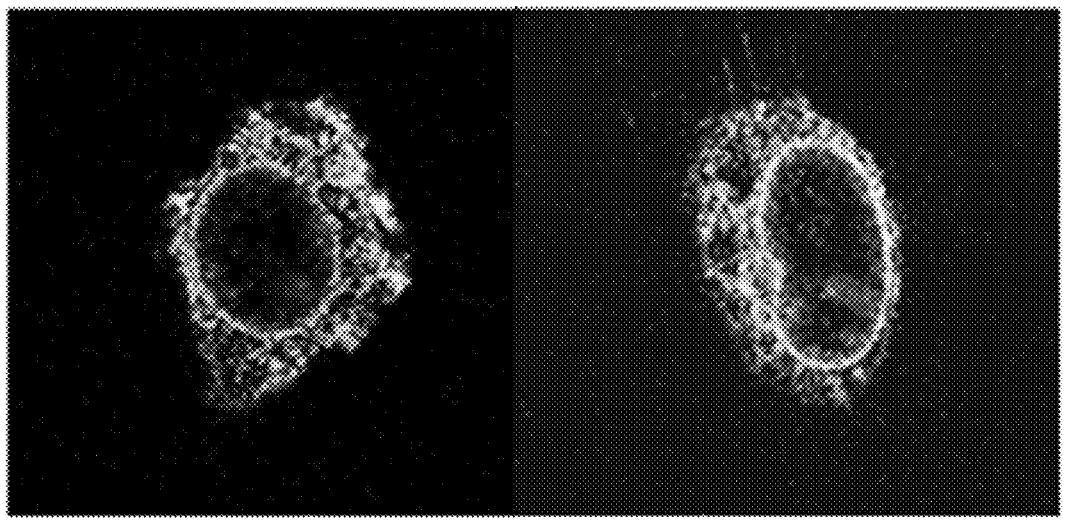

FIG. 24 Shows internalization of PrS in long-term HSC. HSC were prepared as described, stained for PrS, and examined with confocal microscopy. Green (lightest areas), FITC PrS; blue, Hoescht nuclear stain; red, PI. Note that PI stain is excluded from the nucleus, indicating the cells are alive.

Figure 25:
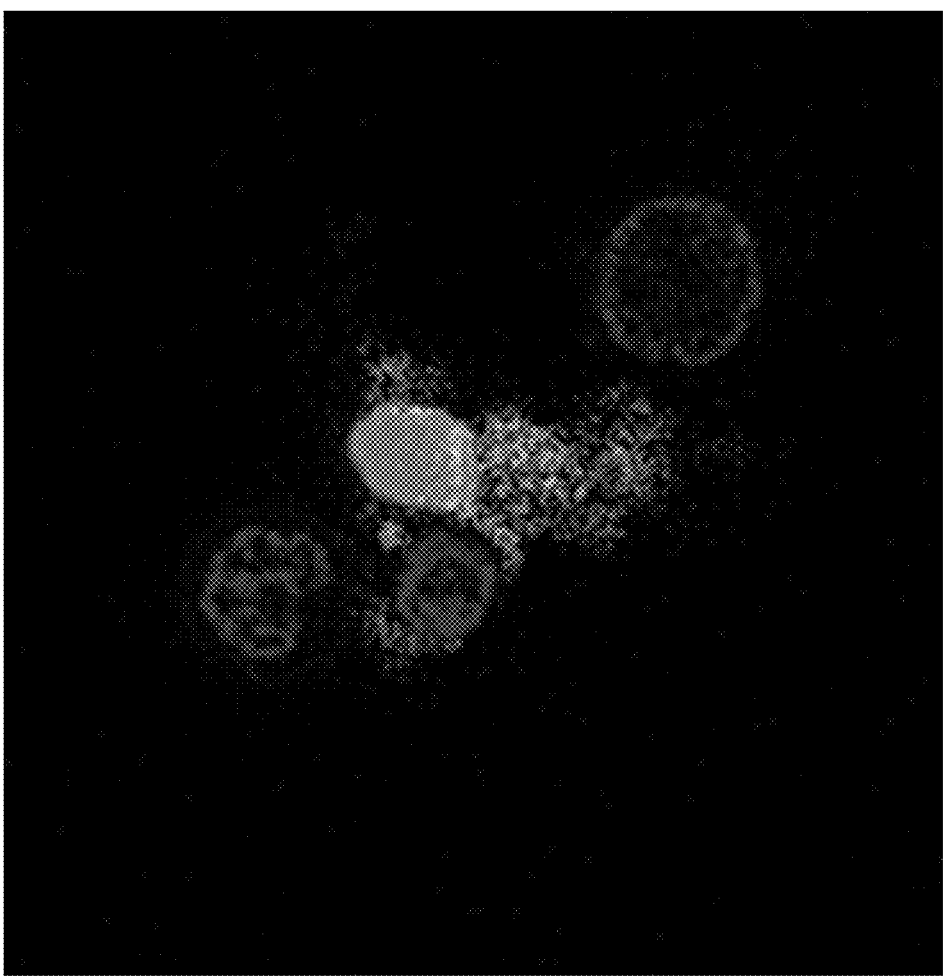

FIG. 25 Shows an example of dead HSC exhibiting nuclear PI.

Figure 26:
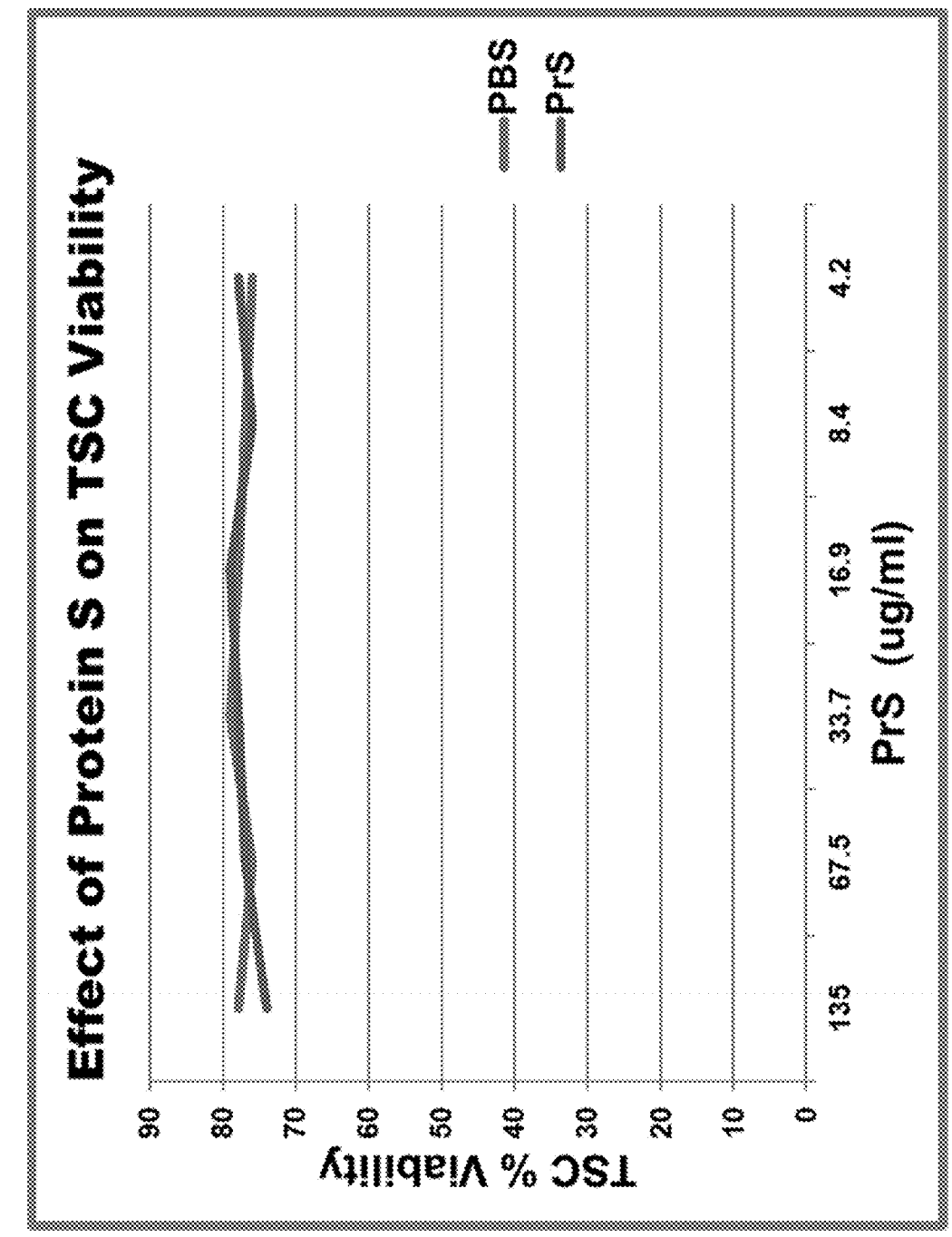

FIG. 26 GLA-mediated delivery is non-toxic to cells

This specification also includes sequences 1 to 6, in the associated sequence listing.

This project initiated the testing of labeled recombinant PrS as an in vivo imaging agent for SPECT (Single Photon Computed Tomography). Surprisingly it was found that the molecule rapidly internalized into apoptotic cells. This unexpected finding led us to explore the phenomenon further, whereupon we found that PrS was also internalized into a subset of non-apoptotic stem cells of several types.

PrS is protein S GLA domain and protein S EGF domain as shown in SEQ ID NO: 6.

Methods

For fluorescence, conjugation of Cy5 and FITC was achieved using Amersham (GE Heathcare) and Molecular Probes (Invitrogen) labeling kits, respectively, according to the instructions of the manufacturers. Both kits provide columns for the removal of unconjugated fluorophore. Initially, 0.77 mg of PrS (Fraction 2) in 1 ml and 0.77 mg of annexin in 1 ml were labeled with FITC to test for specificity of binding to apoptotic cells. For co-localization and competition studies 0.68 mg of PrS (Fraction 3) in 1 ml and 0.68 mg of annexin were labeled with Cy5. For confocal microscopy, 0.76 mg of PrS from the second shipment was labeled with FITC and the previously labeled Cy5-conjugated annexin was used. It should be noted that the precise efficiency of labeling was not determined and the recovery from the columns was assumed to be 85%, according to the instructions of the manufacturers of the labeling kits. Thus, the relative staining intensity of the two proteins in any case may reflect these contingencies. The cells were stained for 30 min initially, but it was subsequently determined that less than 5 min was sufficient. To test PrS for apoptotic cell-specificity, four breast cancer cell lines were initially employed; human MDA-231 and MCF7 and murine 4T1 and MET-1. Subsequently, COS-1 monkey kidney cells were also used. Apoptosis was induced with hydrogen peroxide or tertiary-Butyl hydroperoxide (t-BHP). The cells were plated in 24-well plates at $6\times10^4$ cells per well or Eppendorf chamber slides at $1\times10^4$ cells per well, and apoptosis was induced the next day, using 2 mM $H_2O_2$, or t-BHP for time points from 30 min to 2 hrs. After induction, the wells were washed with Annexin Binding Buffer (AB; Santa Cruz Biotech), and stained with labeled protein. From past experience and the literature, 5.5 µg/ml of annexin protein was used for staining. This amount was adjusted for equimolar addition of PrS by assuming the molecular weights of annexin to be 36 kD and the recombinant PrS to be 30 kD, based on the gel images provided. The cells were stained for 15 min. Hoechst 33342 dye was used for visualizing nucleic acid. The wells were then washed with AB and observed using the EVOS fluorescence microscope while still viable. For confocal microscopy, the Leica SP8 microscope in the Stanford Cell Sciences Imaging Facility was employed. The wells were then washed with AB and observed using the Leica sp8 microscope. Hoechst 33342 dye was used for visualizing nuclei. For toxicity studies, PrS was added to trophoblast stem cells (TSCs) and the viability tested with trypan blue using a Nexcelom Cellometer.

To test the labeled proteins for the ability to detect tumors, $5\times10^4$ 4 T1-luc cells were implanted into groups of 5 male BALB/c mice, in the left axillary fat pad. The mice were imaged with in vivo bioluminescence imaging (BLI) each day to monitor tumor growth, starting at 1 week post implantation. The mice were then treated on day 11 post implantation with 13 mg/kg body weight of intraperitoneal (IP) doxorubicin, and BLI was performed the next day. Control mice bearing tumors were left untreated with doxorubicin. 48 hrs post treatment the mice were imaged 1 hr after intravenous tracer injection (anesthesia 1.3 g/kg of urethane IP), with single head A-SPECT gamma camera (Gamma *Medica*); 1 mm pin hole collimator, 128 steps into a 128×128 imaging matrix, 15 seconds per step, 2.7 cm ROR; FOV=upper chest/neck. The injected dose of each protiein was 160 µl (800 µCi). The animals were then sacrificed and biodistribution was performed. For the cycloheximide treatment experiment, groups of 5 young (7 week old) male Swiss Webster mice were anesthetized (1.3 g/kg of urethane IP) and injected intravenously with 50 mg/kg cycloheximide. 1 hr 45 min after cycloheximide injection, tracer was injected (PrS=180 ul/1.2 mCi per dose; annexin V=170 µl/1.05 mCi per dose). 45 min after tracer injection, the mice were imaged with 10 min static whole body images using a single head parallel hole collimator (128×128 matrix) on the A-SPECT gamma camera.

To test for the specific localization of fluorescent PrS to apoptotic sites due to infection in live animals, CD1 mice were injected intravenously with bioluminescent *Listeria monocytogenes*. This bacterial pathogen infects many organs including the spleen, in which extensive apoptosis of monocytes and granulocytes occurs. At certain times post infection, spleen is the primary site of bacterial replication and so splenic BLI signals from the bacteria can be correlated with the localization of probes for apoptosis. Mice were infected and imaged each day. When splenic signals were evident (day 2 post infection for $2 \times 10^5$ colony forming units of bacteria in 8 week old CD1 female mice), 300 mg/kg body mass of Cy5 PrS was injected into mice, the animals were sacrificed 30 min later, and the spleens removed, frozen in OCT, and sectioned for fluorescence microscopy. Uninfected control mice were employed.

Flow cytometry was performed. Freshly labeled FITC PrS, prepared as described above, was employed. Murine hematopoietic stem cells (HSCs) are routinely purified in this laboratory. The cells were isolated from normal mouse bone marrow by staining for c-Kit+, lineage-negative cells. To further characterize the cells, SLAM marker staining was also performed. These markers stain cells that self-renew and differentiate, whereas non-staining HSCs can only differentiate. Subsequent staining with FITC PrS revealed the percent positive in SLAM-staining cells, as shown in the Results. The cells were then sorted for FITC and examined with confocal microscopy, using Hoechst 33342 for nuclear visualization.

Results

Figure 1A:
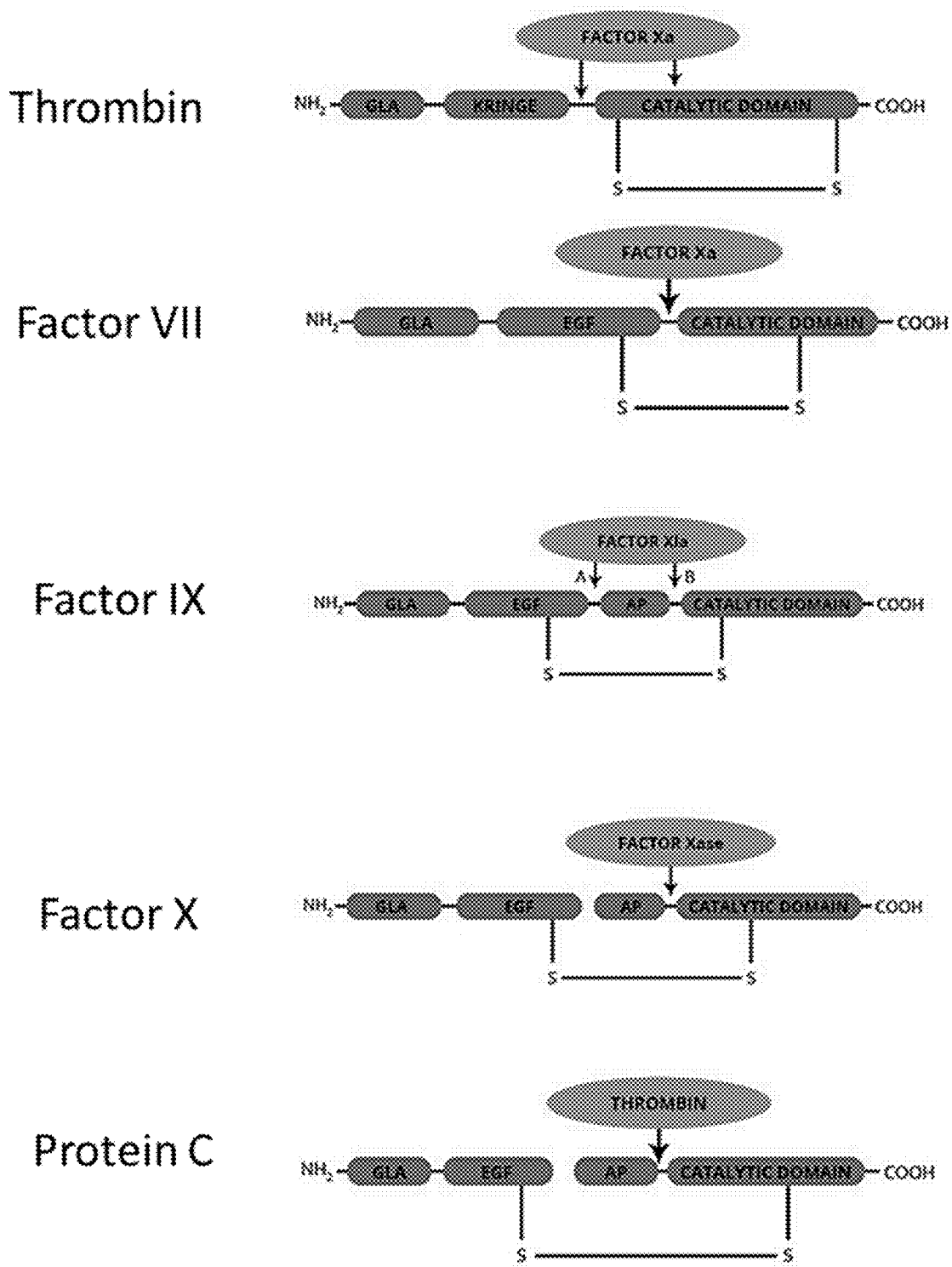
Figure 1B:
Figure 1C:
Figure 1D:
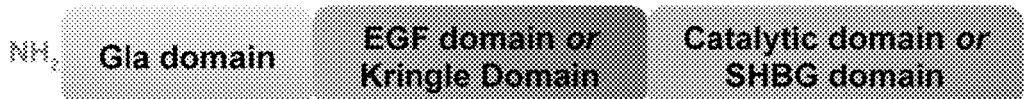
Figure 1D:
Figure 2:
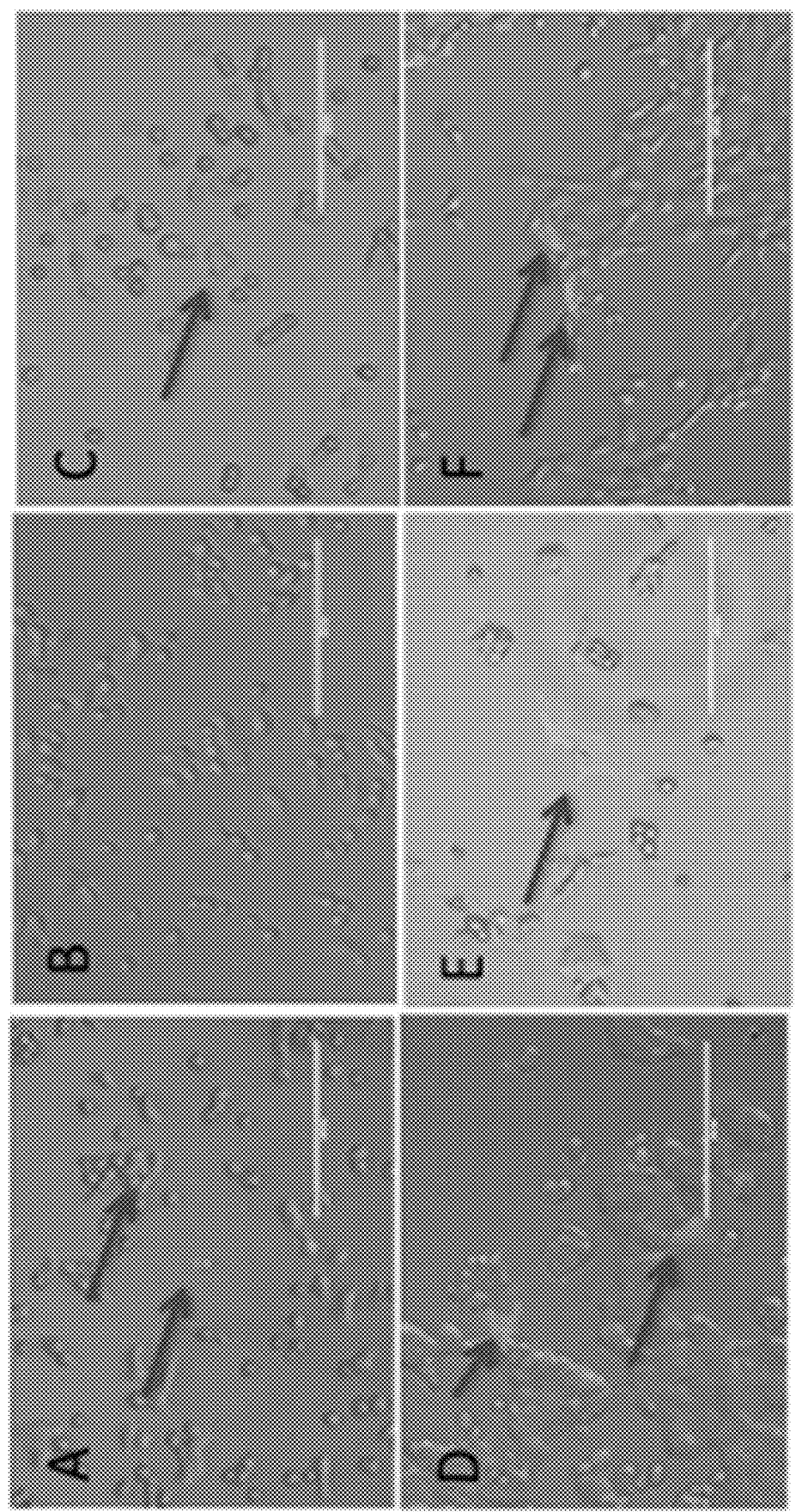
Figure 3:
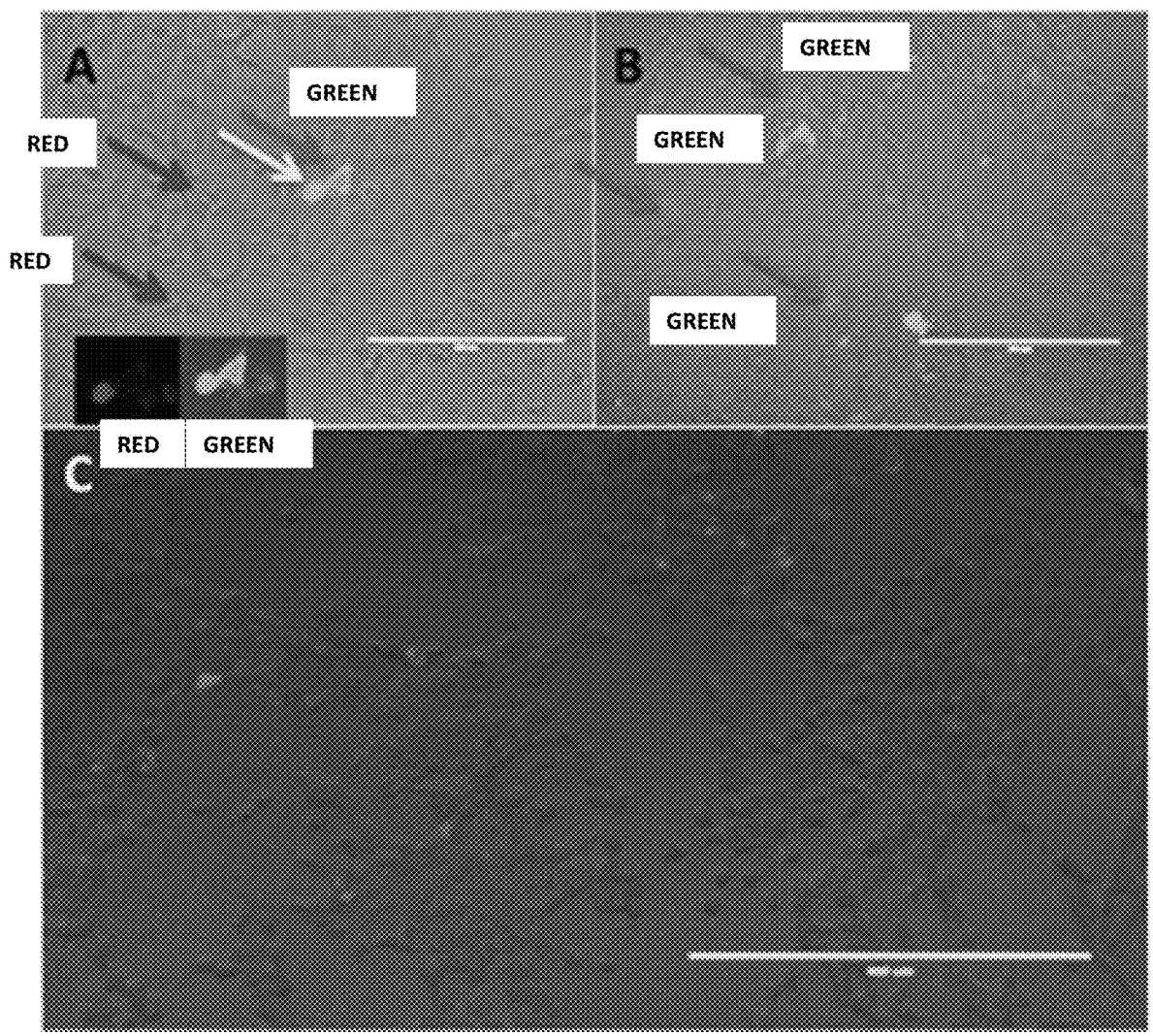
Figure 4:
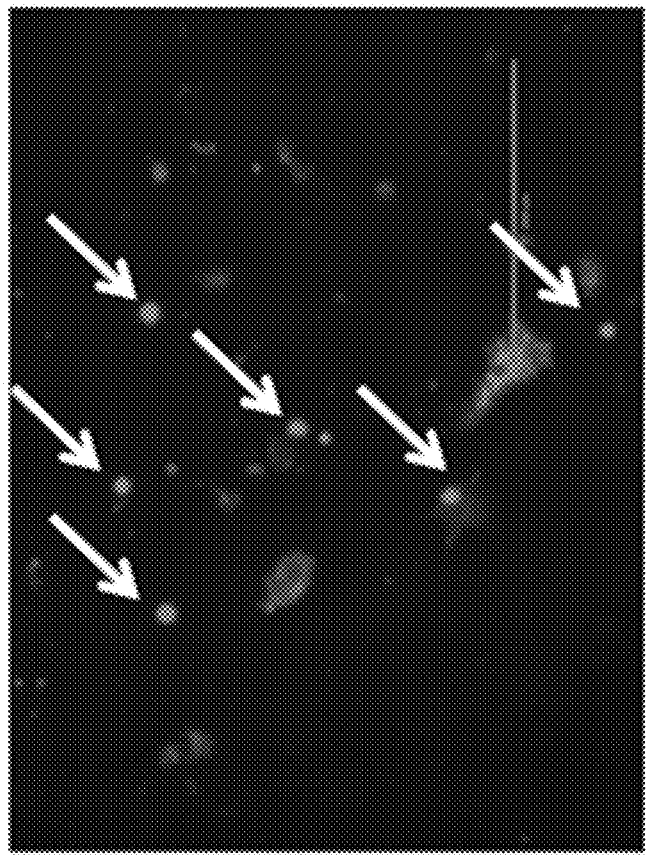
Figure 4:
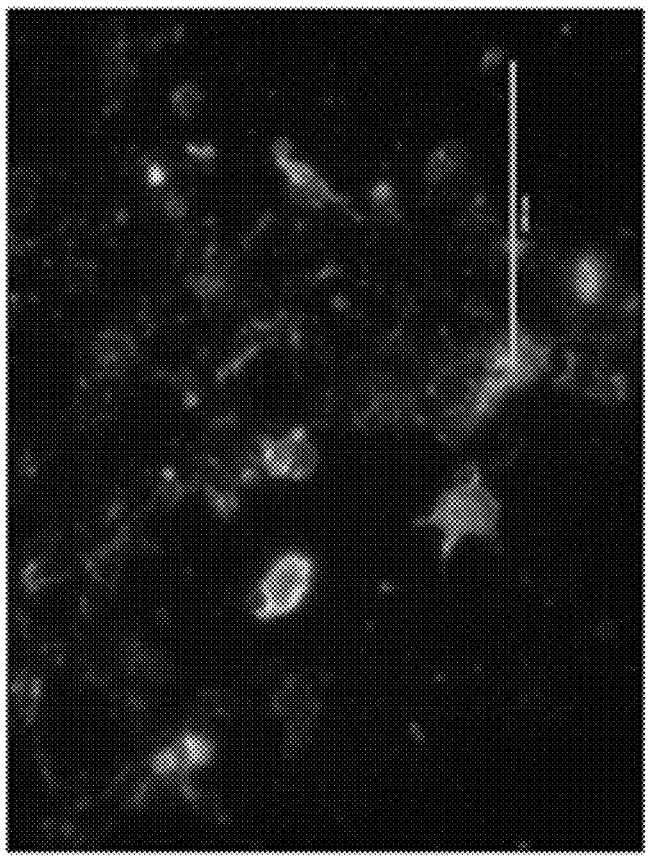
Figure 5:
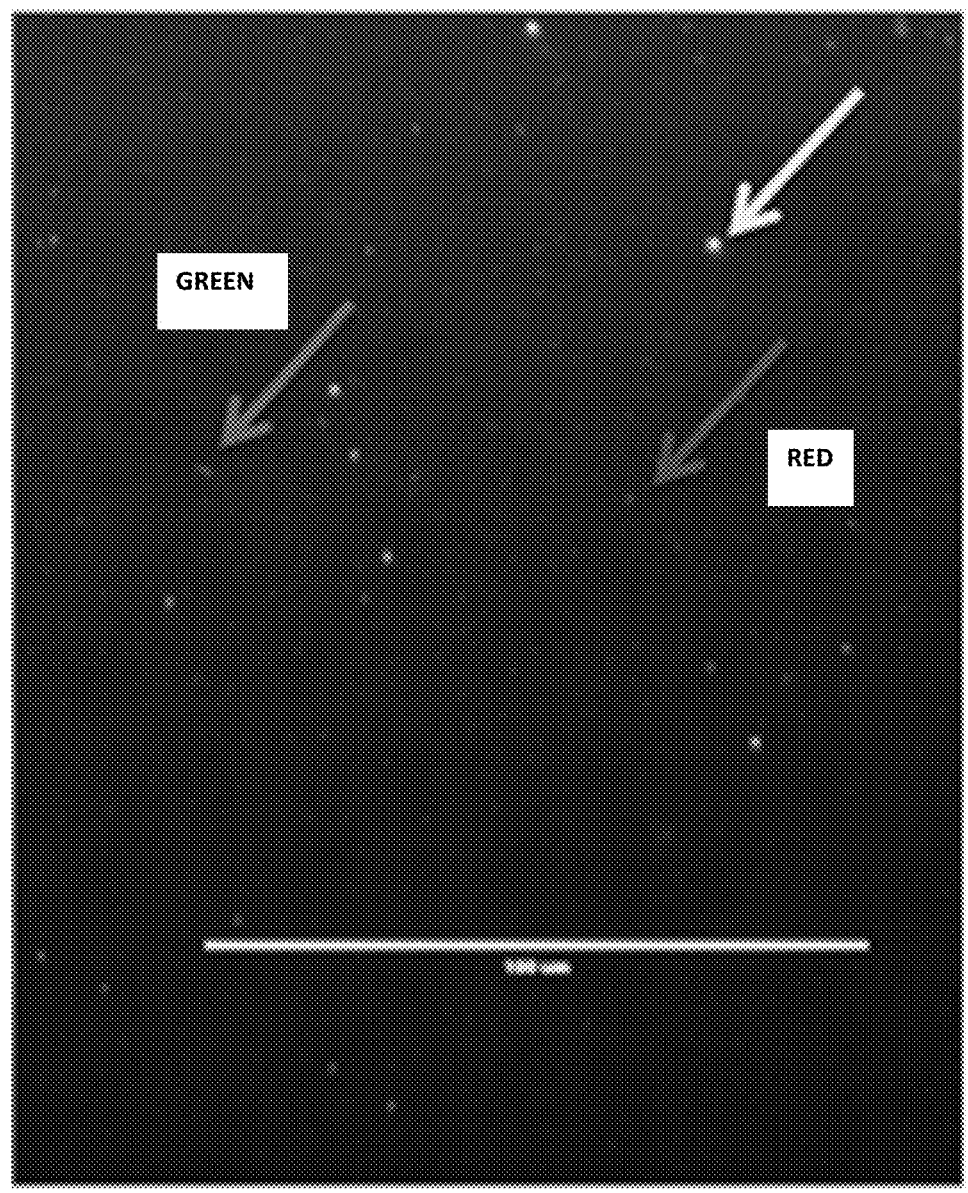

To assess PrS binding specificity in the context of apoptosis in cell culture, we employed several human and murine breast cancer cell lines. Apoptosis was induced with peroxide as described above, and FITC PrS binding was assessed. Examples of these experiments are shown in FIG. 2. Untreated cells exhibited minimal binding, such as shown in panel B of FIG. 2. Concentrations of peroxide and incubation times were chosen such that only a minority of cells would be affected, because at higher concentrations and/or longer incubation times the cells detached and staining and microscopy was not possible. In addition, the presence of many unaffected cells served as an internal negative control within each field. FITC-annexin showed specificity for apoptosis similar to PrS, serving as an internal positive control. We then tested the two proteins for co-localization and competitive binding. For co-localization, both FITC and Cy5 labeled PrS and annexin were prepared. 4T1 cells were treated with peroxide and stained with Cy5 and FITC labeled PrS and annexin, using both combinations of fluorophores. The cells were then visualized in the EVOS fluorescence microscope. The results are shown in FIG. 3. Under the conditions tested, all the brightly staining cells exhibited staining with both proteins. However, whether using Cy5 or FITC, PrS appeared to stain some cells that annexin did not, albeit weakly (FIG. 3). The relative staining intensity of different cells by each protein sometimes differed between the two probes, i.e., sometimes annexin stained two cells with equal intensity and PrS did not, and vice versa (FIG. 3A, green arrow and insert). Thus, while both probes generally stained the same cells, they appeared to exhibit subtle differences. In the competition assay, increasing excess amounts of unlabeled annexin were preincubated with apoptotic 4T1 cells for 15 min and the cells were then stained with Cy5 PrS. Surprisingly, the staining of PrS was not blocked by even 1,000 fold excess of annexin, the highest excess amount tested (FIG. 3C), although these proteins are thought to bind to the same target molecule, exposed P S. Co-staining of annexin and PrS was observed with many cell types. While the two proteins generally stained the same cells in each cell type, other differences became apparent. In particular, some objects smaller than cells were differentially stained (FIG. 4). These objects, which were present in increased numbers after peroxide treatment, were interpreted as apoptotic bodies; membrane-bound cell fragments produced during the fragmentation of apoptotic cells. As shown in FIG. 4, PrS stained these entities, whereas annexin did not, although some of these objects did stain with both proteins. This observation was unexpected. To further explore the differential staining of subcellular entities, extracellular vesicles (EVs) were prepared from 4T1 murine tumor cells using a standard centrifugation protocol. The two proteins also differentially stained these vesicles (FIG. 5), a result that may have biological and therapeutic implications.

EVs, specifically exosomes, microvesicles (MVs) and apoptotic bodies (ABs), are presumed to play key roles in cell-cell communication via transfer of biomolecules between cells. The biogenesis of these types of EVs differs, and they originate from either the endosomal (exosomes) or plasma membranes (MV) or are products of programmed cell death (ABs). All mammalian cells are thought to secrete EVs. Each type of EV can transfer molecular cargo to both neighboring and distant cells, affecting cellular behaviors such as those involved in tumor development and progression. In fact, EVs may play a role in nearly all the hallmarks of cancer, including sustaining proliferative signaling, evading growth suppression, resisting cell death, reprogramming energy metabolism, acquiring genomic instability, and developing the tumor microenvironment. They have also been implicated in the induction of angiogenesis, control of invasion, initiation of premetastatic niches, sustaining inflammation, and evading immune surveillance. Immune cells appear to also communicate through EVs and my recognize EVs as signals from tumor cells, infected tissues and wounds. A deeper understanding of the biology of EVs and their contribution to the hallmarks of cancer is leading to new possibilities for diagnosis and treatment of cancer. Development of additional EV surface markers is essential to advancing this field and PrS may be such a determinant.

Figure 6:
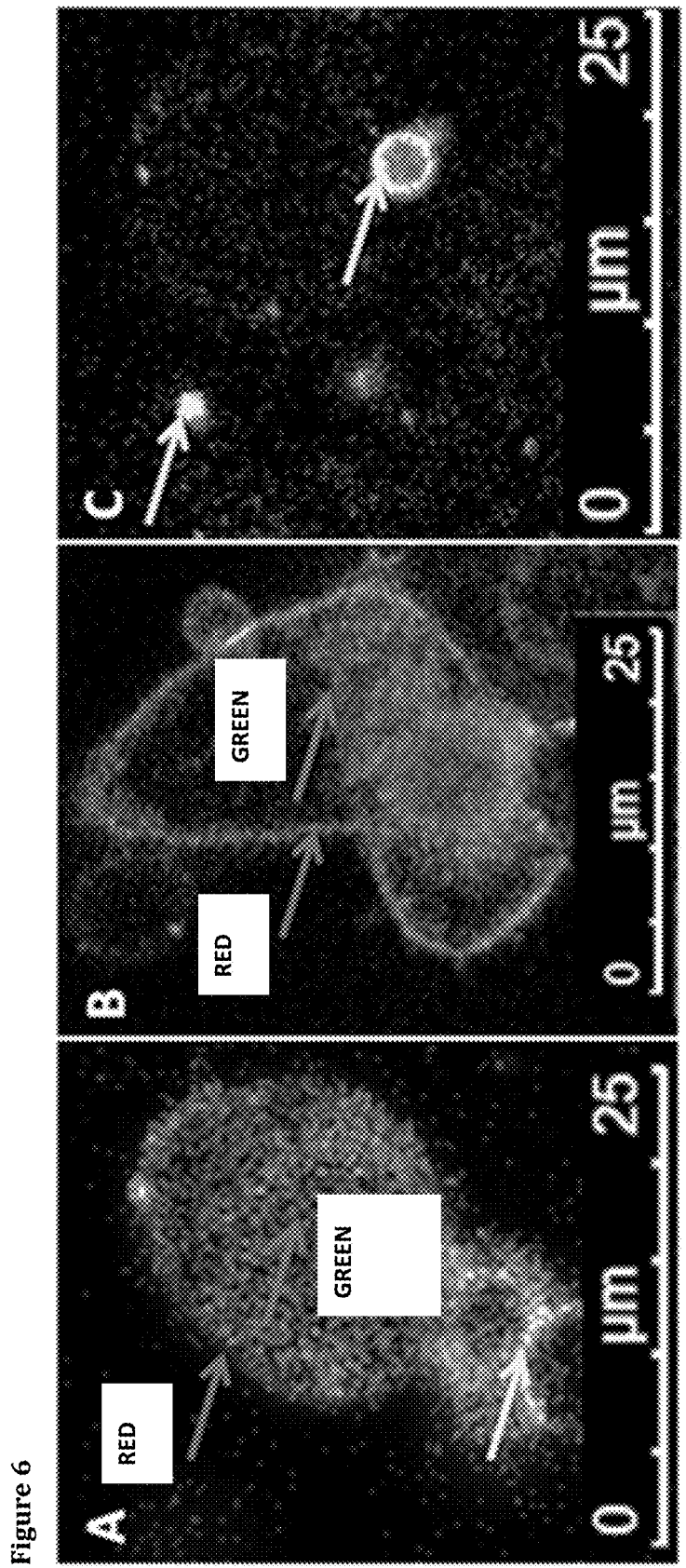

Following these studies with fluorescence microscopy, the subcellular localization of the staining by PrS and annexin was then evaluated via confocal microscopy. Murine 4T1 cells (lacking the Luc-GFP reporters) were plated on 8-part chamber slides at 1×10$^4$ cells per chamber and apoptosis was induced with 2 mM H$_2$O$_2$ or t-BHP (2 hr exposure) the next day. The cells were then washed and stained for 15 min with PrS and annexin. Hoechst 33342 dye was used to stain nucleic acid. In all cases, the most brightly staining cells were stained with both probes. However, in many cells labeled PrS was observed in the cytoplasm, whereas the labeled annexin was not (FIG. 6). Although annexin was internalized and appears in vesicles of a few cells, internalized annexin together with surface localized PrS in the same cell was not observed. These results were unexpected, because the two proteins are both presumed to bind PS.

Figure 7:
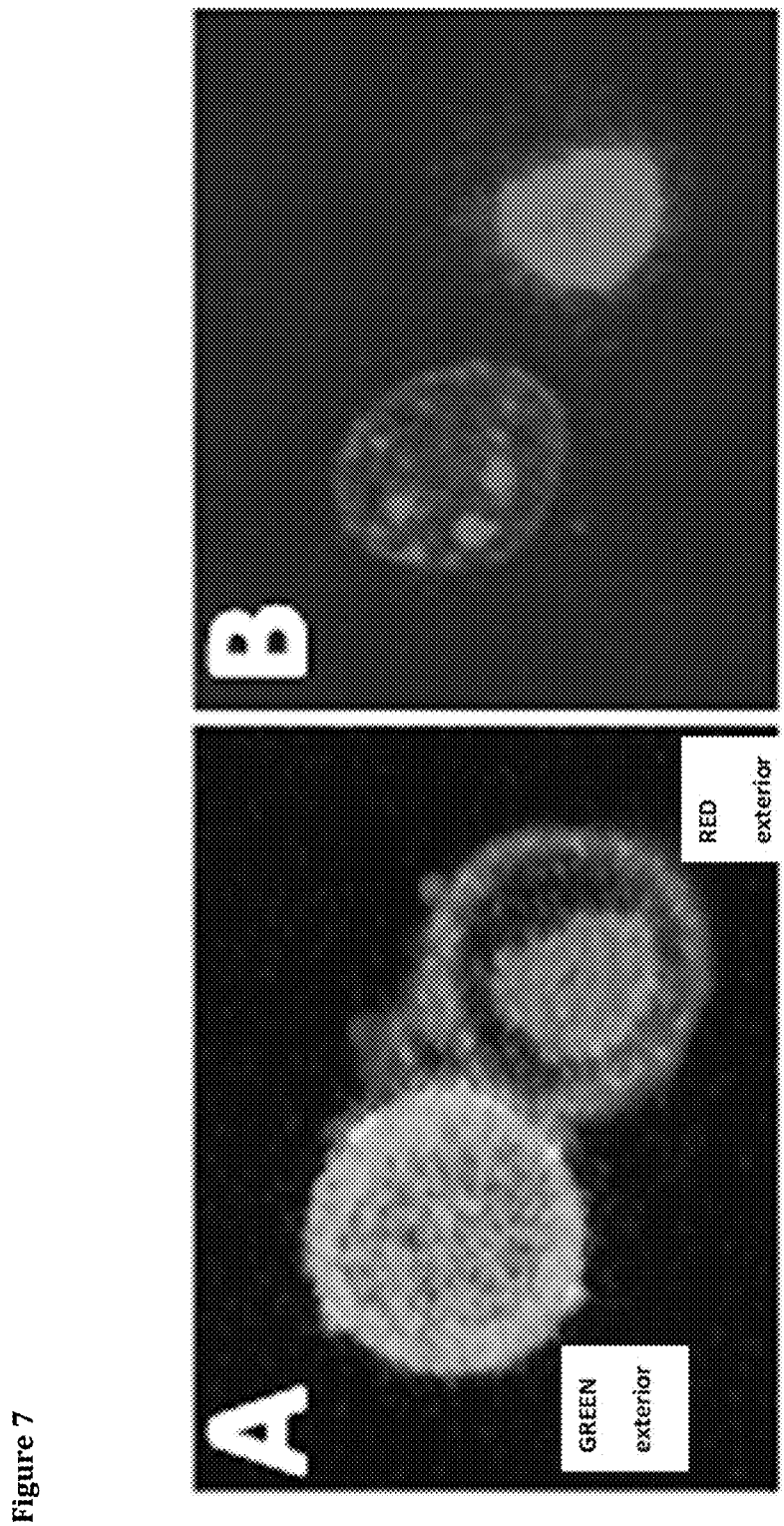
Figure 8:
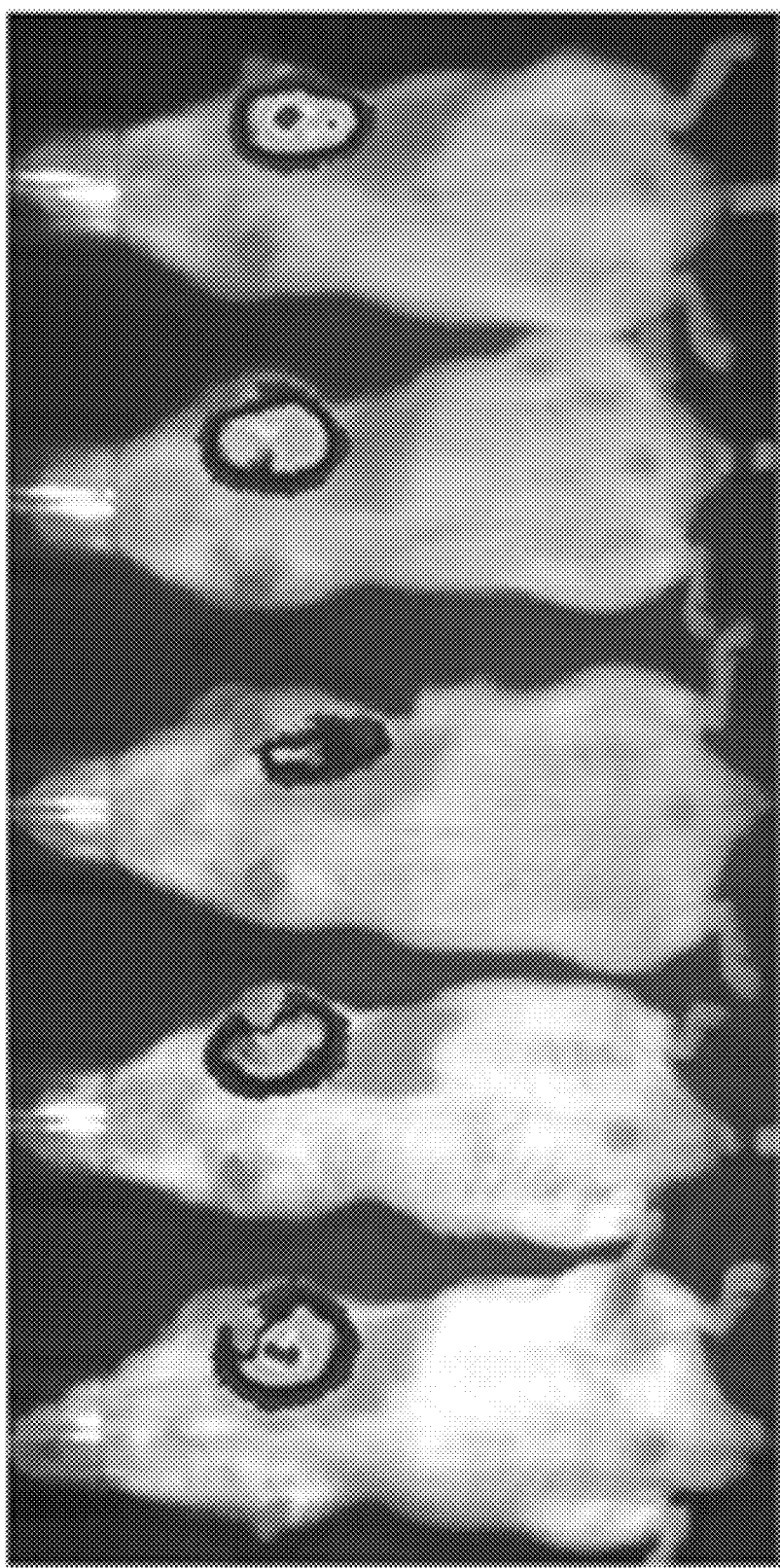
Figure 9:
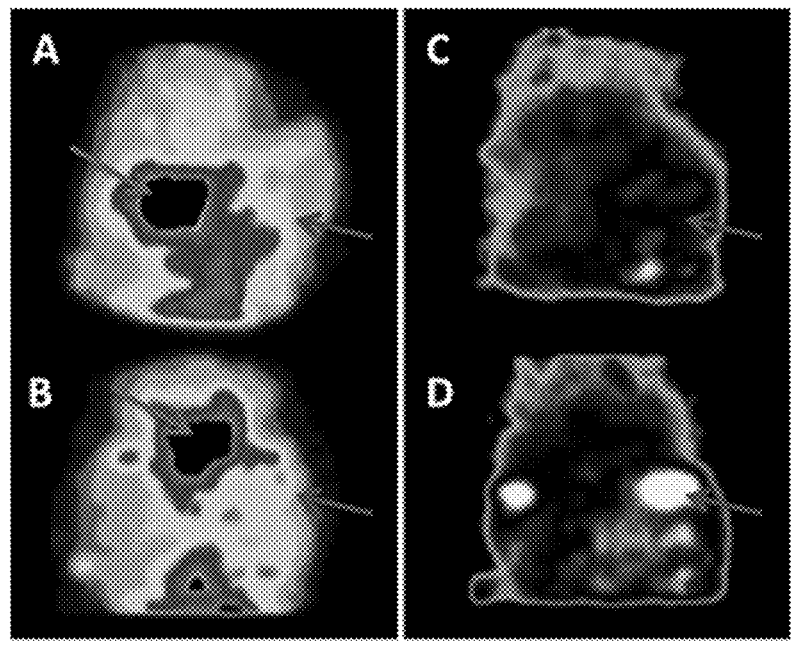

Clearly however, the two proteins responded differently to the inhibitors tested. To further study the internalization of PrS, a time course experiment was performed. Apoptotic 4T1 cells were stained for 5 min with Cy5 annexin and FITC PrS, and observed within 5 min of the addition of the probes. PrS was observed in the cytoplasm of these cells immediately, indicating internalization within 5 min (FIG. 7). The time course images also showed that PrS and annexin did not always stain the same cells equally at early time points. The cells in FIG. 7 appear to be in different stages of apoptosis, as the cell on the left shows an uncondensed nucleus surrounded by an apparently intact nuclear membrane, whereas the right cell exhibits the strong staining often characteristic of chromatin condensation that occurs later in the apoptotic process. Staining patterns such as these may indicate that PrS binds earlier in apoptosis than annexin. Although purely conjecture at this point, such a preference would explain many of the differences between these proteins that have been observed so far. For example, the staining of some cells by PrS and not annexin, such as in FIGS. 3A and B may be due to PrS binding earlier in the process of apoptosis. To examine PrS localization in live animals, several experiments were performed. These studies employed chemical and infectious induction of apoptosis in vivo, as well as the localization of PrS to tumors treated with doxorubicin, which is known to induce apoptosis. SPECT imaging using HYNIC-labeled PrS and annexin was performed in animals given 4T1luc breast tumors and treated with doxorubicin. Because the 4T1 tumors have been labeled with luciferase, they can be imaged in mice using in vivo bioluminescence imaging (BLI). One of the images from this experiment is shown in FIG. 8. This method can be used to evaluate tumor implantation and to follow progression in individual animals over time. $^{99m}$Tc labeled PrS and annexin were then employed for SPECT imaging of animals treated with doxorubicin and controls. An example of the results is shown in FIG. 9. The images of the head and thorax of the two animals show non-specific accumulation of the PrS probe in the salivary gland, and a low signal to noise ratio using this probe. Therefore, the threshold of the display in the PrS images shown was lowered to reveal more background, resulting in the brighter false-color of the images. The low signal-to-noise ratio is likely due to HYNIC labeling of only 1 mg of protein, which is suboptimal, and also due to the inability to perform controlled studies of HYNIC:protein labeling ratio.

Figure 10:
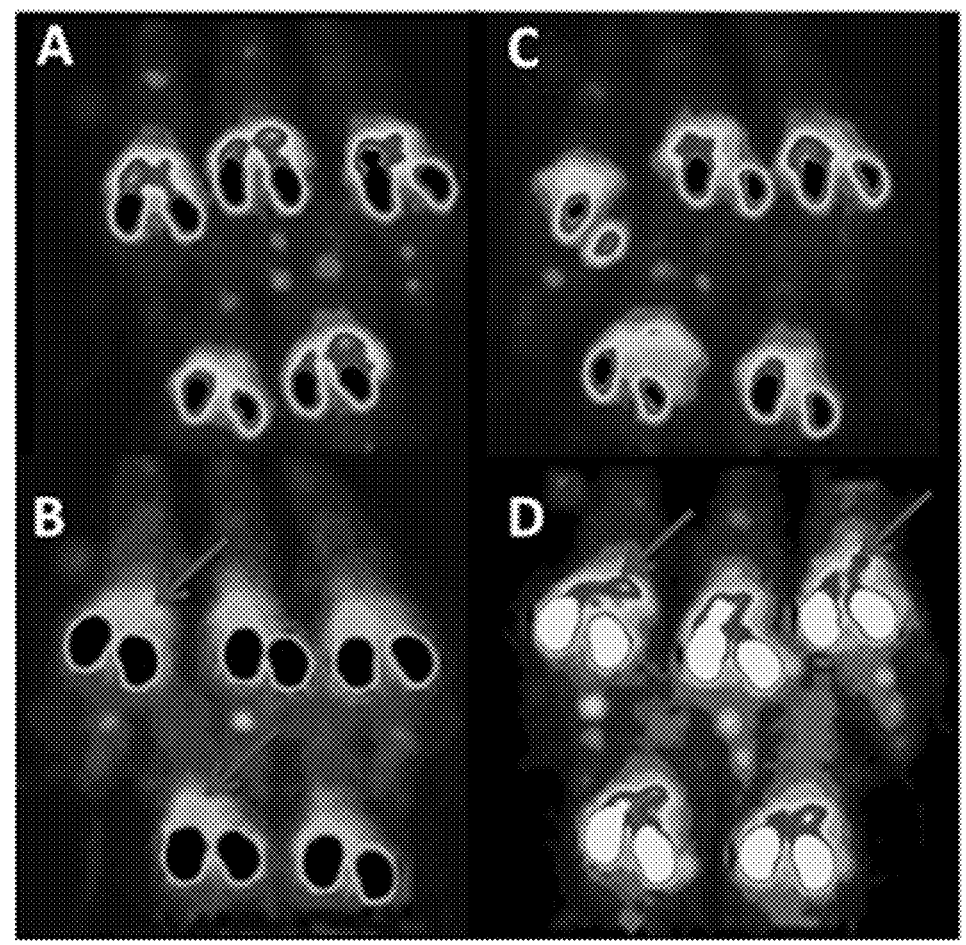
Figure 11:
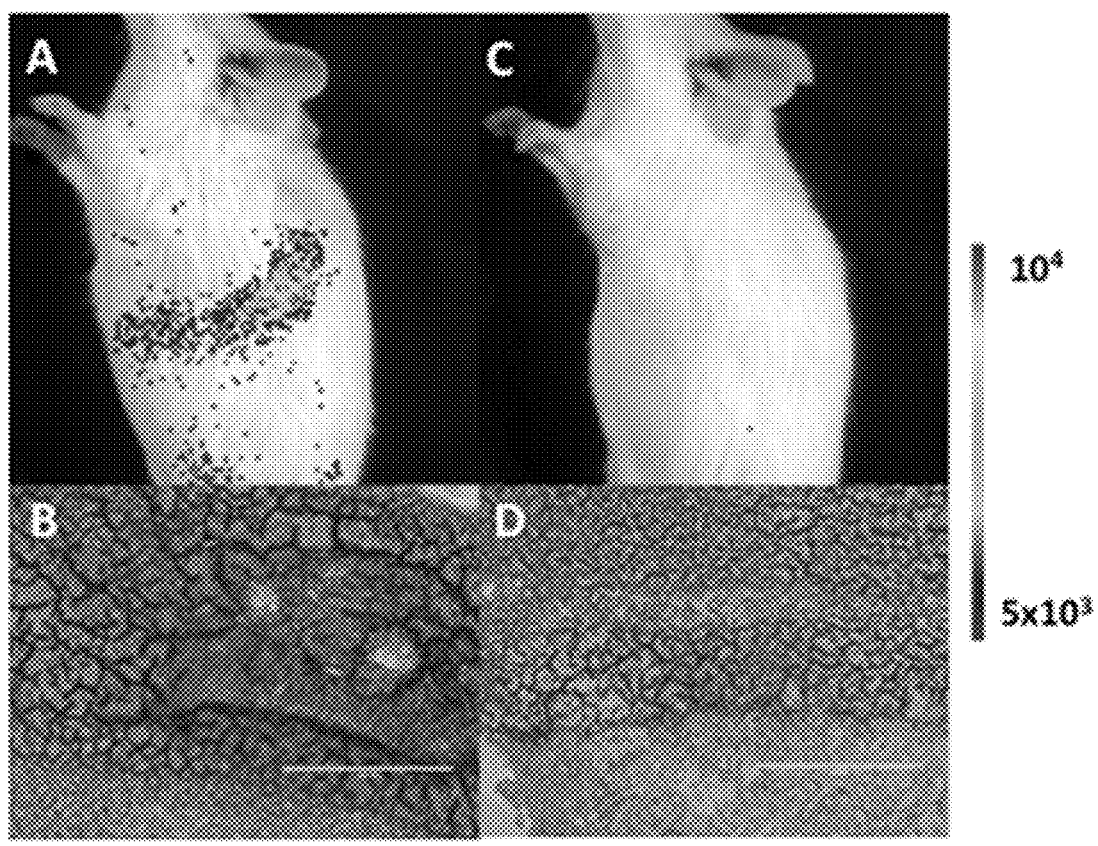

SPECT imaging of mice treated with cyclohexamide, which induces apoptosis in the liver, was also performed (FIG. 10). In FIG. 10, the whole-body images of 5 mice are shown in each panel. As with many radiolabeled probes, background is seen in the kidneys. Treatment of the mice with cyclohexamide increased the annexin SPECT signal in the liver. Again, the PrS showed low signal compared to annexin. Annexin was able to detect the apoptotic livers of cyclohexamide treated mice, whereas PrS showed only slight increase of signal in the liver due to treatment. To test the localization of PrS to apoptotic tissues and treated tumors independently of SPECT imaging and the concomitant complications of HYNIC labeling, mice infected with bacteria that induce apoptotic responses and tumor bearing mice were injected with Cy5 PrS. For infection, we employed *Listeria monocytogenes*, a bacterial pathogen labeled with luciferase and well characterized for BLI. Characteristic BLI signals from the spleen provide for excellent co-localization studies. CD1 mice were infected as described above and were imaged with BLI on day 2 post infection. The mice were then injected with Cy5 PrS and 30 min later sacrificed, and the spleens removed for sectioning and fluorescence microscopy (FIG. 11). In all cases, splenic sections from infected mice showed much greater Cy5 fluorescence signals than controls. In FIG. 11, the infected mouse shown displayed low photon counts, indicating the infection had not yet progressed very far in this animal. Many mice exhibit 10 times this signal intensity from the spleen on this day. However, the Cy5 channel fluorescence was still very strong relative to the uninfected control shown. This result may reflect the ongoing innate immune response to infection, as granulocytes and macrophages have been shown to be the main source of annexin signal in such animals (these cells are programmed for apoptosis to limit tissue destruction).

Figure 12:
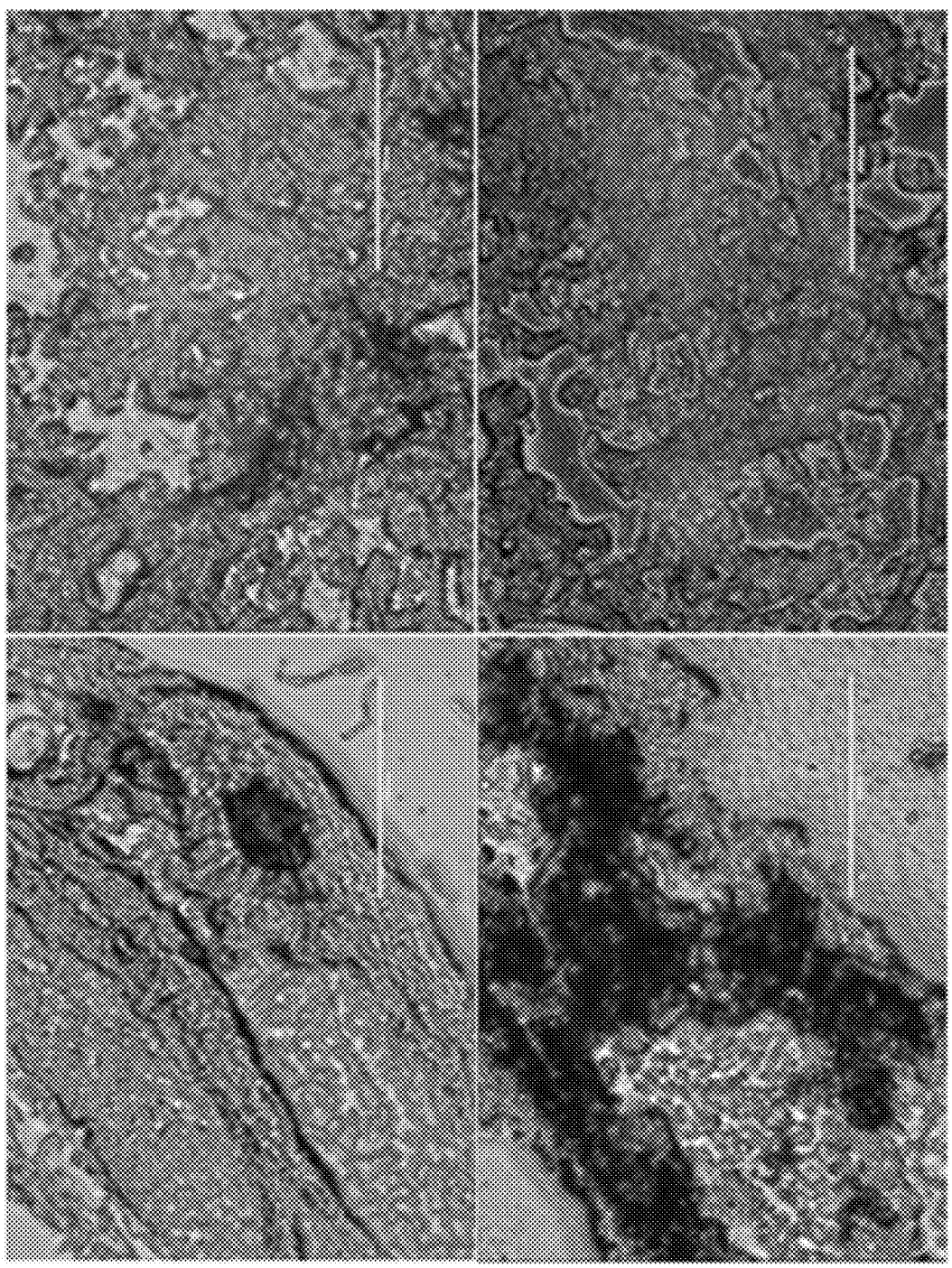

The localization of fluorescent PrS to 4T1 tumors treated with doxorubicin was then tested. Mice implanted with tumors were treated with doxorubicin as described above and Cy5 PrS was injected intravenously 30 min prior to sacrifice and removal of the tumors for sectioning and fluorescence microscopy. The results are shown in FIG. 12. Areas of intense staining were observed in the treated animals, whereas more modest signal was observed from the untreated tumor sections. Although some untreated tumors did exhibit small areas of higher signal than background, no signals of similar intensity to the treated tumors were observed in any of the untreated sections.

Figure 13:
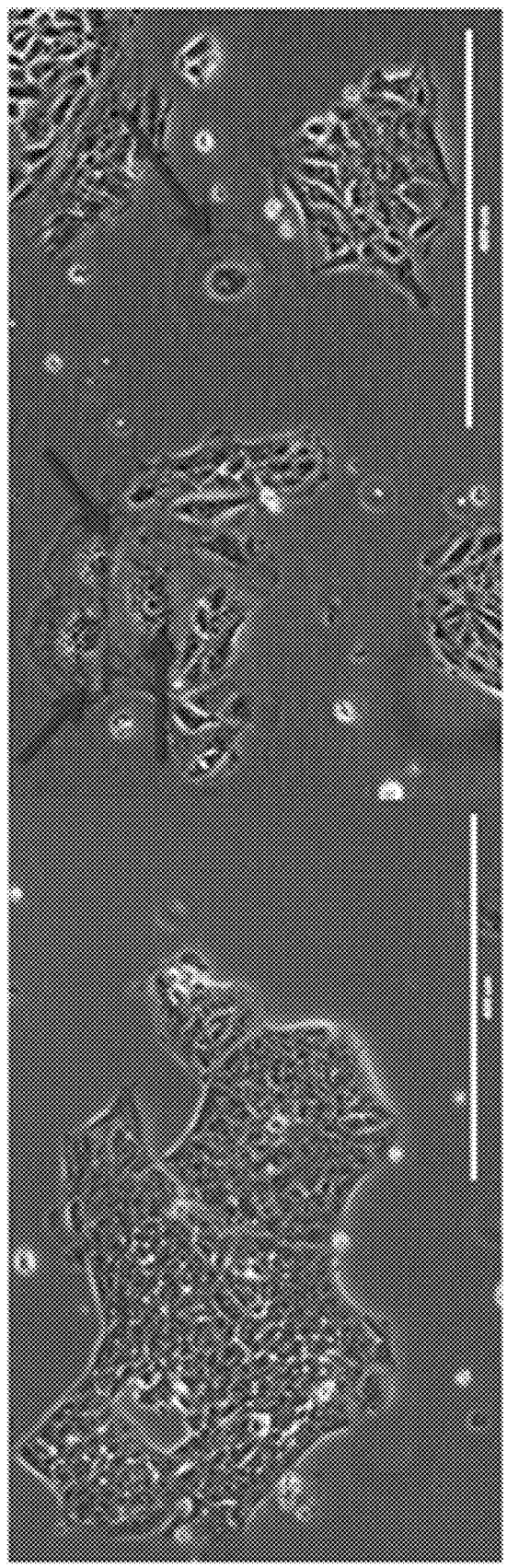
Figure 14:
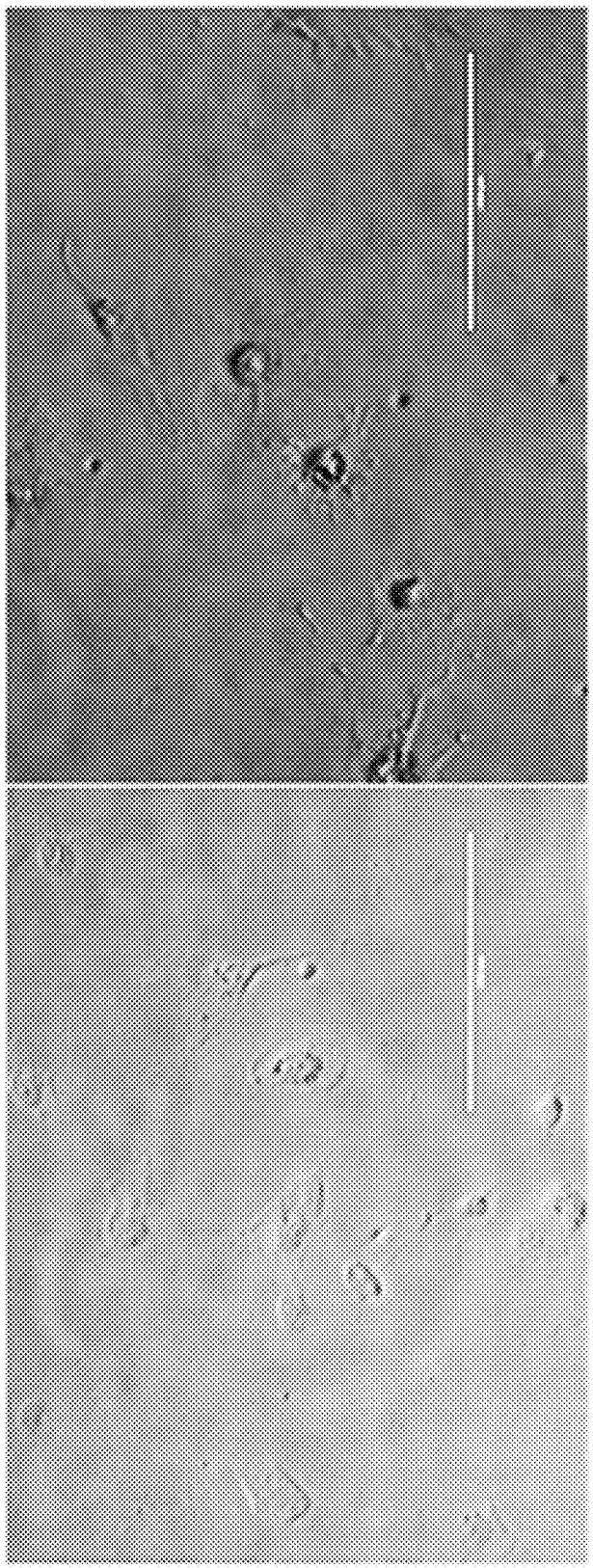
Figure 15:
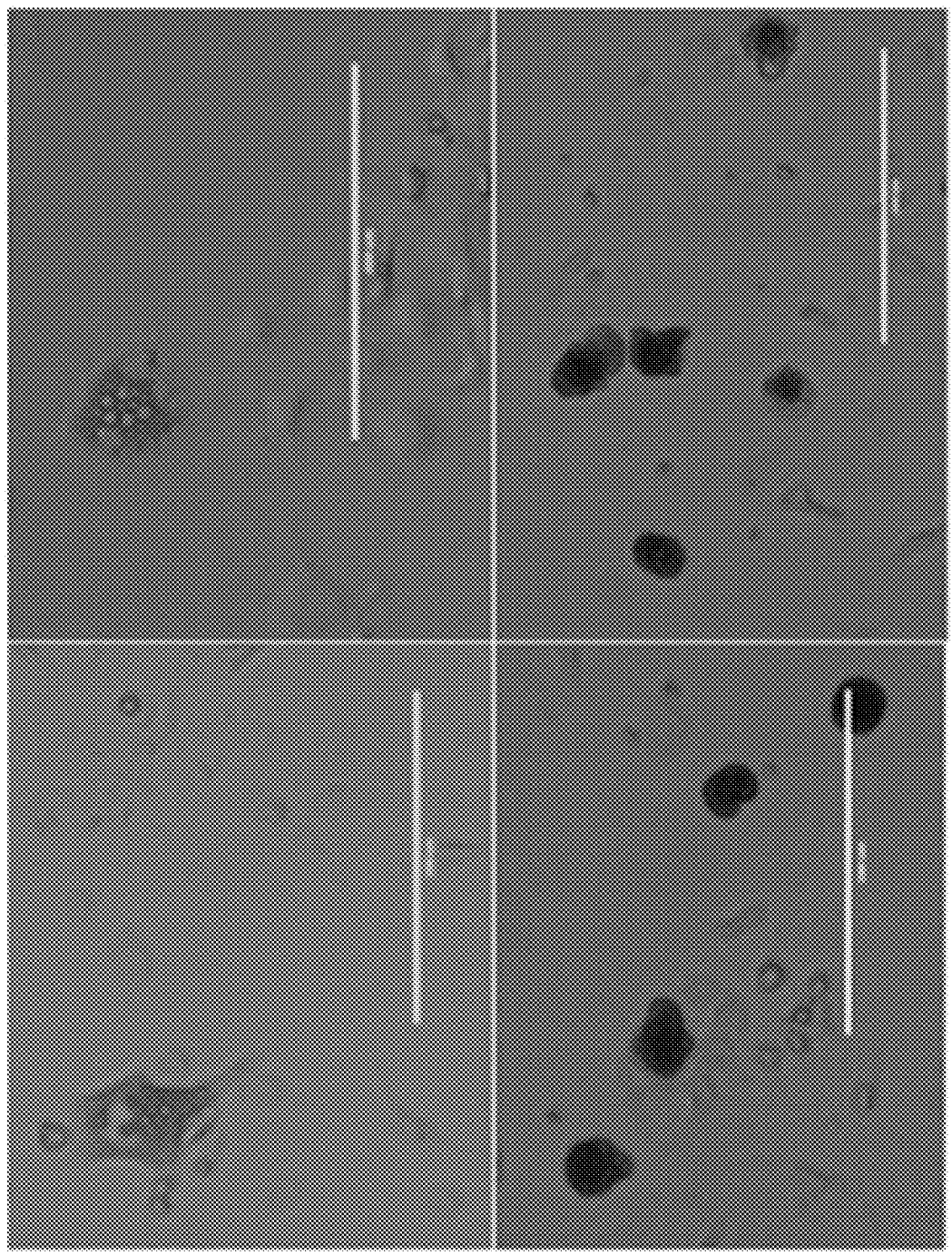

Stem cells are distinct in phenotype from differentiated cells and may express PS non-apoptotically to avoid the induction of immune responses. Trophoblast stem cells (TSCs) differentiate into several types of trophoblasts in culture. TSCs are prepared from mouse uterine scrapings grown in the presence of fibroblast growth factor, activin, and heparin. TSCs spontaneously differentiate into giant cells when these factors are removed from the medium (FIG. 13). TSCs stained with PrS, whereas differentiated trophoblasts derived from these cells in culture did not stain (FIG. 14). We have also determined that PrS is internalized into stem cells without apoptotic induction. This result confirms observations made in tumor cell lines, in which apoptosis was induced. Without induction of apoptosis, minimal staining was observed in tumor cells. To test for internalization in stem cells, we employed mesenchymal stem cells (MSCs) and TSCs. MSCs were prepared from mouse bone marrow. The bone marrow was flushed from mice and cultured for 6 days in the absence of growth factors. During this incubation, MSCs and hematopoietic stem cells (HSCs) replicate, whereas fibroblasts adhere but do not multiply beyond a few generations. After 6 days, a monolayer is visible. Upon passage by trypsinization, the adherent MSCs are retained, whereas the HSCs, which grow in suspension, are lost. The fibroblasts do not persist due to absence of growth factors and are also not retained. Thus, this simple procedure results in a nearly homogeneous population of MSCs. To confirm the identity of these cells, we treated the cultures separately with dexamethasone and glycerol phosphate (to induce differentiation into osteoblasts) or dexamethasone and indomethacin (to induce differentiation into adipocytes). The results are shown in FIG. 15. In response to the above treatments, differentiated cells showed the appearance of the respective cells. Adipocytes contained large fat vesicles and osteoblasts were dark with distinctive intracellular collagen and mineralization.

Figure 16:
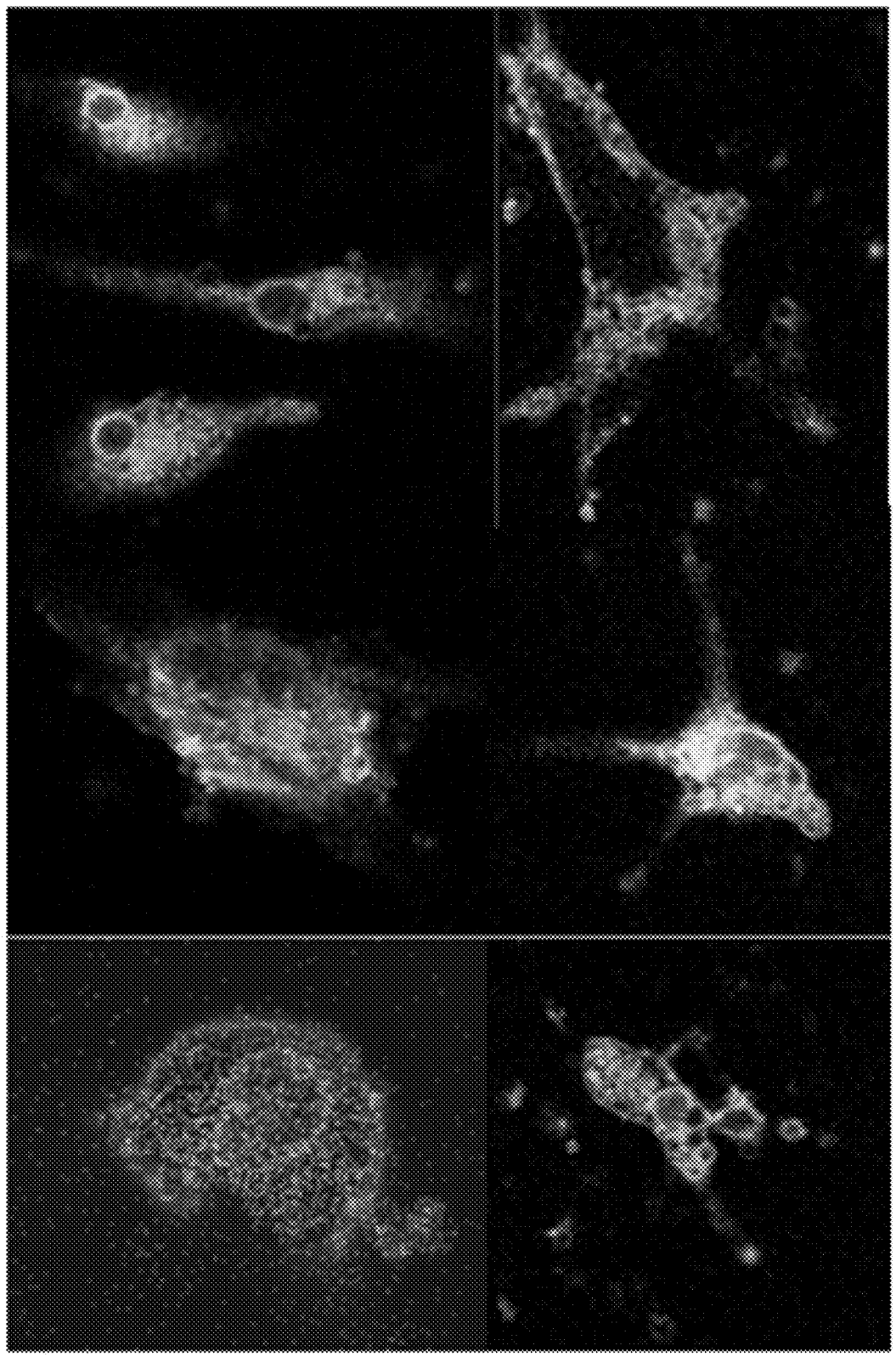
FIG. 16 Shows MSCs stained with PrS (green), annexin (red), and Hoechst (blue). Cells were imaged within 10 min of addition of the stain mixture.

To assess subcellular staining pattern, undifferentiated MSC were stained with PrS and annexin, as well as Hoechst nuclear staining reagent, and observed with confocal microscopy. Results of the observations are shown in FIG. 16. PrS was rapidly internalized. In the case of MSC, about 1 in 20 cells stained with PrS, consistent with previous data, however the precise percentage that stained was not determined. The morphology of MSCs is heterogeneous, and thee cells secrete abundant material into the medium, some of which adheres to the surface of the chamber slide, making resulting in background in some of the images. Nonetheless, the data clearly show internalized PrS, within 5 minutes of addition and annexin on the surface. TSCs were also stained and imaged as was done with the MSCs. The observations confirm internalization into these cells as well, which also occurs within 5 minutes of addition of the protein. The results are shown in FIG. 17. TSCs are morphologically quite variable, and can be multinucleate in the absence of differentiation, as can be seen in the figure. As with the MSCs, these primary cells shed abundant material into the medium, some of which we have established as extracellular vesicles (previous data). This material again makes the imaging difficult. Some EVs stain with annexin and not PrS, and this phenomenon can be seen in TSCs, in FIG. 18. In this image of a cluster of TSCs, vesicles being released by the cells stain with annexin and not PrS, which is internalized. These patterns raise interesting questions regarding the specificity and binding targets of PrS and annexin. The two proteins are both reputed to bind PS. However, the differential binding to EVs as well as distinct subcellular localization patterns suggest that they are not binding in exactly the same manner. Further studies will be required to establish the basis of this distinction, which may prove to be significant. We have also observed PrS staining of the neural progenitor cell line C17.2 (FIG. 19), which is a transformed cell line capable of differentiation in vitro into astrocytes and other neuronal cells. Approximately 5% of these transformed cells stained, although this percentage is an estimate. Remarkably, entry into TSCs occurred even when the cells were chilled to 4° C. (FIG. 20). However, it must be noted that the chamber could not be continually chilled once placed on the microscope. Nevertheless, the temperature could not have risen much within the 5 min time frame of the imaging procedure. This result, while provocative, must clearly be repeated under more controlled conditions. Should the finding be substantiated, the mechanism would have to be very interesting indeed.

We have succeeded in staining hematopoietic stem cells (HSC) with PrS. Using flow cytometry we determined that HSC stain with PrS, and have observed internalization of PrS in these cells with confocal microscopy. HSC were identified and isolated using fluorescence activated cell sorting (FACS). The cells were identified in bone marrow as lineage-negative, SCA/c-kit positive cells (FIG. 21). These were then stained with FITC-PrS. Two populations of HSC, short-term and long-term, can be identified with the pattern of SLAM marker staining. The SLAM (Signaling Lymphocyte Activation Molecule) markers CD48, CD150, CD229 and CD244 differentially stain HSC with distinct patterns such that SLAM pattern-positive staining is indicative of the ability to both self-renew and differentiate, whereas SLAM pattern-negative HSC can only differentiate. PrS stained a subset of long-term HSC (FIG. 22), and also short-term HSC (FIG. 23). The cells shown are propidium iodide (PI)-negative, meaning that they are all live cells. This result confirms previous experiments demonstrating that a subset of stem cells stains with PrS without the induction of apoptosis.

We then proceeded to test for internalization of PrS into HSC. This experiment was complicated by many factors. Perhaps the most difficult was the survival in culture of HSC, which die in large numbers in medium overnight. We therefore had to time the experiment such that flow cytometry analysis and confocal microscopy occurred on the same day. Furthermore, the cells are not adherent, making microscopy less than optimal. To make microscopy more efficient, the cells were resuspended in a small drop of medium. Finally, we needed to make sure that the PrS-stained cells analyzed by microscopy were still alive. Many HSC died during the processes of analysis and isolation. Therefore, PI was added and scanned in addition to the Hoescht nuclear stain, and another channel was employed. The presence of PI-bright nuclei indicated dead cells. Despite these difficulties and the complexities of timing, we were able to perform the experiment, and confirmed internalization of PrS into live HSC (FIG. 24). The cells were confirmed as alive by lack of nuclear PI staining. However, some cells were dead or dying as shown in FIG. 25. Despite the complexity and length of the experiment shown, the results show internalization.

Finally, in FIG. 26, we have performed preliminary toxicity studies on TSC, and determined that at a concentration of 135 μg/ml, viability was reduced only by a very minimal extent after 30 min, from 78% to 74%, relative to PBS. Considering that, at this level, 10% of the culture volume was PrS-containing solution, this result confirmed our qualitative observations that PrS is basically non-toxic to stem cells, and the minor toxicity observed could well be due to contaminating contents of the preparation itself. Lower concentrations of PrS showed no effect on viability. The highest level of protein tested was more than 1000 times the concentration used for staining. While full toxicity studies, which were not formally part of this project, will require much more extensive tests, in our hands PrS exhibits very little toxicity.

Summary

The above results have shown that PrS is rapidly internalized into an array of cells expressing PrS, including stem cells of many types, which suggests that PrS possesses unique characteristics amenable to manipulation toward the goal of developing a therapeutic agent. In addition, the difference in specificity between PrS and annexin such as seen in FIGS. 3 and 7 suggests that binding itself is different between these two proteins. The mere fact that annexin is a tetramer and PrS is a monomer cannot explain these differences and these data suggest that some other component on the cell surface may be involved in PrS binding. The mechanism of binding, specificity, and internalization of PrS, as well as the capability of modular manipulation provide a host of possibilities.

Example 2

Stem cells are distinct in phenotype from differentiated cells and may express PS non-apoptotically to avoid the induction of immune responses. Stem cells were stained with a GLA domain molecule of the present disclosure comprising a payload of a fluorescent label, without the induction of apoptosis.

Trophoblast stem cells, (FIG. 14) which differentiate into several types of trophoblasts in the placenta, stained with Protein S, whereas differentiated trophoblasts derived from these cells in culture did not stain. The stain was able to distinguish between in vivo differentiated stems cells and cells differentiated in vitro.

This data the molecules of the present disclosure may be employed to target cells in vivo or in ex vivo samples.

CONCLUSIONS

Extracellular vesicles represent an exciting opportunity for the diagnosis and treatment of an array of maladies. The present inventors have demonstrated that Gla domain recognizes the expression of phosphatidylserine. This property can be utilized for the: identification of extracellular vesicles expressing phophatidylserine, isolation of extracellular vesicles, targeting extracellular vesicles and/or loading the vesicles with, for example therapeutic materials. This is surprising because extracellular vesicles are minute subcellular entities.

REFERENCES

1. Thompson, W. W., et al., *Estimates of US influenza-associated deaths made using four different methods*. Influenza Other Respir Viruses, 2009. 3(1): p. 37-49.
2. Osterholm, M. T., et al., *Efficacy and effectiveness of influenza vaccines: a systematic review and meta-analysis*. Lancet Infect Dis, 2012. 12(1): p. 36-44.
3. Dixit, R., et al., *Emergence of oseltamivir resistance: control and management of influenza before, during and after the pandemic*. Infect Disord Drug Targets, 2013. 13(1): p. 34-45.
4. Jefferson, T., et al., *Oseltamivir for influenza in adults and children: systematic review of clinical study reports and summary of regulatory comments*. BMJ, 2014. 348: p. g2545.
5. Godfrey, C., et al., *Delivery is key: lessons learnt from developing splice-switching antisense therapies*. EMBO Mol Med, 2017. 9(5): p. 545-557.
6. Kaczmarek, J. C., P. S. Kowalski, and D. G. Anderson, *Advances in the delivery of RNA therapeutics: from concept to clinical reality*. Genome Med, 2017. 9(1): p. 60.
7. Ling, H., *Non-coding RNAs: Therapeutic Strategies and Delivery Systems*. Adv Exp Med Biol, 2016. 937: p. 229-37.
8. Poon, I. K., et al., *Apoptotic cell clearance: basic biology and therapeutic potential*. Nat Rev Immunol, 2014. 14(3): p. 166-80.
9. Birge, R. B., et al., *Phosphatidylserine is a global immunosuppressive signal in efferocytosis, infectious disease, and cancer*. Cell Death Differ, 2016.23(6): p. 962-78.
10. Amara, A. and J. Mercer, *Viral apoptotic mimicry*. Nat Rev Microbiol, 2015. 13(8): p. 461-9.
11. Moller-Tank, S. and W. Maury, *Phosphatidylserine receptors: enhancers of enveloped virus entry and infection*. Virology, 2014. 468-470: p. 565-80.
12. Ludwig, S., et al., *MEK inhibition impairs influenza B virus propagation without emergence of resistant variants*. FEBS Lett, 2004. 561(1-3): p. 37-43.
13. Sharma, R., et al., *Detection of phosphatidylserine-positive exosomes for the diagnosis of early-stage malignancies*. Br J Cancer, 2017. 117(4): p. 545-552.
14. Azuma, K., et al., *Liver-specific gamma-glutamyl carboxylase-deficient mice display bleeding diathesis and short life span*. PLoS One, 2014.9(2): p. e88643.
15. Hjortoe, G., et al., *Factor VIIa binding and internalization in hepatocytes*. J Thromb Haemost, 2005. 3(10): p. 2264-73.
16. Meliopoulos, V. A., et al., *Host gene targets for novel influenza therapies elucidated by high-throughput RNA interference screens*. FASEB J, 2012. 26(4): p. 1372-86.
17. Pleschka, S., et al., *Influenza virus propagation is impaired by inhibition of the Raf/MEK/ERK signalling cascade*. Nat Cell Biol, 2001. 3(3): p. 301-5.
18. Makkoch, J., et al., *Human microRNAs profiling in response to influenza A viruses (subtypes pH1N1, H3N2, and H5N1)*. Exp Biol Med (Maywood), 2016. 241(4): p. 409-20.
19. Wolf, S., et al., *MicroRNA Regulation of Human Genes Essential for Influenza A (H7N9) Replication*. PLoS One, 2016. 11(5): p. e0155104.
20. Skalickova, S., et al., *Perspective of Use of Antiviral Peptides against Influenza Virus*. Viruses, 2015. 7(10): p. 5428-42.
21. Matsubara, T., et al., *Sialic acid-mimic peptides as hemagglutinin inhibitors for anti-influenza therapy*. J Med Chem, 2010. 53(11): p. 4441-9.
22. Wunderlich, K., et al., *Identification of a P A-binding peptide with inhibitory activity against influenza A and B virus replication*. PLoS One, 2009. 4(10): p. e7517.
23. Ozcan, G., et al., *Preclinical and clinical development of siRNA-based therapeutics*. Adv Drug Deliv Rev, 2015. 87: p. 108-19.
24. Mack, S., et al., *Pseudo-Ligandless Click Chemistry for Oligonucleotide Conjugation*. Curr Protoc Chem Biol, 2016. 8(2): p. 83-95.
25. Paredes, E. and S. R. Das, *Click chemistry for rapid labeling and ligation of RNA*. Chembiochem, 2011. 12(1): p. 125-31.
26. Zheng, Y. and P. A. Beal, *Synthesis and evaluation of an alkyne-modified ATP analog for enzymatic incorporation into RNA*. Bioorg Med Chem Lett, 2016. 26(7): p. 1799-802.
27. Jain, N., et al., *Current ADC Linker Chemistry*. Pharm Res, 2015. 32(11): p. 3526-40.

The invention claimed is:

1. A method for targeting extracellular vesicles with surface exposed phosphatidyl serine, said method comprising: contacting a molecule comprising a gamma-carboxyglutamic acid component (GLA-component), said GLA-component comprises a GLA domain or an active fragment thereof, into a fluid that comprises the extracellular vesicle, and wherein the molecule does not comprise an active catalytic domain from a GLA protein;
wherein the GLA domain or active fragment thereof is selected from the group consisting of thrombin, factor IX, factor X, protein C, protein S, protein Z, Osteocalcin, Matrix GLA protein, GAS6, Transthretin, Periostin, Proline rich GLA 1, Proline rich GLA 2, Proline rich GLA 3 and Proline rich GLA 4.

2. The method according to claim 1, wherein the extracellular vesicle is an exosome.

3. The method according to claim 2, wherein the exosome has a diameter in the range 30 nm to 100 nm.

4. The method according to claim 1, wherein the vesicle has a density in the range 1 to 1.5 g/ml.

5. The method according to claim 1, wherein the vesicle comprises one or more transmembrane proteins selected from the group consisting of Lamp-1, Lamp-2, CD13, CD86, Flotillin, Syntaxin-3, CD2, CD36, CD40, CD40L, CD41a, CD44, CD45, ICAM-1, Integrin alpha4, LiCAM, LFA-1, Mac-1 alpha and beta, Vti-IA and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta, tetraspanins and combinations of two or more of the same.

6. The method according to claim 1, wherein the vesicle was released from an unhealthy cell.

7. The method according to claim 6, wherein the cell is a cancer cell.

8. The method according to claim 7, wherein the cell is a cancer stem cell.

9. The method according to claim 1, wherein the fluid comprises an ex vivo patient sample.

10. The method according to claim 1, wherein GLA domain or active fragment thereof is protein S.

11. The method according to claim 1, wherein GLA domain comprises a sequence shown in SEQ ID NO: 1.

12. The method according to claim 1, wherein the GLA-domain-component further comprises an EGF domain.

13. The method according to claim 12, wherein the EGF domain is selected from protein S.

14. The method according to claim 1, wherein the GLA-component comprises a sequence shown in SEQ ID NO: 6 or a derivative thereof wherein the His-tag is absent.

15. The method according to claim 1, wherein the GLA-domain component further comprises a Kringle domain.

16. The method according to claim 1, wherein the GLA-component is linked to a payload.

17. The method according to claim 16, wherein the GLA-component is conjugated to the payload.

18. The method according to claim 17, wherein the payload comprises a detectable label.

19. The method according to claim 18, wherein the label is selected from the group consisting of a fluorescent protein, a fluorescent probe, biotin, an enzyme, a tag, luminescent labels or compounds which may be detected by NMR or ESR spectroscopy including wherein the detectable label is in a Molecular Beacons.

20. The method according to claim 16, wherein the payload is a bead, plate or a tag.

21. The method according to claim 16, wherein the payload is linked to the GLA-component via a cleavable linker.

22. The method according to claim 1, wherein the method further comprises a further step of providing an enriched population of the vesicles.

23. The method according to claim 1, wherein the method comprises the step of isolating the vesicles.

24. The method according to claim 16, wherein the payload comprises a drug, a chemotherapeutic agent, a peptide or biological therapeutic.

25. The method according to claim 16, wherein the payload comprises a toxin, a polymer, biologically active proteins, a drug, nucleic acids and fragments thereof, a metal chelating agent, nanoparticles or a combination of two or more of the same.

26. The method according to claim 1, which comprises administering the vesicle comprising the GLA component and payload to a cancer patient.

* * * * *

SEQUENCE LISTING

<160> NUMBER OF SEQ ID NOS: 6

<210> SEQ ID NO 1
<211> LENGTH: 45
<212> TYPE: PRT
<213> ORGANISM: Artificial sequence
<220> FEATURE:

```
<223> OTHER INFORMATION: Synthetic peptide
<220> FEATURE:
<221> NAME/KEY: misc_feature
<222> LOCATION: (6)..(7)
<223> OTHER INFORMATION: X is gamma-carboxyglutamic acid residue
<220> FEATURE:
<221> NAME/KEY: misc_feature
<222> LOCATION: (14)..(14)
<223> OTHER INFORMATION: X is gamma-carboxyglutamic acid residue
<220> FEATURE:
<221> NAME/KEY: misc_feature
<222> LOCATION: (16)..(16)
<223> OTHER INFORMATION: X is gamma-carboxyglutamic acid residue
<220> FEATURE:
<221> NAME/KEY: misc_feature
<222> LOCATION: (19)..(20)
<223> OTHER INFORMATION: X is gamma-carboxyglutamic acid residue
<220> FEATURE:
<221> NAME/KEY: misc_feature
<222> LOCATION: (25)..(26)
<223> OTHER INFORMATION: X is gamma-carboxyglutamic acid residue
<220> FEATURE:
<221> NAME/KEY: misc_feature
<222> LOCATION: (29)..(29)
<223> OTHER INFORMATION: X is gamma-carboxyglutamic acid residue
<220> FEATURE:
<221> NAME/KEY: misc_feature
<222> LOCATION: (32)..(32)
<223> OTHER INFORMATION: X is gamma-carboxyglutamic acid residue
<220> FEATURE:
<221> NAME/KEY: misc_feature
<222> LOCATION: (36)..(36)
<223> OTHER INFORMATION: X is gamma-carboxyglutamic acid residue

<400> SEQUENCE: 1

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
            20                  25                  30

Asn Asp Pro Xaa Thr Asp Tyr Phe Tyr Pro Lys Tyr Leu
            35                  40                  45

<210> SEQ ID NO 2
<211> LENGTH: 46
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: X is gamma-carboxyglutamic acid residue
<220> FEATURE:
<221> NAME/KEY: misc_feature
<222> LOCATION: (11)..(11)
<223> OTHER INFORMATION: X is gamma-carboxyglutamic acid residue
<220> FEATURE:
<221> NAME/KEY: misc_feature
<222> LOCATION: (15)..(15)
<223> OTHER INFORMATION: X is gamma-carboxyglutamic acid residue
<220> FEATURE:
<221> NAME/KEY: misc_feature
<222> LOCATION: (17)..(17)
<223> OTHER INFORMATION: X is gamma-carboxyglutamic acid residue
<220> FEATURE:
<221> NAME/KEY: misc_feature
<222> LOCATION: (20)..(21)
<223> OTHER INFORMATION: X is gamma-carboxyglutamic acid residue
<220> FEATURE:
<221> NAME/KEY: misc_feature
<222> LOCATION: (26)..(27)
<223> OTHER INFORMATION: X is gamma-carboxyglutamic acid residue
<220> FEATURE:
<221> NAME/KEY: misc_feature
<222> LOCATION: (30)..(30)
```

<220> FEATURE:
<221> NAME/KEY: misc_feature
<222> LOCATION: (33)..(33)
<223> OTHER INFORMATION: X is gamma-carboxyglutamic acid residue
<220> FEATURE:
<221> NAME/KEY: misc_feature
<222> LOCATION: (35)..(35)
<223> OTHER INFORMATION: X is gamma-carboxyglutamic acid residue
<220> FEATURE:
<221> NAME/KEY: misc_feature
<222> LOCATION: (40)..(40)
<223> OTHER INFORMATION: X is gamma-carboxyglutamic acid residue

<400> SEQUENCE: 2

Ala Gly Ser Tyr Leu Leu Xaa Xaa Leu Phe Xaa Gly Asn Leu Xaa Lys
1               5                   10                  15

Xaa Cys Tyr Xaa Xaa Ile Cys Val Tyr Xaa Xaa Ala Arg Xaa Val Phe
            20                  25                  30

Xaa Asn Xaa Val Val Thr Asp Xaa Phe Trp Arg Arg Tyr Lys
        35                  40                  45

<210> SEQ ID NO 3
<211> LENGTH: 45
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: X is gamma-carboxyglutamic acid residue
<220> FEATURE:
<221> NAME/KEY: misc_feature
<222> LOCATION: (14)..(14)
<223> OTHER INFORMATION: X is gamma-carboxyglutamic acid residue
<220> FEATURE:
<221> NAME/KEY: misc_feature
<222> LOCATION: (16)..(16)
<223> OTHER INFORMATION: X is gamma-carboxyglutamic acid residue
<220> FEATURE:
<221> NAME/KEY: misc_feature
<222> LOCATION: (19)..(20)
<223> OTHER INFORMATION: X is gamma-carboxyglutamic acid residue
<220> FEATURE:
<221> NAME/KEY: misc_feature
<222> LOCATION: (25)..(26)
<223> OTHER INFORMATION: X is gamma-carboxyglutamic acid residue
<220> FEATURE:
<221> NAME/KEY: misc_feature
<222> LOCATION: (29)..(29)
<223> OTHER INFORMATION: X is gamma-carboxyglutamic acid residue
<220> FEATURE:
<221> NAME/KEY: misc_feature
<222> LOCATION: (32)..(32)
<223> OTHER INFORMATION: X is gamma-carboxyglutamic acid residue

<400> SEQUENCE: 3

Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr Ala Thr Asp Val Phe Trp Ala Lys Tyr Thr
        35                  40                  45

<210> SEQ ID NO 4
<211> LENGTH: 45
<212> TYPE: PRT
<213> ORGANISM: Artificial sequence
<220> FEATURE:
<223> OTHER INFORMATION: Synthetic peptide

```
<220> FEATURE:
<221> NAME/KEY: misc_feature
<222> LOCATION: (6)..(7)
<223> OTHER INFORMATION: X is gamma-carboxyglutamic acid residue
<220> FEATURE:
<221> NAME/KEY: misc_feature
<222> LOCATION: (14)..(14)
<223> OTHER INFORMATION: X is gamma-carboxyglutamic acid residue
<220> FEATURE:
<221> NAME/KEY: misc_feature
<222> LOCATION: (16)..(16)
<223> OTHER INFORMATION: X is gamma-carboxyglutamic acid residue
<220> FEATURE:
<221> NAME/KEY: misc_feature
<222> LOCATION: (19)..(20)
<223> OTHER INFORMATION: X is gamma-carboxyglutamic acid residue
<220> FEATURE:
<221> NAME/KEY: misc_feature
<222> LOCATION: (25)..(26)
<223> OTHER INFORMATION: X is gamma-carboxyglutamic acid residue
<220> FEATURE:
<221> NAME/KEY: misc_feature
<222> LOCATION: (29)..(29)
<223> OTHER INFORMATION: X is gamma-carboxyglutamic acid residue
<220> FEATURE:
<221> NAME/KEY: misc_feature
<222> LOCATION: (35)..(35)
<223> OTHER INFORMATION: X is gamma-carboxyglutamic acid residue

<400> SEQUENCE: 4

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser
        35                  40                  45

<210> SEQ ID NO 5
<211> LENGTH: 45
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: X is gamma-carboxyglutamic acid residue
<220> FEATURE:
<221> NAME/KEY: misc_feature
<222> LOCATION: (14)..(14)
<223> OTHER INFORMATION: X is gamma-carboxyglutamic acid residue
<220> FEATURE:
<221> NAME/KEY: misc_feature
<222> LOCATION: (16)..(16)
<223> OTHER INFORMATION: X is gamma-carboxyglutamic acid residue
<220> FEATURE:
<221> NAME/KEY: misc_feature
<222> LOCATION: (19)..(20)
<223> OTHER INFORMATION: X is gamma-carboxyglutamic acid residue
<220> FEATURE:
<221> NAME/KEY: misc_feature
<222> LOCATION: (25)..(26)
<223> OTHER INFORMATION: X is gamma-carboxyglutamic acid residue
<220> FEATURE:
<221> NAME/KEY: misc_feature
<222> LOCATION: (29)..(29)
<223> OTHER INFORMATION: X is gamma-carboxyglutamic acid residue
<220> FEATURE:
<221> NAME/KEY: misc_feature
<222> LOCATION: (32)..(32)
<223> OTHER INFORMATION: X is gamma-carboxyglutamic acid residue
<220> FEATURE:
<221> NAME/KEY: misc_feature
<222> LOCATION: (35)..(35)
<223> OTHER INFORMATION: X is gamma-carboxyglutamic acid residue
```

<400> SEQUENCE: 5

Ala Asn Ala Phe Leu Xaa Xaa Leu Arg Gln Gly Ser Leu Xaa Arg Xaa
1               5                   10                  15

Cys Lys Xaa Xaa Gln Cys Ser Phe Xaa Xaa Ala Arg Xaa Ile Phe Xaa
            20                  25                  30

Asp Ala Xaa Arg Thr Lys Leu Phe Trp Ile Ser Tyr Ser
        35                  40                  45

<210> SEQ ID NO 6
<211> LENGTH: 250
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: X is gamma-carboxyglutamic acid residue
<220> FEATURE:
<221> NAME/KEY: misc_feature
<222> LOCATION: (14)..(14)
<223> OTHER INFORMATION: X is gamma-carboxyglutamic acid residue
<220> FEATURE:
<221> NAME/KEY: misc_feature
<222> LOCATION: (16)..(16)
<223> OTHER INFORMATION: X is gamma-carboxyglutamic acid residue
<220> FEATURE:
<221> NAME/KEY: misc_feature
<222> LOCATION: (19)..(20)
<223> OTHER INFORMATION: X is gamma-carboxyglutamic acid residue
<220> FEATURE:
<221> NAME/KEY: misc_feature
<222> LOCATION: (25)..(26)
<223> OTHER INFORMATION: X is gamma-carboxyglutamic acid residue
<220> FEATURE:
<221> NAME/KEY: misc_feature
<222> LOCATION: (29)..(29)
<223> OTHER INFORMATION: X is gamma-carboxyglutamic acid residue
<220> FEATURE:
<221> NAME/KEY: misc_feature
<222> LOCATION: (32)..(32)
<223> OTHER INFORMATION: X is gamma-carboxyglutamic acid residue
<220> FEATURE:
<221> NAME/KEY: misc_feature
<222> LOCATION: (36)..(36)
<223> OTHER INFORMATION: X is gamma-carboxyglutamic acid residue

<400> SEQUENCE: 6

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
            20                  25                  30

Asn Asp Pro Xaa Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
    50                  55                  60

Ala Tyr Pro Asp Leu Arg Ser Cys Val Asn Ala Ile Pro Asp Gln Cys
65                  70                  75                  80

Ser Pro Leu Pro Cys Asn Glu Asp Gly Tyr Met Ser Cys Lys Asp Gly
                85                  90                  95

Lys Ala Ser Phe Thr Cys Thr Cys Lys Pro Gly Trp Gln Gly Glu Lys
            100                 105                 110

Cys Glu Phe Asp Ile Asn Glu Cys Lys Asp Pro Ser Asn Ile Asn Gly
            115                 120                 125

Gly Cys Ser Gln Ile Cys Asp Asn Thr Pro Gly Ser Tyr His Cys Ser

```
                    130                 135                 140
Cys Lys Asn Gly Phe Val Met Leu Ser Asn Lys Lys Asp Cys Lys Asp
145                 150                 155                 160

Val Asp Glu Cys Ser Leu Lys Pro Ser Ile Cys Gly Thr Ala Val Cys
                165                 170                 175

Lys Asn Ile Pro Gly Asp Phe Glu Cys Glu Cys Pro Glu Gly Tyr Arg
            180                 185                 190

Tyr Asn Leu Lys Ser Lys Ser Cys Glu Asp Ile Asp Glu Cys Ser Glu
        195                 200                 205

Asn Met Cys Ala Gln Leu Cys Val Asn Tyr Pro Gly Gly Tyr Thr Cys
    210                 215                 220

Tyr Cys Asp Gly Lys Lys Gly Phe Lys Leu Ala Gln Asp Gln Lys Ser
225                 230                 235                 240

Cys Glu Ser Arg His His His His His His
            245                 250
```